United States Patent
Volovitz et al.

(10) Patent No.: US 11,480,571 B2
(45) Date of Patent: Oct. 25, 2022

(54) CYTOMETRIC ASSAYS

(71) Applicant: The Medical Research, Infrastructure, and Health Services Fund of the Tel Aviv Medical Center, Tel Aviv (IL)

(72) Inventors: Ilan Volovitz, Tel Aviv (IL); Merav Lustgarten, Rehovot (IL); Zvi Ram, Ramat Gan (IL); Netanel Yakov Shapira, Efrat (IL); Idan Ben Horin, Ra'anana (IL); Gil Diamant, Tel-Aviv (IL)

(73) Assignee: The Medical Research, Infrastructure, and Health Services Fund of the Tel Aviv Medical Center, Tel Aviv (IL)

( * ) Notice: Subject to any disclaimer, the term of this patent is extended or adjusted under 35 U.S.C. 154(b) by 606 days.

(21) Appl. No.: 15/780,385

(22) PCT Filed: Nov. 30, 2016

(86) PCT No.: PCT/IL2016/051284
§ 371 (c)(1),
(2) Date: May 31, 2018

(87) PCT Pub. No.: WO2017/094008
PCT Pub. Date: Jun. 8, 2017

(65) Prior Publication Data
US 2018/0356420 A1 Dec. 13, 2018

Related U.S. Application Data

(60) Provisional application No. 62/261,336, filed on Dec. 1, 2015.

(51) Int. Cl.
*G01N 33/533* (2006.01)
*G01N 33/569* (2006.01)
(Continued)

(52) U.S. Cl.
CPC ..... *G01N 33/56972* (2013.01); *G01N 33/533* (2013.01); *G01N 33/56977* (2013.01);
(Continued)

(58) Field of Classification Search
CPC .......... G01N 33/533; G01N 33/56972; G01N 2333/705; G01N 2333/70514; G01N 2333/70517; G01N 2333/70596
See application file for complete search history.

(56) References Cited

U.S. PATENT DOCUMENTS 5,853,976 A 12/1998 Hesse et al.
5,952,215 A * 9/1999 Dwulet .................... C12N 9/52
435/220

(Continued)

FOREIGN PATENT DOCUMENTS

EP  2 438 446 B1  3/2014

OTHER PUBLICATIONS

Verykou et al. Enhancing diagnostic sensitivity for cutaneous blastic plasmacytoid dendritic cell neoplasia. British Journal of Dermatology. 167 (Suppl. 1) 100-113 DP25 (2012).*
(Continued)

*Primary Examiner* — Gailene Gabel
(74) *Attorney, Agent, or Firm* — The Roy Gross Law Firm, LLC; Roy Gross

(57) ABSTRACT

Provided relates to the field of cytometry, specifically to flow cytometric methods and kits for improved diagnosis, prognosis and monitoring of tumors and other lesions involving immune cell infiltration. Further provided are embodiments of the subject matter which relate to compositions and methods providing high resolution quantitative means for immunophenotyping and immune modeling, and for iden-
(Continued)

tification of disease prognostic and therapy predictive biomarkers.

14 Claims, 24 Drawing Sheets

Specification includes a Sequence Listing.

(52) U.S. Cl.
CPC .................. *G01N 2333/705* (2013.01); *G01N 2333/70514* (2013.01); *G01N 2333/70517* (2013.01); *G01N 2333/70596* (2013.01)

(56) References Cited

U.S. PATENT DOCUMENTS

| | | | | |
|---|---|---|---|---|
| 9,764,039 | B2* | 9/2017 | Thanos | A61K 47/6851 |
| 2012/0165213 | A1* | 6/2012 | van Dongen | G01N 33/5091 |
| | | | | 506/9 |
| 2013/0058902 | A1* | 3/2013 | Kishimoto | A61K 38/1816 |
| | | | | 424/93.7 |
| 2013/0060775 | A1 | 3/2013 | Qiu | |

OTHER PUBLICATIONS

Vuckovic et al. Dendritic Cell Subsets in Whole Blood Revealed by a Single-Platform Flow Cytometry Assay. Blood. 100 (11): Abstract No. 3626 (Nov. 16, 2002).*
Autissier et al. Evaluation of a 12-Color Flow Cytometry Panel to Study Lymphocyte, Monocyte, and Dendritic Cell Subsets in Humans. Cytometry Part A. 77A: 410-419 (2010).*
Basford et al., (2010) Optimized multiparametric immunophenotyping of umbilical cord blood cells by flow cytometry. Nat Protoc 5(7): 1337-1346.
Hensley-McBain et al., (2014) Optimization of a whole blood phenotyping assay for enumeration of peripheral blood leukocyte populations in multicenter clinical trials. J Immunol Methods 411: 23-26.
Kuruvilla et al., (2007) Dengue virus infection and immune response in humanized RAG2(-/-)gamma(cX-/-) (RAG-hu) mice. Virology 369(1): 143-152.
Wang et al., (2011) Erythroblastic sarcoma presenting as bilateral ovarian masses in an infant with pure erythroid leukemia. Hum Pathol 42(5): 749-758.
Database Biosis [onine], Biosciences Information Service, Philadelphia, PA, US; Dec. 2014 (Dec. 2014), Deotare Uday et al.,: "Diagnosis of Blastic Plasmacytoid Dendritic Cell Neoplasm by Using 10-Colour Flow Cytometry and Achievement of Remission by Hypercvad Therapy", XP002791197, Database accession No PREV201500276830, abstract. & Deotare et al., (2014) Diagnosis of Blastic Plasmacytoid Dendritic Cell Neoplasm by Using 10-Colour Flow Cytometry and Achievement of Remission by Hypercvad Therapy. Blood 124 (21): 2365.
Autissier et al., (2010) Evaluation of a 12-color flow cytometry panel to study lymphocyte, monocyte, and dendritic cell subsets in humans. Cytometry part A, 77(5), 410-419.
Brooks et al., (2013) Identifying leukocyte populations in fresh and cryopreserved sputum using flow cytometry. Cytometry Part B: Clinical Cytometry, 84(2), 104-113.
Fridman et al., (2012) The immune contexture in human tumours: impact on clinical outcome. Nature Reviews Cancer, 12(4), nrc3245, 298-306.
Galluzzi et al., (2012) The secret ally: immunostimulation by anticancer drugs. Nature reviews Drug discovery, 11(3), 215-233.
Griesinger et al., (2013) Characterization of distinct immunophenotypes across pediatric brain tumor types. The Journal of Immunology, 191(9), 4880-4888.
Griesinger et al., (2014) Immunotherapeutic implications of the immunophenotype of pediatric brain tumors. Oncoimmunology, 3(1), e27256.
Kovacsovics-Bankowski et al., (2014) Detailed characterization of tumor infiltrating lymphocytes in two distinct human solid malignancies show phenotypic similarities. Journal for immunotherapy of cancer, 2(1), 38.
Lamoreaux et al., (2006) Intracellular cytokine optimization and standard operating procedure. Nature protocols, 1 (3), 1507-1516.
Maecker et al., (2008) Selecting reagents for multicolor flow cytometry with BD™ LSR II and BD FACSCanto™ systems. Nature Methods, 5(12), an6-an7.
Misharin et al., (2013) Flow cytometric analysis of macrophages and dendritic cell subsets in the mouse lung. American journal of respiratory cell and molecular biology, 49(4), 503-510.
Perfetto et al., (2004) Seventeen-colour flow cytometry: unravelling the immune system. Nature Reviews Immunology, 4(8), 648-655.
Van Dongen et al., (2012) EuroFlow: Resetting leukemia and lymphoma immunophenotyping. Basis for companion diagnostics and personalized medicine. Leukemia 2012; 26, 1899-1907.
Volovitz et al., (2011) Split immunity: immune inhibition of rat gliomas by subcutaneous exposure to unmodified live tumor cells. The Journal of Immunology, 187(10), 5452-5462.
Volovitz et al., (2016) A non-aggressive, highly efficient, enzymatic method for dissociation of human brain-tumors and brain-tissues to viable single-cells. BMC neuroscience, 17(1), 30, 1-10.
Volovitz et al., (2016) Dendritic cells in the context of human tumors: biology and experimental tools. International reviews of immunology, 35(2), 116-135.

\* cited by examiner

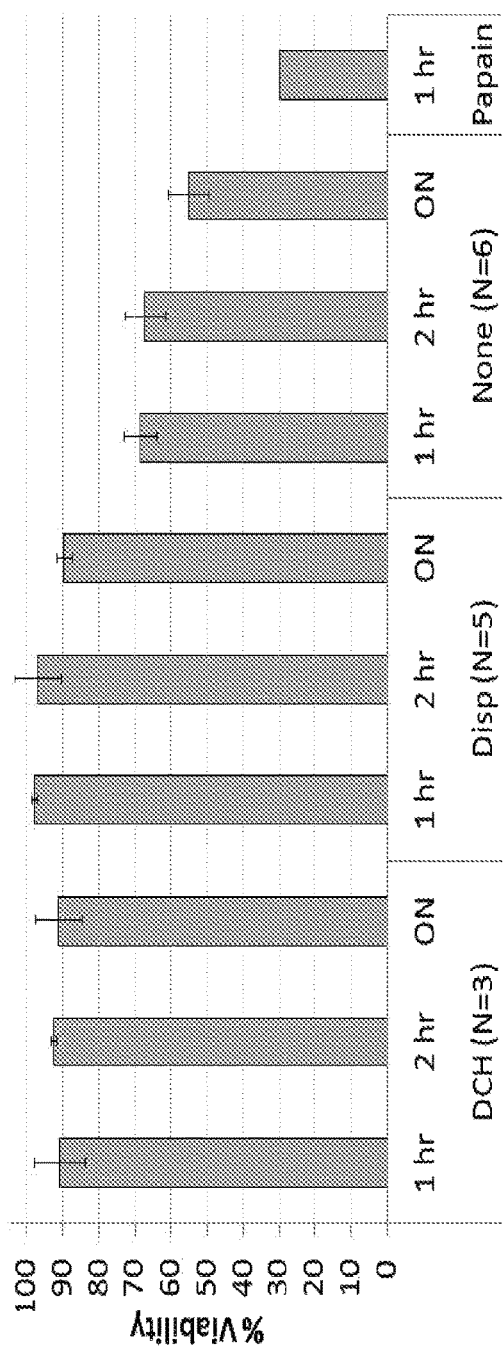
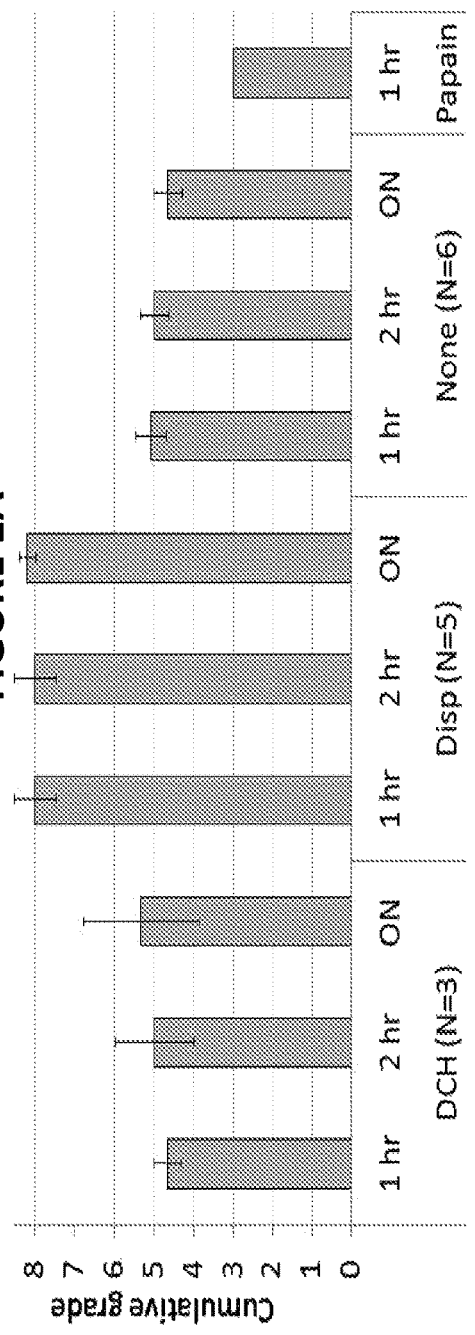
FIGURE 1A
FIGURE 1B

FIGURE 12B

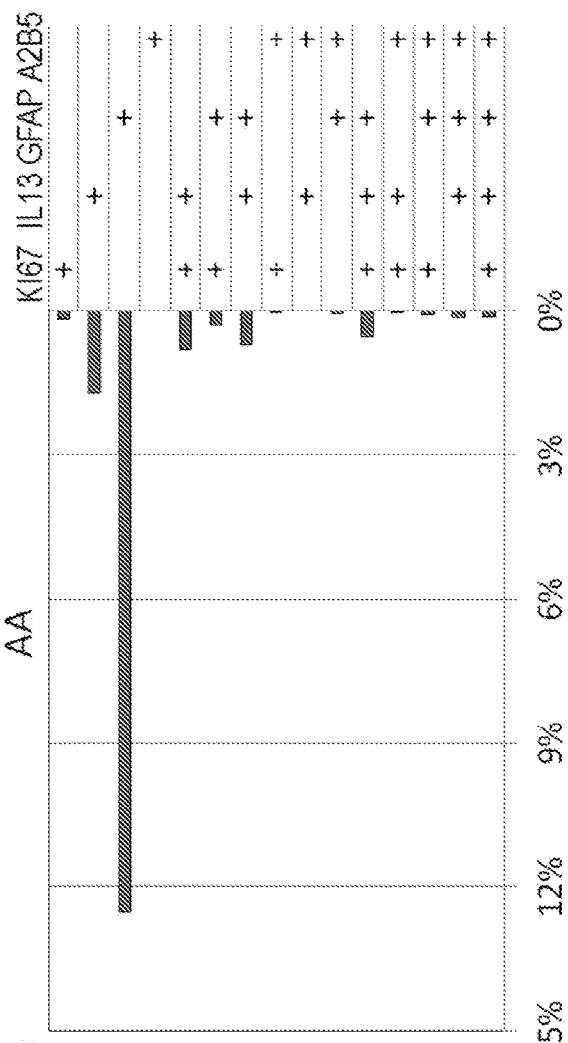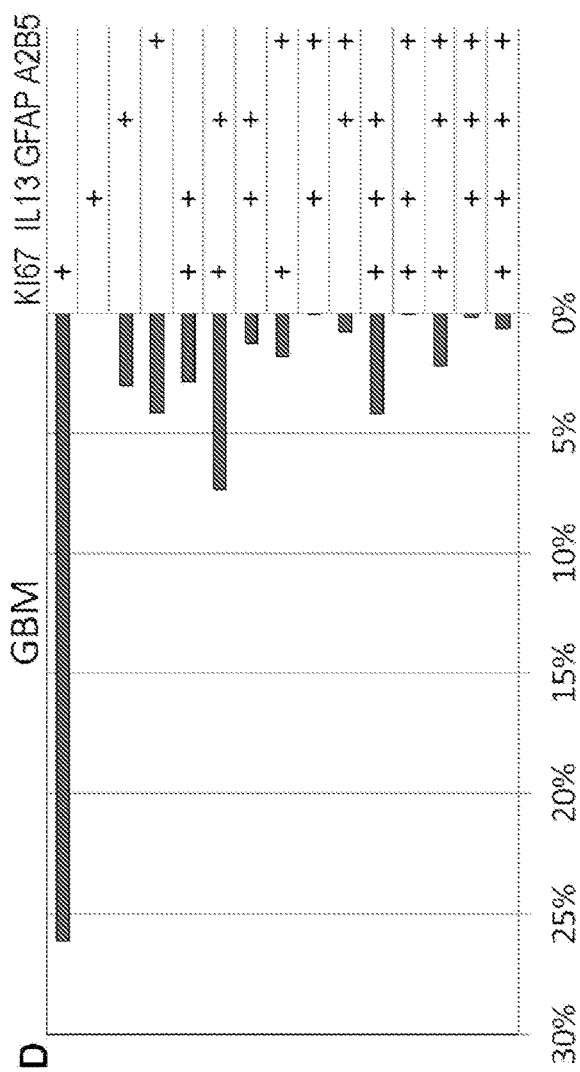
FIGURE 13C
FIGURE 13D

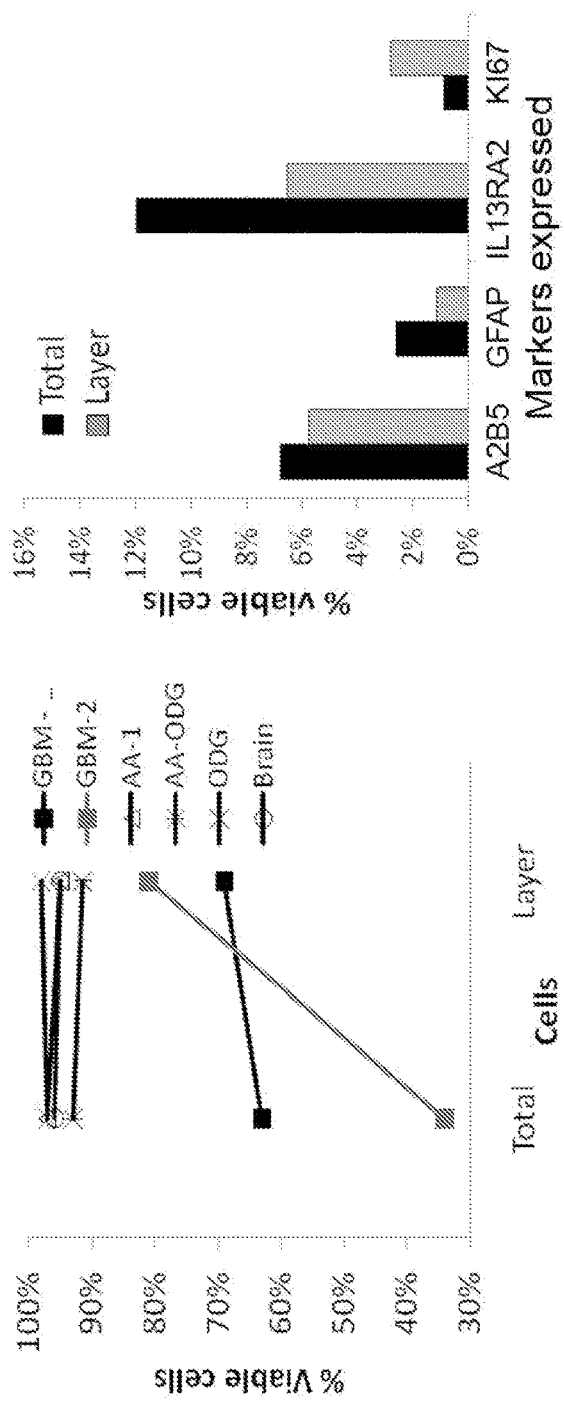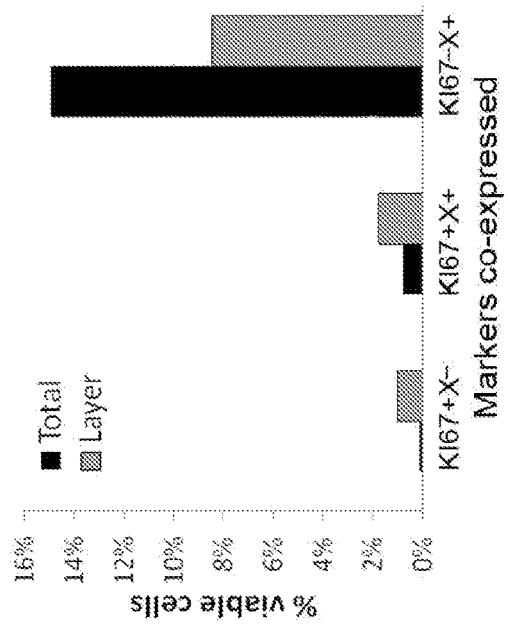
FIGURE 14A
FIGURE 14B
FIGURE 14C

SEQUENCE LISTING

```
<160> NUMBER OF SEQ ID NOS: 34

<210> SEQ ID NO 1
<211> LENGTH: 20
<212> TYPE: DNA
<213> ORGANISM: Artificial
<220> FEATURE:
<223> OTHER INFORMATION: PCR primer

<400> SEQUENCE: 1
ggtgctgcta gtctgggtcc                                              20

<210> SEQ ID NO 2
<211> LENGTH: 21
<212> TYPE: DNA
<213> ORGANISM: Artificial
<220> FEATURE:
<223> OTHER INFORMATION: PCR primer

<400> SEQUENCE: 2
ggaaatccag ctccccatag t                                            21

<210> SEQ ID NO 3
<211> LENGTH: 18
<212> TYPE: DNA
<213> ORGANISM: Artificial
<220> FEATURE:
<223> OTHER INFORMATION: PCR primer

<400> SEQUENCE: 3
gggcatttgc tgaacgca                                                18

<210> SEQ ID NO 4
<211> LENGTH: 20
<212> TYPE: DNA
```

```
<213> ORGANISM: Artificial
<220> FEATURE:
<223> OTHER INFORMATION: PCR primer

<400> SEQUENCE: 4
gccaattagt gcagccaggt                                           20

<210> SEQ ID NO 5
<211> LENGTH: 21
<212> TYPE: DNA
<213> ORGANISM: Artificial
<220> FEATURE:
<223> OTHER INFORMATION: PCR primer

<400> SEQUENCE: 5
tccaaggatg cttaccacca g                                         21

<210> SEQ ID NO 6
<211> LENGTH: 25
<212> TYPE: DNA
<213> ORGANISM: Artificial
<220> FEATURE:
<223> OTHER INFORMATION: PCR primer

<400> SEQUENCE: 6
gccaatgtgg atatttgtgt tagat                                     25

<210> SEQ ID NO 7
<211> LENGTH: 21
<212> TYPE: DNA
<213> ORGANISM: Artificial
<220> FEATURE:
<223> OTHER INFORMATION: PCR primer

<400> SEQUENCE: 7
cctttcatca ccaccattct g                                         21

<210> SEQ ID NO 8
<211> LENGTH: 21
<212> TYPE: DNA
<213> ORGANISM: Artificial
<220> FEATURE:
<223> OTHER INFORMATION: PCR primer

<400> SEQUENCE: 8
atgtggaacc tctgagcact g                                         21

<210> SEQ ID NO 9
<211> LENGTH: 21
<212> TYPE: DNA
<213> ORGANISM: Artificial
<220> FEATURE:
<223> OTHER INFORMATION: PCR primer

<400> SEQUENCE: 9
gagtagtggc cctggttgct c                                         21

<210> SEQ ID NO 10
<211> LENGTH: 17
<212> TYPE: DNA
<213> ORGANISM: Artificial
<220> FEATURE:
<223> OTHER INFORMATION: PCR primer

<400> SEQUENCE: 10
cgctggtcgc ttgccct                                              17
```

<210> SEQ ID NO 11
<211> LENGTH: 20
<212> TYPE: DNA
<213> ORGANISM: Artificial
<220> FEATURE:
<223> OTHER INFORMATION: PCR primer

<400> SEQUENCE: 11
tcactgttct gggtctggag                                               20

<210> SEQ ID NO 12
<211> LENGTH: 20
<212> TYPE: DNA
<213> ORGANISM: Artificial
<220> FEATURE:
<223> OTHER INFORMATION: PCR primer

<400> SEQUENCE: 12
cacttggcag tgaggaaaga                                               20

<210> SEQ ID NO 13
<211> LENGTH: 21
<212> TYPE: DNA
<213> ORGANISM: Artificial
<220> FEATURE:
<223> OTHER INFORMATION: PCR primer

<400> SEQUENCE: 13
ttttcgctcc atgatgcgtt a                                             21

<210> SEQ ID NO 14
<211> LENGTH: 19
<212> TYPE: DNA
<213> ORGANISM: Artificial
<220> FEATURE:
<223> OTHER INFORMATION: PCR primer

<400> SEQUENCE: 14
gcctgtccag gataagccc                                                19

<210> SEQ ID NO 15
<211> LENGTH: 20
<212> TYPE: DNA
<213> ORGANISM: Artificial
<220> FEATURE:
<223> OTHER INFORMATION: PCR primer

<400> SEQUENCE: 15
ggacaaagcc aacctggaaa                                               20

<210> SEQ ID NO 16
<211> LENGTH: 20
<212> TYPE: DNA
<213> ORGANISM: Artificial
<220> FEATURE:
<223> OTHER INFORMATION: PCR primer

<400> SEQUENCE: 16
aggacgttgg gctctctcag                                               20

<210> SEQ ID NO 17
<211> LENGTH: 22
<212> TYPE: DNA
<213> ORGANISM: Artificial
<220> FEATURE:

<223> OTHER INFORMATION: PCR primer

<400> SEQUENCE: 17
gggcaccatt gaaatcctga gt                                              22

<210> SEQ ID NO 18
<211> LENGTH: 20
<212> TYPE: DNA
<213> ORGANISM: Artificial
<220> FEATURE:
<223> OTHER INFORMATION: PCR primer

<400> SEQUENCE: 18
atgttcagca gcgtggcttc                                                 20

<210> SEQ ID NO 19
<211> LENGTH: 20
<212> TYPE: DNA
<213> ORGANISM: Artificial
<220> FEATURE:
<223> OTHER INFORMATION: PCR primer

<400> SEQUENCE: 19
cctcctgttc gacagtcagc                                                 20

<210> SEQ ID NO 20
<211> LENGTH: 20
<212> TYPE: DNA
<213> ORGANISM: Artificial
<220> FEATURE:
<223> OTHER INFORMATION: PCR primer

<400> SEQUENCE: 20
gttaaaagca gccctggtga                                                 20

<210> SEQ ID NO 21
<211> LENGTH: 20
<212> TYPE: DNA
<213> ORGANISM: Artificial
<220> FEATURE:
<223> OTHER INFORMATION: PCR primer

<400> SEQUENCE: 21
tgacactggc aaaacaatgc                                                 20

<210> SEQ ID NO 22
<211> LENGTH: 20
<212> TYPE: DNA
<213> ORGANISM: Artificial
<220> FEATURE:
<223> OTHER INFORMATION: PCR primer

<400> SEQUENCE: 22
aacacttcgt ggggtccttt                                                 20

<210> SEQ ID NO 23
<211> LENGTH: 20
<212> TYPE: DNA
<213> ORGANISM: Artificial
<220> FEATURE:
<223> OTHER INFORMATION: PCR primer

<400> SEQUENCE: 23
ccaacccaga ctatgagccc                                                 20

```
<210> SEQ ID NO 24
<211> LENGTH: 20
<212> TYPE: DNA
<213> ORGANISM: Artificial
<220> FEATURE:
<223> OTHER INFORMATION: PCR primer

<400> SEQUENCE: 24
gcagtgttct ccagagggtc                                              20

<210> SEQ ID NO 25
<211> LENGTH: 20
<212> TYPE: DNA
<213> ORGANISM: Artificial
<220> FEATURE:
<223> OTHER INFORMATION: PCR primer

<400> SEQUENCE: 25
cagcagcaga ctctcccaaa                                              20

<210> SEQ ID NO 26
<211> LENGTH: 20
<212> TYPE: DNA
<213> ORGANISM: Artificial
<220> FEATURE:
<223> OTHER INFORMATION: PCR primer

<400> SEQUENCE: 26
cctggcaaca gatggtcact                                              20

<210> SEQ ID NO 27
<211> LENGTH: 20
<212> TYPE: DNA
<213> ORGANISM: Artificial
<220> FEATURE:
<223> OTHER INFORMATION: PCR primer

<400> SEQUENCE: 27
agcgcacacg ggaagatatc                                              20

<210> SEQ ID NO 28
<211> LENGTH: 22
<212> TYPE: DNA
<213> ORGANISM: Artificial
<220> FEATURE:
<223> OTHER INFORMATION: PCR primer

<400> SEQUENCE: 28
ggtgcctgct taaatggaga tc                                           22

<210> SEQ ID NO 29
<211> LENGTH: 20
<212> TYPE: DNA
<213> ORGANISM: Artificial
<220> FEATURE:
<223> OTHER INFORMATION: PCR primer

<400> SEQUENCE: 29
acagccaatg tgagcagtga                                              20

<210> SEQ ID NO 30
<211> LENGTH: 20
<212> TYPE: DNA
<213> ORGANISM: Artificial
<220> FEATURE:
<223> OTHER INFORMATION: PCR primer
```

```
-continued

<400> SEQUENCE: 30
ttgttcgtgg ctgctaacca                                              20

<210> SEQ ID NO 31
<211> LENGTH: 22
<212> TYPE: DNA
<213> ORGANISM: Artificial
<220> FEATURE:
<223> OTHER INFORMATION: PCR primer

<400> SEQUENCE: 31
gaagacttat cgaccatgga gc                                           22

<210> SEQ ID NO 32
<211> LENGTH: 20
<212> TYPE: DNA
<213> ORGANISM: Artificial
<220> FEATURE:
<223> OTHER INFORMATION: PCR primer

<400> SEQUENCE: 32
agacgcagcg gaaatcttca                                              20

<210> SEQ ID NO 33
<211> LENGTH: 20
<212> TYPE: DNA
<213> ORGANISM: Artificial
<220> FEATURE:
<223> OTHER INFORMATION: PCR primer

<400> SEQUENCE: 33
ttctcctggc ctctcagcta                                              20

<210> SEQ ID NO 34
<211> LENGTH: 22
<212> TYPE: DNA
<213> ORGANISM: Artificial
<220> FEATURE:
<223> OTHER INFORMATION: PCR primer

<400> SEQUENCE: 34
caactgtctg ccagtcttct tg                                           22
```

CYTOMETRIC ASSAYS

SEQUENCE LISTING

The Sequence Listing submitted in text format (.txt) filed on May 31, 2018, named "SequenceListing.txt", created on May 29, 2018 (6.19 KB), is incorporated herein by reference.

FIELD OF THE INVENTION

The invention relates to the field of cytometry, specifically to flow cytometric assays for improved tumor immunophenotyping, prognosis and immune modeling.

BACKGROUND OF THE INVENTION

Immune therapies to cancer, as well as many non-immune cancer therapies (such as photodynamic therapy irradiation, and various chemotherapeutics), induce a complex immune response that may facilitate the systemic rejection of tumor cells. These immune-inducing therapies are emerging as a highly effective means to treat cancers of various tissues. However, the outcome of such therapies is highly dependent on the host's immune status, and particularly on the nature and quantity of resident or infiltrating immune cells (also referred to as tumor-infiltrating leukocytes, or TIL) present within the tumor environment.

For example, different TIL populations may induce either beneficial immune responses capable of attacking the tumor cells, or detrimental tolerogenic responses, having a suppressive effect on the tumor-attacking TIL. Quantification and characterization of the various TIL populations, including rare populations such as dendritic cell (DC) subtypes, is often challenging. In particular, accurate immune phenotyping of solid tumors characterized by low TIL counts (such as in brain tumors), has not yet been established in standard patient management. Consequently, the patients may be administered with ineffective therapies that waste the time of their therapeutic window, and even with potentially harmful therapies.

In addition, immunophenotyping is emerging as a potential diagnostic and prognostic tool, as certain TIL populations have been correlated with tumor grade and overall survival in various tumor types (Fridman et al., 2012). Better understanding and accurate characterization of TIL populations and sub-populations, their activation state, relative proportions within the tumor environment and interactions with different cells and environmental factors, would thus be highly valuable (Galluzzi, et al., 2012).

Various experimental methods for the determination of the properties of cells (cytometry) have been developed. For example, Cytometry by Time of Flight (CyToF) is a flow cytometric method that is coupled with mass spectrometry technique. In this approach, antibodies are tagged with isotopically pure rare earth elements and these antibodies are used to tag the components of cells. Cells are nebulized and sent to an argon plasma, ionizing the multi-atom metal tags, which are then analyzed by a time-of-flight mass spectrometer. The approach overcomes limitations of spectral overlap that limit other assays such as flow cytometry (FCM). For example, CyTOF was reported to allow the phenotypic and functional characterization of e.g. human $CD8^+$ T cells by measuring various cell surface markers, cytokines, cytotoxic granule components and viral antigen peptide-MHC tetramers; the method reportedly distinguished all $CD8^+$ T-cell subsets hitherto described, including naive, central memory, effector memory, terminal effector, long-lived memory precursor effector cells and short-lived effector cells. However, mass cytometry entails the destruction of the examined cells during the process, thus precluding isolation and further examination of the identified cell populations.

Multicolor FCM is a fluorescent light emission-based technology, in which single cells are mobilized through a stream of fluid and passed by a light source that activates any fluorescent antibodies that are bound to the flowing cells. An electronic detection apparatus collects the fluorescent light that correlates with the amount of marker the cell is expressing. FCM allows for a fast and sensitive high-throughput analysis of cells in suspension, enabling their concurrent analysis in terms of phenotype, maturation status and cellular function. Flow cytometric sorting is a specialized type of FCM, providing a method for sorting of selected subset of cells into one or more containers, one cell at a time. The cells are sorted based upon a specifically selected light scattering and/or fluorescent characteristics of each cell. The simultaneous staining for a large number of markers, enabling discrimination between multiple cell populations, involves many technical challenges such as spectral overlap between different fluorochromes and spreading error between fluorochromes, and is limited by the properties (e.g. the number of photomultiplier channels) of currently available FCM sorters.

Multicolor FCM has been applied in the diagnosis of blood cancers and other hematologic pathologies, and various panels for phenotyping and monitoring blood leukocytes have been described. For example, the EuroFlow Consortium was formed in an attempt to develop FCM assays for immunophenotyping hematopoietic malignancies, particularly leukemia and lymphoma (Leukemia 2012; 26, 1899-1907). The EuroFlow project is also described in EP 2438446, which claims a reagent composition for flow cytometric immunophenotyping of leukocytes comprising at least eight distinct fluorochrome-conjugated antibodies comprising a set of at least three identification antibodies for the identification of a leukocyte population of interest and at least four characterization antibodies for further characterization and/or classification of said leukocyte population, wherein the antibodies are directed against one of the following combinations of markers: CD20, CD4, CD45, CD19, Igλ, CD8, Igκ, CD56, TCRγδ, CD3 and CD38, wherein the antibody within either one of the pairs CD20/CD4, Igλ/CD8 and CD19/TCRγδ is conjugated to the same fluorochrome and wherein between different pairs the fluorochromes are distinguishable.

Additional FCM panels for blood leukocytes were described, for example, by Autissier et al. (Cytometry Part A, 77A: 410-419, 2010). The study disclosed a 12-color FCM panel for studying the immune response during HIV infection, capable of identifying certain major subsets of blood-circulating cells. The following markers were assayed: CD16, CD141, CD34, CD11c, CD123, CD20, CD56, CD1c, CD3, HLA-DR, CD14, CD4 and CD8, wherein the exclusion markers (i.e. markers which are not supposed to be expressed by certain cells) were detected separately in different fluorescent channels, and no viability marker was used.

However, characterization of dissociated tissue samples presents technical and scientific challenges that are not encountered when analyzing blood-derived samples. For example, available methods often fail to provide gentle yet effective dissociation of the tissue sufficient to enable most or all immune cells to be freed from the extracellular matrix while maintaining their viability. Additionally, non-immune cells in the tissue may express markers that are also found in immune cells, thereby providing additional challenges for correct identification and isolation of immune subsets. For example, various brain cells highly expresses CD56, a glycoprotein expressed on the surface of neurons, glia, and skeletal muscle that is also expressed on natural killer (NK) cells and NK-T cells. Additionally certain tissues such as tumors may be highly autofluorescent, creating a very wide cell cloud hindering the identification of small cellular subsets or subsets identified using weakly staining markers (e.g. CD56 is an important NK marker but is expressed in low numbers on the surface of NK cells). Recent publications to Griesinger et al. (J Immunol. 2013 Nov. 1; 191(9); Oncoimmunology. 2014; 3: e27256) report the characterization of distinct immunophenotypes across pediatric brain tumor types, and discuss the immunotherapeutic implications of the immunophenotype of pediatric brain tumors. The characterization was performed using a low-resolution semi-quantitative FCM assay on mechanically separated tumor cells. The assay was designed to target the following surface markers using a number of small panels: CD45 and CD11b for total myeloid cells, HLA-DR and CD64 Fcγ-R for activated myeloid cells, scavenger receptor CD163 and mannose receptor CD206 for suppressed inflammatory or alternatively activated M2 myeloid phenotype, CD50 (ICAM-3) for undifferentiated or immature myeloid cells, CD45 and CD3 for tumor-infiltrating lymphocytes, CD4 and CD8 to distinguish Th-cells and CTL respectively, CD45RO for effector memory T-cells, and programmed cell death protein 1 (PD-1, CD279) for inhibitory T-cell activity.

There remains an unmet need for improved cytometric assays, allowing simultaneous high resolution identification and optional isolation of all prominent cell populations within a defined environment such as a solid tumor or other solid tissues. The development of experimental tools for accurate identification, quantification and profiling of multiple cell types would be highly beneficial for experimental and clinical purposes alike.

SUMMARY OF THE INVENTION

The invention relates to cytometry, specifically to assays providing improved tumor diagnosis, immune monitoring and disease prognosis, and enabling the identification and selection of effective tumor-specific therapies, using multicolor/multiparametric flow cytometry. More specifically, embodiments of the invention provide high resolution quantitative methods, reagents and kits useful for immunophenotyping and cytomic modeling.

The invention is based, in part, on the discovery of surprisingly informative cytometric panels comprising unique combinations of antibodies, and of fluorophore markers. The invention is further based in part, on the identification of advantageous methods utilizing these panels in combination with unexpectedly improved sample preparation steps and ordered detection and analysis steps, providing highly sensitive, reliable and quantitative separation and characterization of cell populations. Advantageously, sample preparation using Neutral Protease (NP) from *Clostridium histolyticum* (Ch) yielded dissociated cell mixtures with exceptionally high viability and quality.

The assays were found to be capable of identifying and quantifying all prominent immune cells found inside brain lesions (primary brain tumors, metastasis of non-brain tumors to the brain, and non-tumorous brain tissue) notably discriminating between human microglia and macrophage populations and identifying other rare cell populations, including populations that could not be identified correctly in solid tissues (e.g. tumors) by currently available flow cytometric tools. The following cell populations were identified using 7 or 8-color flow cytometry assays: cytotoxic T lymphocytes (CTLs), helper T cells (Th), CD4$^-$CD8$^-$CD3$^+$ γ/δ T cells, CD56$^+$ natural killer (NK) cells, NK-T cells of two subtypes (Type1—iNKT:Va24Jα18$^+$, and Type 2-NKT lacking the V$\alpha_{24}$J$\alpha_{18}$ T cell receptor (TcR)), neutrophils, eosinophils, macrophages (activated-M1-like, and alternatively activated-M2-like), microglia (activated and non-activated), CD16$^+$ NK cells, plasmacytoid dendritic cells (DC) and myeloid DC (mDC) of three subtypes (mDC-1 (CD1c$^+$), mDC2 (CD141$^+$), and mDC-CD16$^+$).

Using the newly developed assays, distinct immune profiles were identified in brain tumor lesions, epileptic brain lesions and healthy samples. By correlating progression free survival (PFS) or overall survival (OS) with the specific frequencies of the different cell subsets and relationships between the quantities of these subsets, these profiles were surprisingly found to have disease prognostic power, and to be correlated with disease grade, thus serving a diagnostic role. In addition, the assays and methods developed enabled the collection of reliable gene expression patterns for each of the infiltrating immune cell populations, thereby enabling improved means for predicting and monitoring treatment efficacy in cancer patients, and providing for effective patient-specific (or personalized) cancer immunotherapy.

In addition, unexpectedly advantageous cytometric panels and methods were identified for classifying and quantifying human brain tumor cells. These assays were capable of differentiating between brain pathologies including low and high grade astrocytomas, epileptic lesions, and peripheral (non-central nervous system (CNS)) tumor metastasis to the brain, using as few as five fluorescent markers. The assays also enabled quantification of the fraction of live tumor cells following single-cell tissue dissociation and following a tumor-cell purification step using a density gradient, and revealed clinically-relevant information on marker co-expression in gliomas.

Thus, the cytometric panels, reagents, kits and methods, collectively referred to herein as the assays of the invention, surprisingly provide for highly accurate and informative separation of cell populations using minimal marker combinations.

According to a first aspect of the invention, there is provided a cytometric kit comprising a viability dye and a plurality of labeled antibodies. In another embodiment, the kit is useful for characterizing multiple cell populations in a human tissue sample (dissociated from solid tissues). In various embodiments, the cytometric kit comprises at least one and advantageously a plurality of cytometric panels, namely sets of labeled antibodies useful for simultaneous identification and characterization of a plurality of cell within a given sample. According to advantageous embodiments, highly accurate identification and characterization of a plurality of lymphocyte, innate cell, DC and optionally tumor cell populations as disclosed herein is surprisingly enabled using as few as 1-3 simultaneous labeling and measurement steps.

Thus, according to some embodiments, provided is a kit for characterizing cell populations in a human tissue sample, comprising a fluorescent viability dye and fluorophore-labeled antibodies directed to human cellular targets comprising: CD45, CD3, CD4, CD8, CD14, CD16, CD141, CD1c, CD56, at least one of CD123, CD303 and CD304, at least one of TcR-Vα24Jα18, CD19 and CD20, and optionally at least one of CD11b, HLA-DR, CD33, CD66b and TcRγ/δ, wherein the kit comprises at least one cytometric panel comprising distinct fluorophore-labeled antibodies directed to human CD45 and at least five additional targets of said human cellular targets.

Distinct fluorophore-labeled labeled antibodies within a panel of the invention are labeled with distinct (non-equivalent) fluorophores, enabling the separation of cells bound by said antibodies (e.g. by flow cytometry) in a single measurement step. The panel may optionally comprise lineage-specific antibodies enabling exclusion of non-related cell populations which are typically labeled by the same (or substantially equivalent) fluorophore, more typically with the same or a substantially equivalent fluorophore as the fluorescent viability dye.

In various embodiments, the labeled antibodies are directed to at least 5-8 distinct cellular targets selected from the group consisting of CD3, CD4, CD8, CD56, TcR-Vα24Jα18, CD45, CD11b, CD14, CD19, CD20, CD14, HLA-DR, CD33, CD16, CD66b, CD1c, CD141, CD123 and CD303. Each possibility represents a separate embodiment of the invention. In certain embodiments, the kit comprises a plurality of cytometric panels, each panel comprising a viability dye and a plurality (e.g. 5-8 or more) of antibodies directed to distinct cellular targets as detailed herein. Typically and conveniently, the antibodies used in the methods and kits of the invention are monoclonal or polyclonal antibodies directed to a cellular target of interest and conjugated to fluorophore markers.

In one embodiment, the kit is useful for identifying lymphocyte populations, and comprises a cytometric panel (referred to herein as a cytometric panel for identifying lymphocyte populations or a lymphocyte panel) comprising a viability dye and distinct fluorophore-labeled antibodies directed to human CD45, CD3, CD4, CD8, CD56 and optionally CD11b and to at least one of TcR-Vα24Jα18, CD19 and CD20, and a plurality of lineage-specific antibodies, comprising: at least one antibody directed to a human monocyte/macrophage cellular target and at least one antibody directed to a human granulocyte cellular target, wherein if said panel comprises an antibody directed to TcR-Vα24Jα18, said lineage-specific antibodies further comprise at least one antibody directed to a human B-cell cellular target. In a particular embodiment, the cytometric panel comprises:
i) an antibody directed to CD45, conjugated to Allophycocyanin (APC) or a substantially equivalent fluorophore (in terms of fluorescence yield or staining index, and typically also maximal emission (Em) wavelength, e.g. Alexa Fluor 647);
ii) an antibody directed to CD11b or TcRγ/δ, conjugated to Alexa Fluor® 488 or a substantially equivalent fluorophore (e.g. FITC);
iii) an antibody directed to CD3, conjugated to APC-H7 or a substantially equivalent fluorophore (e.g. APC-eFluor 780 or APC-Alexa fluor 750);
iv) an antibody directed to CD4, conjugated to PE-Cy5.5 or PerCP-Cy5.5 or a substantially equivalent fluorophore;
v) an antibody directed to CD8, conjugated to QD655 or a substantially equivalent fluorophore (e.g. Brilliant violet (BV) 650 or eVolve 655);
vi) an antibody directed to CD56, conjugated to PE-Cy7 or a substantially equivalent fluorophore;
vii) at least one antibody directed to one of TcR-Vα24Jα18, CD19 or CD20, conjugated to PE or a substantially equivalent fluorophore;
viii) ViViD (violet viability dye) or a substantially equivalent viability dye; and
ix) a plurality of fluorophore-conjugated lineage-specific antibodies, comprising: at least one antibody directed to a human monocyte/macrophage cellular target (e.g. CD14) and at least one antibody directed to a human granulocyte cellular target, wherein if said panel comprises an antibody directed to TcR-Vα24Jα18, said lineage-specific antibodies further comprise at least one antibody directed to a human B-cell cellular target;
wherein the lineage specific antibodies are preferably conjugated to the same fluorophore, more preferably to a fluorophore that is substantially equivalent (at least in terms of maximal emission wavelength) to the viability dye, e.g. Pacific Blue (Pac-bl) or brilliant violet 421 (BV421). PacBl, or substantially equivalent fluorophore may thus be used to stain all unwarranted cell subsets, wherein the viability dye has similar emission maximum as that of PacBl. For example, according to advantageous embodiments, the monocyte/macrophage cellular target is CD14, the B cell cellular target is CD19 or CD20 and the granulocyte cellular target is CD66b, and the plurality of lineage-specific antibodies are conjugated to Pac-bl, wherein each possibility represents a separate embodiment of the invention.

In another embodiment, the kit is useful for identifying innate immune cell populations, and comprises a cytometric panel (referred to herein as a cytometric panel for identifying innate immune cell populations or an innate panel) comprising a viability dye and distinct fluorophore-labeled antibodies directed to human CD45, CD11b, CD14, HLA-DR, CD16, CD33 and optionally CD66b. In a particular embodiment, the cytometric panel comprises:
i) an antibody directed to human CD45, conjugated to APC or a substantially equivalent fluorophore;
ii) an antibody directed to human CD11b, conjugated to Alexa Fluor® 488 or a substantially equivalent fluorophore;
iii) an antibody directed to human CD14, conjugated to QD655 or a substantially equivalent fluorophore (e.g. BV650);
iv) an antibody directed to human HLA-DR, conjugated to APC eflour-780 or a substantially equivalent fluorophore;
v) an antibody directed to human CD16, conjugated to PE or a substantially equivalent fluorophore;
vi) an antibody directed to human CD33, conjugated to PerCp-Cy5.5 or a substantially equivalent fluorophore (e.g. PE Cy5.5);
vii) optionally an antibody directed to human CD66b conjugated to V450 or a substantially equivalent fluorophore (e.g. BV421); and
viii) ViViD violet or a substantially equivalent viability dye.

In another embodiment, the kit is useful for identifying DC populations, and comprises a cytometric panel (referred to herein as a cytometric panel for identifying DC populations or a DC panel) comprising a viability dye and distinct fluorophore-labeled antibodies directed to CD45, CD14, HLA-DR, CD1c, CD141 and CD16, and to at least one of CD123, CD303 and CD304, and a plurality of lineage-specific antibodies comprising at least one antibody directed to a human T cell cellular target, at least one antibody directed to a human B cell cellular target and at least one antibody directed to a human granulocyte cellular target. In a particular embodiment, the cytometric panel comprises:
i) an antibody directed to human CD45, conjugated to APC or a substantially equivalent fluorophore;
ii) an antibody directed to human CD14, conjugated to BV650 or a substantially equivalent fluorophore;
iii) an antibody directed to human HLA-DR, conjugated to APC eflour 780 or a substantially equivalent fluorophore;

iv) an antibody directed to human CD1c, conjugated to Pe-cy7 or a substantially equivalent fluorophore;
v) an antibody directed to human CD141, conjugated to PE or a substantially equivalent fluorophore;
vi) an antibody directed to human CD16, conjugated to PerCp-Cy5.5 or a substantially equivalent fluorophore;
vii) at least one antibody directed to human CD123, CD303 or CD304 conjugated to FITC or a substantially equivalent fluorophore;
viii) ViViD violet or a substantially equivalent amine viability dye; and
x) a plurality of fluorophore-conjugated lineage-specific antibodies comprising at least one antibody directed to a human T cell cellular target, at least one antibody directed to a human B cell cellular target and at least one antibody directed to a human granulocyte cellular target;

wherein the lineage specific antibodies are preferably conjugated to the same fluorophore, more preferably to a fluorophore that is substantially equivalent to the viability dye, e.g. Pac-bl. For example, according to advantageous embodiments, the T cell cellular target is CD3, the B cell cellular target is CD19 or CD20 and the granulocyte cellular target is CD66b or CD15, and the plurality of lineage-specific antibodies are conjugated to Pac-bl, wherein each possibility represents a separate embodiment of the invention.

In another embodiment, the kit is useful for identifying brain tumor cell populations, and comprises a cytometric panel (referred to herein as a glioma specific panel) comprising a viability dye and antibodies directed to a proliferation marker such as Ki67, a glial cell marker such as GFAP, and at least two glioma-associated antigens (GAA) selected from the group consisting of: IL13 receptor α2 (IL13Rα2), CD133, EGFR, CD24, CD44, transferrin-R and IL-4R and A2B5. In a particular embodiment the cytometric panel comprises antibodies directed to human Ki67, GFAP, IL13Rα2, and A2B5, wherein the antibodies are directly or indirectly labeled with distinct fluorophores, and an amine viability dye. In another embodiment the kit further comprises a cytometric panel comprising: a fluorescent viability dye and distinct fluorophore-labeled antibodies directed to human Ki67, GFAP, IL13Rα2, and A2B5. According to particular embodiments, the antibody directed to Ki67 is directly or indirectly labeled by PE-CY7 or a substantially equivalent fluorophore, the antibody directed to GFAP is directly or indirectly labeled by Alexa fluor 647 or a substantially equivalent fluorophore, the antibody directed to A2B5 is directly or indirectly labeled by PE or a substantially equivalent fluorophore the antibody directed to IL13Rα2 is directly or indirectly labeled by Alexa Fluor® 488 or a substantially equivalent fluorophore and the amine viability dye is ViViD violet or a substantially equivalent viability dye.

In a particular embodiment, the kit comprises the innate panel as described herein. Preferably, the kit comprises two or more of the cytometric panels as disclosed herein, typically three of said panels or in other embodiments (such as when examining brain tumors) all of the above four panels (lymphocyte, innate cell, DC and glioma-specific panels). In a particular embodiment, said kit comprising the lymphocyte, innate cell and DC panels as disclosed herein, is surprisingly sufficient for enabling clinically compatible characterization of tumor infiltrating immune cell populations. It is to be understood, that two or more panels of the invention may be combined into a single panel, as long as each panel retains a viability dye as described herein. By means of a non-limitative example, a panel combining innate panel antibodies and DC panel antibodies (wherein redundant antibodies may be omitted, such that the panel comprises one distinctly labeled antibody directed to CD45, one distinctly labeled antibody directed to CD14 etc'), may be used with flow cytometers facilitating concurrent measurement and separation of e.g. 18 colors (fluorescent channels collected).

In various embodiments, said kit comprises additional reagents, e.g. reagents for cell separation, tissue dissociation, cell permeabilization (where required), control samples or antibodies, or other reagents for use in flow cytometry. In a particular embodiment the kit further comprises at least one reagent providing enzymatic dissociation of cells from a tissue sample, and/or instructions for use of said kit on an enzymatically dissociated tissue sample. In an advantageous particular embodiment, the reagents comprise *Clostridium histolyticum* Neutral Protease (Ch NP). In another embodiment, said kit advantageously comprises instructions for use of said kit in characterizing cell populations in an enzymatically dissociated solid tumor sample or cerebral tissue sample, wherein the dissociation comprises incubation with Ch NP.

In other aspects, the invention relates to methods for identifying and characterizing cell populations (e.g. immune cell populations) within a biological sample. The methods of the invention allow in various embodiments improved differentiation and characterization of cell populations within the sample. The biological sample may be a cell containing sample, for example a human tissue sample (a dissociated solid tissue such as a tumor biopsy). In a particular embodiment the sample is a tissue sample comprising leukocyte populations (a non-blood sample), such as a non-hematologic tumor sample. According to additional embodiments, the invention relates to methods for characterizing cell populations in a human tissue sample (e.g. cerebral tumors or non-tumorous lesions).

In other embodiments, the methods provide for enhanced separation of cells (e.g. leukocytes) obtained from tissue samples or other samples in which the relative proportion of leukocyte cells is low, or in cases where certain cell types are absent (e.g. in a tumor sample). According to advantageous embodiments, gating parameters for cell separation are defined according to the properties of leukocyte populations found in blood, preferably in a blood sample obtained from the same subject. Accordingly, in another embodiment, the methods comprise providing a first cell sample and a second cell sample, wherein the first sample is a human tissue sample comprising leukocyte populations of a subject (e.g. a dissociated cell sample obtained from a solid tumor) and the second sample comprises peripheral blood mononuclear cells (PBMC). In various embodiments, the PBMC may be obtained from the subject, or from a healthy donor.

In some embodiments, the methods further comprise dissociating the tissue and isolating cells of the tissue sample (such as tumor cells or tumor-derived immune cells), e.g. by mechanical separation of the tissue and/or enzymatic dissociation. Advantageously, this step is performed by enzymatic dissociation with NP. According to certain preferred embodiments, NP from Ch was surprisingly found to be particularly effective in producing viable isolated cell samples from solid tumors such as gliomas. As disclosed herein, Ch NP produced dissociated cell mixtures with particularly high cellular viability and quality and with significantly less debris compared to all enzymes or enzyme combinations tested. Thus, in another embodiment, the methods further comprise enzymatically dissociating the tissue by incubation with Ch NP so as to produce a cell sample comprising dissociated single cells. For example, without limitation, the tissue may be incubated with Ch NP for 1-2 hours at 37° C., or for 4-12 or 4-18 hours at room temperature. According to certain advantageous embodiments, longer incubation periods at room temperature may be employed, for example, the tissue may be supplemented with culture medium and incubated for e.g. 18-24 hours and up to 48 hours with Ch NP. In another embodiment, the methods comprise enzymatically dissociating the tissue by incubation with Ch NP so as to produce a cell sample comprising dissociated single cells with at least 80% average cell viability.

In another embodiment, there is provided a method for identifying immune cell populations in a human tissue sample, comprising:
a) enzymatically dissociating the tissue so as to produce a dissociated cell sample,
b) incubating the sample, under conditions so as to allow specific antigen-antibody binding, with at least one cytometric panel comprising a fluorescent viability dye and distinct fluorophore-labeled antibodies directed to human CD45 and at least five additional distinct human cellular targets selected from the group consisting of CD45, CD3, CD4, CD8, CD14, CD16, CD141, CD1c, CD56, at least one of CD123, CD303 and CD304, TcR-Vα24Jα18, CD19 CD20, CD11b, HLA-DR, CD33, CD66b and TcRγ/δ, wherein each cytometric panel is incubated with a separate aliquot of said sample.
c) subjecting the sample resulting from step b) to flow cytometry, thereby measuring the fluorescent emission of each fluorophore in said sample, so as to detect specific antigen-antibody binding to at least the following cellular targets: CD45, CD3, CD4, CD8, CD14, CD16, CD141, CD1c, CD56, at least one of CD123, CD303 and CD304, at least one of TcR-Vα24Jα18, CD19 and CD20, and optionally at least one of CD11b, HLA-DR, CD33, CD66b and TcRγ/δ; and
d) analyzing the fluorescent measurements, thereby identifying the cell populations in said sample.

In another embodiment, there is provided a method for characterizing immune cell populations in a human tissue sample, comprising:
a) providing a first human tissue sample comprising leukocyte populations of a subject and a second cell sample comprising PBMC,
b) enzymatically dissociating the tissue so as to produce a cell sample comprising dissociated single cells,
c) incubating each sample, under conditions so as to allow specific antigen-antibody binding, with at least one cytometric panel, each panel comprising a fluorescent viability dye, an antibody directed to CD45 conjugated to APC or a substantially equivalent fluorophore, and fluorophore-conjugated antibodies directed to at least five distinct human cellular targets selected from the group consisting of: CD3, CD4, CD8, CD56, TcR-Vα24Jα18, CD11b, CD14, CD19, CD20, CD14, HLA-DR, CD33, CD16, 6-Sulfo LacNAc, CD66b, CD15, CD1c, CD141, CD123, CD303 and CD304, wherein each cytometric panel is incubated with a separate aliquot of each sample;
d) subjecting each separate aliquot of each sample resulting from step c) to flow cytometry, thereby measuring the fluorescent emission of each fluorophore in each aliquot of each sample,
e) analyzing the fluorescent measurements of each aliquot of each sample, wherein determining the expression of human cellular targets selected from the group consisting of: CD45, CD16, CD66b, CD141, CD123, CD303, CD304, CD3, CD4, CD8, CD56, CD19, CD20 and TcR-Vα24Jα18 comprises comparing the fluorescent measurements of the tissue sample to the respective measurements of the second sample.

In another embodiment enzymatically dissociating the tissue is performed in the methods of the invention by incubation with Ch NP. In another embodiment the cytometric panels in the methods of the invention are selected from the group consisting of the cytometric panels as defined herein.

According to advantageous embodiments, the methods of the invention provide for identification of microglial cells in the sample, and differentiation of human microglial cells from other mononuclear cells such as macrophages. Microglia and macrophages have different and often contradictory or opposing roles, e.g. within a brain tumor environment. Hitherto reported panels do not allow for such separation in human tumor samples altogether, or at most result in macrophage populations that are highly contaminated with neutrophils, eosinophils, activated microglia and NK cells, thus impairing the diagnostic and prognostic value of the assay or its ability to predict suitable treatment for the patient.

In various embodiments, analyzing comprises a series of successive gating steps, in which identification of homogenous subpopulations of cells is performed based on the measured fluorescence intensities or light scatter (forward and/or side scatter) properties, without having to physically separate the sets or subsets of cells (as could be done using cell sorting techniques). In another embodiment the methods comprise defining gating parameters for cell separation according to the properties of PBMC in the second sample, which parameters and gates may subsequently be used to identify the respective leukocyte populations in the first sample and to ensure, as a positive control, that a missing population of cells is missing not due to faulty staining or analysis.

Thus, according to advantageous embodiments, the methods comprise analyzing the fluorescent measurements of each aliquot of the second sample, and comparing fluorescent measurements of each aliquot of the first sample to the measurements of each respective aliquot of the second sample, thereby identifying leukocyte cell populations in the first sample. In a particular embodiment, determining the expression of human cellular targets selected from the group consisting of: CD45, CD16, CD66b, CD141, CD123, CD303, CD304, CD3, CD4, CD8, CD56, CD19, CD20 and TcR-Vα24Jα18 comprises comparing the fluorescent measurements of the tissue sample to the respective measurements of the second sample.

In another embodiment analyzing comprises excluding (gating out) cell aggregates and debris according to the forward scatter and/or side scatter properties of the labeled cells (representing their size and their membrane complexity/granularity, respectively) For instance, gating on forward scatter (FSC) height on FSC width can reveal cell doublets and cell clumps. In another embodiment, analyzing comprises identifying and electing for further analysis (gating in) leukocytes by identifying cells expressing CD45. In another embodiment analyzing advantageously comprises gating in leukocytes by identifying cells expressing CD45 and CD11b. According to some embodiments, the inclusion of two markers (CD45 and CD11b) in both the lymphocytic panel and the innate panel enables easier comparison of the cellular data between these two panels In another embodiment analyzing comprises gating out dead cells identified by the viability dye. For example, in embodiments of the invention, dead cells in a sample labeled by a viability dye such as a dye of the fixable amine viability dye series, distinction between higher and lower fluorescing cell, allows for exclusion (gating out) of the higher fluorescing dead cells. In another embodiment, analyzing comprises gating out cell populations of unwanted lineages, by determining the expression of lineage-specific markers. For example, when identifying lymphocyte cell populations using a lymphocyte panel, other cell lineages such as granulocytes and monocytes are typically excluded. Conveniently, exclusion of several and preferably all unwanted cell lineages is performed in a single step, when the antibodies directed to the various lineage-specific markers are linked to a fluorophore fluorescing on the same detector as the other unwarranted markers.

Thus, in another embodiment of the methods of the invention, analyzing the fluorescent measurements of each aliquot comprises the steps of:
i) excluding from further analysis cell aggregates and debris according to the forward scatter and/or side scatter properties of the cells;
ii) identifying and electing for further analysis CD45-expressing leukocytes;
iii) excluding from further analysis dead cells identified by the viability dye; and
iv) identifying leukocyte cell populations according to the fluorescent measurements of each fluorophore.

For example, in some embodiments, step iv) may comprise the steps of:
iv-a) analyzing the cells for CD45 and CD11b expression, thereby excluding lymphocytes from further analysis (lymphocyte subsets expressing high levels of CD45 and medium to low levels of CD11 b relative to other cell populations, see Table 8);
iv-b) analyzing the cells for CD33 and CD11b expression, thereby identifying and then excluding from further analysis granulocytes such as neutrophils (expressing high levels of both markers, see Table 8); and
iv-c) analyzing the remaining cells for CD14 and CD16 expression, thereby identifying macrophage and microglia cell populations.

In another embodiment, the methods further comprise quantifying the leukocyte cell populations in the samples (e.g. in the first sample). In contradistinction from hitherto disclosed assays, offering non-quantitative or semi-quantitative evaluation of cell populations (such as the Griesinger publications), the invention advantageously provides fully quantitative assays. The ability to provide quantitative and reliable estimation of cell counts of the various lineages entails enhanced diagnostic and prognostic value. For example, the presence of large CD16$^+$ NK cell populations in brain tumors is demonstrated herein to be correlated with increased patient survival.

In another embodiment, the methods further comprise sorting and isolating the cell populations identified. For example, the methods may comprise sorting and isolating a plurality of and preferably all of the following cell populations: CTLs, Th cells, CD56$^+$ NK cells, Type1—iNKT cells, Type 2-NKT cells, neutrophils, eosinophils, activated-M1 macrophages, alternatively activated-M2 macrophages, activated and non-activated microglia, CD16$^+$ NK cells, pDC, mDC-1 (CD1C$^+$), mDC2 (CD141$^+$), mDC-CD16$^+$, and gamma/delta T cells. In a particular embodiment the methods comprise sorting and isolating at least the following populations: Th cells, CTLs, B cells, mDC1, mDC2, pDC, CD16$^+$DC, macrophages, neutrophils, microglia, CD16$^+$ NK cells, and at least one of CD56$^+$ NK cells and γ/δ T cells. In another embodiment, said isolated cell populations comprise at least pDC, mDC-1, mDC2 and mDC-CD16$^+$. In another embodiment, said method further comprises isolating tumor cells or other non-immune cells within the sample.

In another embodiment, cell populations isolated by the methods of the invention are typically characterized by at least 80% purity and at least 80% viability. According to particularly advantageous embodiments, the combination of steps disclosed herein, including the non-aggressive high-viability-generating tissue dissociation by Ch NP, the use of antibody-fluorophore combinations as defined in the panels and/or the successive gating steps described herein provides for characterization and isolation (sorting) of prominent cell populations with purity of at least 90% or 95%, while maintaining their relative proportions in the source tissue as well as their phenotypic characteristics.

According to advantageous embodiments, the sorted (purified) cells may be subjected to genomic or proteomic analyses, to determine RNA and/or protein expression patterns of the cell populations isolated or any other genetic data (e.g. DNA mutations). These patterns and data, as well as the types and relative quantities of each cell population and their interrelations (herein referred to as immune patterns), may be used to determine the immune state of a subject, their response to treatment and other external or internal stimuli, and may be correlated with disease status, severity, prognosis or predicted response to treatment. Advantageously, the assays of the invention may be performed without substantially affecting the viability and activation status of the isolated cells, and while maintaining the relative proportions of cell populations. Thus, the assays of the invention may provide for improved cell isolation and further very high data-containing and high resolution characterization of expression patterns, having enhanced diagnostic and prognostic value. In another embodiment the methods further comprise correlating the results (e.g. quantities of leukocyte cell populations and/or expression patterns) to disease severity or to other clinical parameters such as overall survival or progression free survival. In another embodiment the methods further comprise correlating the results (e.g. quantities of leukocyte cell populations and/or expression patterns) to the therapeutic outcome of an immune modulating cancer treatment. In another embodiment the methods comprise determining RNA and/or protein expression patterns of the cell populations isolated. In another embodiment said methods further comprise correlating the quantities, RNA and/or protein expression patterns of leukocyte cell populations to disease severity or to the therapeutic outcome of an immune modulating treatment (e.g. immune modulating cancer treatment). In another embodiment said methods comprise isolating separately RNA samples from each of the cell populations isolated. In another embodiment said methods comprise determining RNA and/or protein expression patterns of each of the cell populations isolated, and correlating the cell quantities and the RNA and/or protein expression patterns of the cell population to disease severity, prognosis or predicted response to treatment.

For example, the methods of the invention may further comprise determining the expression level of at least one immune-modulating cellular target on each of the cell populations isolated and correlating the results to the therapeutic outcome of a cancer treatment directed to said at least one immune-modulating cellular target. For example, the immune-modulating cellular targets may be pairs or groups of immune suppressive molecules and their ligands (herein referred to as suppressive layers, including, but not limited to PD1 and PD-L1, TIM3 and CAECAM1 and Galectin 9, or LAG3 and Galectin 3 and HLA-DR). According to exemplary embodiments, expression of at least one target within such layer (pair or group) on at least one and preferably a plurality of the immune or tumor cell populations isolated from a patient's tumor indicates that a cancer treatment directed to said suppressive molecule(s) is likely to be beneficial in said patient.

Other objects, features and advantages of the present invention will become clear from the following description and drawings.

BRIEF DESCRIPTION OF THE DRAWINGS

FIG. 1A-B. Brain tumor (BT) dissociation to single cells using Dispase (Disp) or Papain, or a combination of DNase, Collagenase and Hyaluronidase (DCH) (FIG. 1A—viability, FIG. 1B—cumulative grade). Dispase showing higher cell mix quality and viability than other tested dissociation methods.

FIG. 5A—panel including TcR-Vα24Jα18-specific antibody. FIG. 5B—panel including CD19-specific antibody (top 6 panels—PBMC sample, bottom 6 panels—dissociated glioblastoma sample).

FIG. 12A-B. Serial gating of tumor-panel stained anaplastic astrocytoma (AA) cells. FIG. 12A—initial analysis steps: removal of doublets and clumped cells, precluding reading artifacts and viability identification. FIG. 12B—six dot plots of Tumor-panel stained cells (top right) and six dot-plots of Isotype panel-stained controls (bottom left).

FIG. 13A-D. Multi-parametric Intra-nuclear, intracytoplasmic and extracellular marker expression pattern of cells dissociated from various brain-derived lesions (FIG. 13A—brain, FIG. 13B—lung metastases to the brain, FIG. 13C—Anaplastic astrocytoma (AA), FIG. 13D—glioblastoma (GBM)).

FIG. 14A. Percoll gradient purification of cells. Percoll purification (collection of cells from the layer in the gradient) increases the percentages of cells with viabilities. FIGS. 14B and 14C. Staining of non-purified and Percoll gradient purified cells using the tumor panel showing that the percent of proliferating cells (Ki67$^+$) or those expressing a glial marker and the Ki67 marker increase within the layer of cells purified from the percoll gradient. GBM, glioblastoma; AA, Anaplastic astrocytoma; ODG, oligodendroglioma.

FIG. 15B—DC panel sorted cells; FIG. 15C—innate panel sorted cells).

DETAILED DESCRIPTION OF THE INVENTION

Figure 2B:
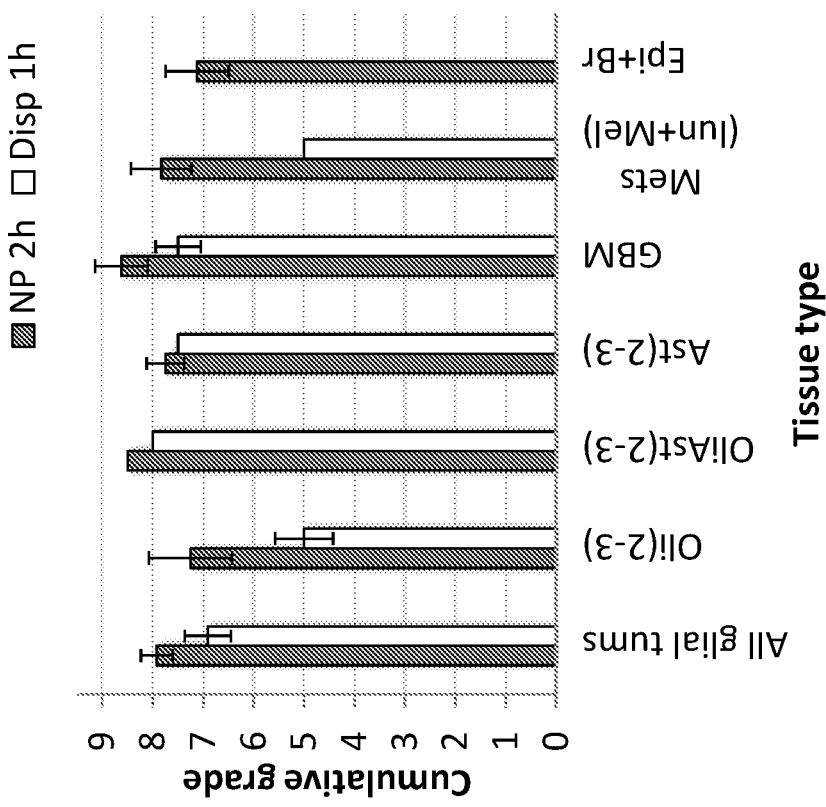
FIG. 2A-B. BT dissociation to single cells using Dispase or Neutral protease (NP). Cellular viability (FIG. 2A) and cumulative grade of quality of dissociation (CG 3-9 scale, FIG. 2B) of tissue samples dissociated with NP versus Dispase, showing enhanced quality and viability of dissociation with NP. Oli (2-3), oligodendroglioma grade 2 and 3; OliAst (2-3), oligoastrocytoma grade 2 and 3; AA, Anaplastic astrocytoma (astrocytoma grade 3); Ast (2-3), Astrocytoma grade 2 and 3; GBM—glioblastoma; Mets—metastases (lung+melanoma); Epil, Epileptic focus.

The invention relates to the field of cytometry, specifically to flow cytometric methods and kits for improved tumor diagnosis, prognosis and monitoring. More specifically, embodiments of the invention relate to compositions and methods providing high resolution quantitative means for immunophenotyping and cytomic modeling, and for identifying and selecting effective tumor-specific therapies.

I) ANTIBODIES, CYTOMETRIC PANELS AND KITS

The invention relates in some embodiments to improved and advantageous cytometric panels and kits. The term cytometric panel as used herein relates to a set of antibodies (or other specific antigen-binding agents) which are labeled (directly or indirectly) with detection markers such as fluorophores. This set of antibodies may be used in some embodiments to simultaneously label a cell-containing biological sample (in suspension). In other words, the sample is typically and advantageously incubated with an entire cytometric panel as disclosed herein, thus allowing characterization and physical separation (e.g. via sorting) of multiple cell populations in a single measurement step, using multi-parametric analysis of the antigen co-expression pattern on single cells from the sample. Accordingly, antibodies that are directed to distinct cellular targets for which separation is desired within a panel, are labeled with distinct (non-equivalent) fluorophores, and are referred to herein as distinct fluorophore-labeled antibodies.

The term kit as used herein relates to an article of manufacture comprising at least one and typically a plurality of cytometric panels of the invention, and optionally additional reagents, e.g. reagents for cell dissociation, purification, permeabilization, control samples or antibodies, or other reagents for use in flow cytometry. The kit may further contain instructions for using the at least one cytometric panel in the methods of the invention, e.g. instructions for analyzing the results measured using multi-parametric analysis as detailed herein.

For example, the kit may further comprise one or more isotype control antibodies (i.e. antibodies of the same animal species and isotype, conjugated to the same fluorophore used in the panel, but not capable of binding the cellular targets expressed by the corresponding cell populations). In another embodiment, the kit may contain compensation reagents, e.g. bead controls that are labeled for each fluorophore used in the assay. In another embodiment, the kit further comprises reagents for cell purification or dissociation of cells from a tissue sample. In a particular embodiment, the reagent for cell dissociation is a protease, e.g. *Clostridium histolyticum* Neutral Protease (Ch NP) or Dispase-II from *Bacillus Polymyxa*. Such reagents are readily available to the skilled artisans and may be obtained commercially or manufactured by methods known in the art. For example, Ch NP in clinical grade may be obtained from AMSBio-Abingdon, UK or SERVA, Heidelberg, Germany. In addition, Ch NP may be isolated from Ch cultures or produced recombinantly, by available methods. For example, recombinant Ch NP, encoding nucleotide sequences and preparation thereof are described in U.S. Pat. No. 5,853,976.

Antibodies, or immunoglobulins, comprise two heavy chains linked together by disulfide bonds and two light chains, each light chain being linked to a respective heavy chain by disulfide bonds in a "Y" shaped configuration. The variable domains of each pair of light and heavy chains form the antigen binding site. The isotype of the heavy chain (gamma, alpha, delta, epsilon or mu) determines immunoglobulin class (IgG, IgA, IgD, IgE or IgM, respectively). It should be understood that when the terms "antibody" or "antibodies" are used, this is intended to include intact antibodies, such as polyclonal antibodies or monoclonal antibodies (mAbs), as well as proteolytic fragments thereof such as the Fab or F(ab')$_2$ fragments. Further included within the scope of the invention are chimeric antibodies; recombinant and engineered antibodies, and fragments thereof, as well as other molecules comprising at least an antigen binding site (retaining the antigen binding capacity) of an antibody.

The term "antigen" as used herein is a molecule or a portion of a molecule capable of being bound by an antibody. The antigen may be capable of inducing an animal to produce antibody capable of binding to an epitope of that antigen. An antigen may have one or more epitopes. The specific reaction referred to above is meant to indicate that the antigen will react, in a highly selective manner, with its corresponding antibody and not with the multitude of other antibodies which may bind other antigens. The term "specifically bind" or "directed to" as used herein with respect to antibodies means that the binding of an antibody to an antigen is not competitively inhibited by the presence of non-related molecules (antigens).

Typically and advantageously, the panels of the invention comprise monoclonal antibodies that are labeled directly (conjugated) to a fluorophore. Various fluorophores suitable for use in flow cytometry are known in the art. Certain particularly advantageous combinations of antibody-fluorophore pairs and panels comprising them are disclosed in the Examples section herein. According to some embodiments, the assays of the invention may include the use of a plurality of the following combinations as set forth in Table 1:

TABLE 1 exemplary antibody-fluorophore combinations

| Antibody target | Description | Fluorophore [excitation/emission maxima (Ex/Em) in nm] |
| --- | --- | --- |
| CD45 | Protein tyrosine phosphatase, receptor type, C (PTPRC) | Allophycocyanin (APC) [650/660 Ex/Em] |
| CD11b | Mac-1 α or integrin αM chain | Alexa Fluor ® 488 [495/519] |
| CD3 | CD3-epsilon chain, a part of the T cell receptor complex | APC-H7 [650/ 774], APC-eFluor 780 [650/780]; or Pacific blue (Pac-bl [401/452]) for lineage⁻ |
| CD4 | A glycoprotein found on the surface of immune cells such as Th, monocytes, macrophages, and DC | PE-Cy5.5 (Phycoerythrin Cyanine 5.5 [650/694]) |
| CD8 | transmembrane glycoprotein that serves as a co-receptor for the T cell receptor (TCR) | Quantum dots-655 (QD655 - broad excitation range 300-4020/Em = 655]), eVolve 655 (405/655)eVolve 650 |
| CD56 | Neural cell adhesion molecule (NCAM), a homophilic binding glycoprotein expressed on the surface of neurons, glia, skeletal muscle and NK cells and NK-T cells | PE-Cy7 [496/785 ]; or Pac-bl (Pacific blue) for removal of cells of certain lineages (lineage⁻) |
| TcR-Vα24Jα18 | TCR alpha chain expressed by type 1, invariant chain NK-T cells. | PE-Phycoerythrin [496, 566/578] (or R-PE) |
| CD14 | a co-receptor (along with the Toll-like receptor 4 and MD-2) for bacterial lipopolysaccharide | QD655; or Pac-bl (for lineage⁻) |
| HLA-DR | Human Leukocyte Antigen, antigen D Related; MHC class II cell surface receptor encoded by the HLA complex | APC (allophycocyanin) eflour ® 780 |

TABLE 1-continued exemplary antibody-fluorophore combinations

| Antibody target | Description | Fluorophore [excitation/emission maxima (Ex/Em) in nm] |
|---|---|---|
| CD16 | low affinity Fc receptor | PE, PerCp-Cy5.5 (Peridinin Chlorophyll Protein Cyanine 5.5 [482/695]) |
| CD33 | Siglec-3 (sialic acid binding Ig-like lectin 3, SIGLEC3, SIGLEC-3, gp67, p67) - a transmembrane receptor expressed on cells of myeloid lineage | PerCp-Cy5.5 |
| CD66b | Carcinoembryonic antigen-related cell adhesion molecule 8 (CEACAM8) expressed on granulocytes | V450 (BD HorizonTM V450) [404/448] |
| CD1c | BDCA-1, a member of the CD1 family of proteins structurally related to MHC class I proteins, that present non-peptide antigens to T cells and NK-T cells | PE-Cy7 (Phycoerythrin Cyanin 7 [496,565/774]) |
| CD141 | BDCA-3 or thrombomodulin; mediates co-agglutination by interaction with thrombin and protein C | PE |
| CD123, CD303 or CD304 | CD123 - CD123- IL3 receptor; CD303 - BDCA-2, CLEC4C membrane protein; CD304 - BDCA-4, VEGF165R | FITC (Fluorescein Isothiocyanate [490/525]) |
| CD20 or CD19 | CD20 - B-cell antigen, an activated-glycosylated phosphoprotein expressed on the surface of all B-cells beginning at the pro-B phase (CD45R$^+$, CD117$^+$) and progressively increasing in concentration until maturity. CD19 - B cell marker, co-receptor in conjunction with CD21 and CD81 | PE; or Pac-bl for lineage$^-$ |
| GFAP | Glial fibrillary acidic protein, an intermediate filament protein that is expressed by astrocytes and ependymal cells | Alexa Fluor 647 [650/668] |
| A2B5 | c-series ganglioside-specific antigen, marker for immature glial-committed precursors, and for cancer-initiating cells | PE |
| IL-13Rα2 | CD213A2 - binds IL13 with high affinity, but lacks a cytoplasmic domain | FITC (secondary antibody) |
| Ki67 | MKI67 or MIB1, a cellular marker for proliferation | PE-Cy7 |

According to some embodiments, the assays of the invention may include the use of a plurality of combinations as set forth in any one of Tables 3-7 and 9. According to other embodiments, the use of fluorophores having the same potency (quantum yield in aqueous media or staining index) to the exemplary fluorophores listed herein is contemplated. According to additional embodiments, the use of fluorophores equivalent or substantially equivalent to the specific fluorophores listed in Table 1, 3-7 or 9 herein is further contemplated. The term equivalence with respect to fluorophores (including tandem dyes such as PE-Cy7) refers to comparable relative fluorescent strength and wavelength of emission, typically determined by comparing the potency (quantum yield or staining index) and color (typically defined by emission maxima and/or full width half maxima). For example, substantially equivalent fluorophores having similar emission potency (e.g. ±20% or 25%) and emission maxima (e.g. ±50 nm) may be used in some embodiments. In some embodiments, the term equivalence with respect to fluorophores further refers to comparable wavelength of excitation and wavelength of emission typically defined by the excitation and emission maxima (±50 nm) and/or full width half maxima. Fluorescent dyes may be classified as potent or less potent based on their relative fluorescent strength according to staining index scales known in the art. For example, potent fluorophores may be defined as having a staining index of over 200 and less potent fluorophores may be defined as having a staining index lower than 200 (see e.g. www.nature.com/nmeth/journal/v5/n12/fig_tab/nmeth.f.229_T1.html). According to another example, fluorophores may be divided into e.g. three groups according to staining index similarity, e.g. having a staining index of 0 to 100, higher than 100 and up to 200, or at least 200.

The panels, kits and methods according to embodiments of the invention incorporate the use of a viability dye, typically a fluorescent viability dye e.g. an amine viability dye. Amine-reactive dyes, also known as LIVE/DEAD® fixable dead cell stains, are a class of viability dyes suitable for identifying dead cells in samples that may be fixed. These dyes cross the cell membranes of dead cells, and irreversibly react with free amines in the cytoplasm. Live cells exclude these dyes because their cell membranes are intact, and free dye is washed away after staining. Since amine-reactive dyes are fluorescent when excited by lasers, dead cells can be identified by flow cytometry. Commonly used amine reactive dyes include, but not limited to, dyes of the ViViD and Aqua Blue series (Invitrogen). In some embodiments, ViViD violet, having excitation/emission (Ex/Em) at 416/451 nm, or substantially equivalent viability dyes may be used in the methods of the invention.

In another embodiment provided is a kit for characterizing cell populations in a human tissue sample, comprising a fluorescent viability dye and fluorophore-labeled antibodies directed to human cellular targets comprising: CD45, CD3, CD4, CD8, CD14, CD16, CD141, CD1c, CD56, at least one of CD123, CD303 and CD304, at least one of TcR-Vα24Jα18, CD19 and CD20, and optionally at least one of CD11b, HLA-DR, CD33, CD66b and TcRγ/δ, wherein the kit comprises at least one cytometric panel comprising distinct fluorophore-labeled antibodies directed to human CD45 and at least five additional distinct targets (of said human cellular targets, selected from the group consisting of CD3, CD4, CD8, CD14, CD16, CD141, CD1c, CD56, CD123, CD303, CD304, TcR-Vα24Jα18, CD19, CD20, CD11b, HLA-DR, CD33, CD66b and TcRγ/δ). In another embodiment, the distinct fluorophores are selected from the group consisting of: FITC, BV650, eVolve 655, PE, PerCP-Cy5.5, eFluor 450, PE-Cy7, APC, V450, APC-eFluor 780, and substantially equivalent fluorophores.

In another embodiment there is provided a cytometric kit comprising a viability dye and a plurality of labeled antibodies. In another embodiment, the kit is useful for characterizing cell populations in a human tissue sample (obtained from solid tissues). In various embodiments, the cytometric kit comprises at least one and advantageously a plurality of cytometric panels useful for simultaneous identification and characterization of a plurality of cell populations, e.g. lymphocyte, innate cell, DC and tumor cell populations, within a given sample. In various embodiments, the labeled antibodies are directed to at least 5-8 distinct cellular targets selected from the group consisting of CD3, CD4, CD8, CD56, TcR-Vα24Jα18, CD45, CD11b, CD14, CD19, CD20, CD14, HLA-DR, CD33, CD16, CD66b, CD1c, CD141, CD123 and CD303. Each possibility represents a separate embodiment of the invention. In certain embodiments, the kit comprises a plurality of cytometric panels, each panel comprising a viability dye and a plurality (e.g. 5-8 or more) of antibodies directed to distinct cellular targets as detailed herein. Typically and conveniently, the antibodies used in the methods and kits of the invention are monoclonal or polyclonal antibodies directed to a cellular target of interest and conjugated to fluorophore markers. According to further typical embodiments of the invention, the kit is useful for identification and characterization of human cell populations. The cellular targets denoted herein may represent human markers that are surface-expressed, or intracellular or intranuclear targets.

In one embodiment, the kit is useful for identifying lymphocyte populations, and comprises a cytometric panel comprising a viability dye and distinct fluorophore-labeled antibodies directed to human CD45, CD11b, CD3, CD4, CD8 and CD56, and to one of TcR-Vα24Jα18, CD19 and CD20, and a plurality of lineage-specific antibodies, comprising: at least one antibody directed to a human monocyte/macrophage cellular target and at least one antibody directed to a human granulocyte cellular target, wherein if said panel comprises an antibody directed to TcR-Vα24Jα18, said lineage-specific antibodies further comprise at least one antibody directed to a human B cell cellular target. In a particular embodiment, the cytometric panel comprises:

i) an antibody directed to CD45, conjugated to APC or a substantially equivalent fluorophore (in terms of fluorescence yield or staining index, and typically also maximal emission (Em) wavelength, e.g. Alexa Fluor 647);

ii) an antibody directed to CD11b, conjugated to Alexa Fluor® 488 or a substantially equivalent fluorophore (e.g. FITC);

iii) an antibody directed to CD3, conjugated to APC-H7 or a substantially equivalent fluorophore (e.g. APC-eFluor 780);

iv) an antibody directed to CD4, conjugated to PE-Cy5.5 or PerCP-Cy5.5 or a substantially equivalent fluorophore;

v) an antibody directed to CD8, conjugated to QD655 or a substantially equivalent fluorophore;

vi) an antibody directed to CD56, conjugated to PE-Cy7 or a substantially equivalent fluorophore;

vii) an antibody directed to one of TcR-Vα24Jα18, CD19 or CD20, conjugated to PE or a substantially equivalent fluorophore;

viii) ViViD (violet viability dye) or a substantially equivalent viability dye; and ix) a plurality of fluorophore-conjugated lineage-specific antibodies, comprising: at least one antibody directed to a human monocyte/macrophage cellular target (e.g. CD14) and at least one antibody directed to a human granulocyte cellular target, wherein if said panel comprises an antibody directed to TcR-Vα24Jα18, said lineage-specific antibodies further comprise at least one antibody directed to a human B cell cellular target;

wherein the lineage specific antibodies are preferably conjugated to the same fluorophore, more preferably to a fluorophore that is substantially equivalent (in terms of maximal emission wavelength) to the viability dye, e.g. Pacific Blue (Pac-bl) or brilliant violet 421 (BV421). PacBl, or substantially equivalent fluorophore may thus be used to stain all unwarranted cell subsets, wherein the viability dye has similar emission maximum as that of PacBl. For example, according to advantageous embodiments, the monocyte/macrophage cellular target is CD14, the B cell cellular target is CD19 or CD20 and the granulocyte cellular target is CD66b, and the plurality of lineage-specific antibodies are conjugated to Pac-bl, wherein each possibility represents a separate embodiment of the invention.

In another embodiment, the kit is useful for identifying innate immune cell populations, and comprises a cytometric panel comprising a viability dye and distinct fluorophore-labeled antibodies directed to human CD45, CD11b, CD14, HLA-DR, CD16, CD33 and CD66b. In a particular embodiment, the cytometric panel comprises:

i) an antibody directed to human CD45, conjugated to APC or a substantially equivalent fluorophore;

ii) an antibody directed to human CD11b, conjugated to Alexa Fluor® 488 or a substantially equivalent fluorophore;

iii) an antibody directed to human CD14, conjugated to QD655 or a substantially equivalent fluorophore;

iv) an antibody directed to human HLA-DR, conjugated to APC eflour-780 or a substantially equivalent fluorophore;

v) an antibody directed to human CD16, conjugated to PE or a substantially equivalent fluorophore;

vi) an antibody directed to human CD33, conjugated to PerCp-Cy5.5 or a substantially equivalent fluorophore (e.g. PE Cy5.5);
vii) an antibody directed to human CD66b conjugated to V450 or BV421 or a substantially equivalent fluorophore; and
viii) ViViD violet or a substantially equivalent viability dye.

In another embodiment, the kit is useful for identifying DC populations, and comprises a cytometric panel comprising a viability dye and distinct fluorophore-labeled antibodies directed to CD45, CD14, HLA-DR, CD1c, CD141 and CD16, and to one of CD123, CD303 and CD304, and a plurality of lineage-specific antibodies comprising at least one antibody directed to a human T cell cellular target, at least one antibody directed to a human B cell cellular target and at least one antibody directed to a human granulocyte cellular target. In a particular embodiment, the cytometric panel comprises:
  i) an antibody directed to human CD45, conjugated to APC or a substantially equivalent fluorophore;
  ii) an antibody directed to human CD14, conjugated to Pac-bl or a substantially equivalent fluorophore;
  iii) an antibody directed to human HLA-DR, conjugated to APC eflour 780 or a substantially equivalent fluorophore;
  iv) an antibody directed to human CD1c, conjugated to Pe-cy7 or a substantially equivalent fluorophore;
  v) an antibody directed to human CD141, conjugated to PE or a substantially equivalent fluorophore;
  vi) an antibody directed to human CD16, conjugated to PerCp-Cy5.5 or a substantially equivalent fluorophore;
  vii) an antibody directed to human CD123, CD303 or CD304 conjugated to FITC or a substantially equivalent fluorophore;
  viii) ViViD violet or a substantially equivalent amine viability dye; and
  x) a plurality of fluorophore-conjugated lineage-specific antibodies comprising at least one antibody directed to a human T cell cellular target, at least one antibody directed to a human B cell cellular target and at least one antibody directed to a human granulocyte cellular target;
wherein the lineage specific antibodies are preferably conjugated to the same fluorophore, more preferably to a fluorophore that is substantially equivalent (in terms of maximal emission wavelength) to the viability dye, e.g. Pac-bl. For example, according to advantageous embodiments, the T cell cellular target is CD3, the B cell cellular target is CD19 or CD20 and the granulocyte cellular target is CD66b or CD15, and the plurality of lineage-specific antibodies are conjugated to Pac-bl, wherein each possibility represents a separate embodiment of the invention.

In another embodiment, the kit is useful for identifying brain tumor cell populations, and comprises a cytometric panel comprising a viability dye and antibodies directed to a proliferation marker such as Ki67, a glial cell marker such as GFAP, and at least two glioma-associated antigens (GAA) selected from the group consisting of: IL13 receptor α2 (IL13Rα2), CD133, EGFR, CD24, CD44, transferrin-R and IL-4R and A2B5. In a particular embodiment the cytometric panel comprises antibodies directed to human Ki67, GFAP, IL13Rα2, and A2B5, wherein the antibodies are directly or indirectly labeled with distinct fluorophores, and an amine viability dye. According to particular embodiments, the antibody directed to Ki67 is directly or indirectly labeled by PE-CY7 or a substantially equivalent fluorophore, the antibody directed to GFAP is directly or indirectly labeled by Alexa647 or a substantially equivalent fluorophore, the antibody directed to A2B5 is directly or indirectly labeled by PE or a substantially equivalent fluorophore the antibody directed to IL13Rα2 is directly or indirectly labeled by Alexa Fluor® 488 or a substantially equivalent fluorophore and the amine viability dye is ViViD violet or a substantially equivalent viability dye. In another aspect, there is provided a cytometric panel comprising antibodies directed to human Ki67, GFAP, IL13Rα2, and A2B5, wherein the antibodies are directly or indirectly labeled with distinct fluorophores, and an amine viability dye, preferably wherein the antibody directed to Ki67 is labeled by PE-CY7 or a substantially equivalent fluorophore, the antibody directed to GFAP is labeled by Alexa647 or a substantially equivalent fluorophore, the antibody directed to A2B5 is labeled by PE or a substantially equivalent fluorophore, the antibody directed to IL13Rα2 is labeled by Alexa Fluor® 488 or a substantially equivalent fluorophore, and the amine viability dye is ViViD violet or a substantially equivalent viability dye.

In various embodiments, said kit comprises additional reagents, e.g. reagents for cell separation, tissue dissociation, cell permeabilization (where required), control samples or antibodies, or other reagents for use in flow cytometry. For example, in another embodiment the kit further comprises one or more isotype control antibodies (i.e. antibodies conjugated to the same fluorophore used in the panels of the invention but not capable of binding the cellular targets expressed by said cell populations). In another embodiment, the kit further comprises reagents for cell purification or dissociation of cells from a tissue sample. In a particular embodiment, the reagent for cell dissociation is a protease, e.g. Ch NP. In another embodiment, the kit may comprise instructions for use of said kit on an enzymatically dissociated tissue sample. In a particular embodiment, the dissociation comprises incubation with Ch NP. In another particular embodiment, the sample is a solid tumor sample or a solid tissue sample such as a cerebral tissue sample.

II) CYTOMETRY AND ANALYSIS METHODS

In other embodiments, the invention relates to methods for characterizing cell populations in a human tissue sample, e.g. a dissociated cerebral tissue or tumor sample. According to some embodiments, the sample is obtained from a solid tumor, including, but not limited to, primary brain tumors (e.g. glioma, epedymomas, meningioma, glioblastoma, astrocytoma), brain metastases, urinary tract tumors, head and neck carcinomas, bladder tumors, liver tumors, lung tumors, breast tumors, ovarian tumors, prostate tumors, cervical tumors, colon tumors and other tumors of the intestinal tract, bone malignancies, connective and soft tissue tumors, and skin tumors (e.g. melanomas). Each possibility represents a separate embodiment of the invention. In another embodiment said sample is a brain, lung, skin, liver, kidney or connective tissue sample, wherein each possibility represents a separate embodiment of the invention. In particular embodiments, the tissue is other than a pancreatic tissue and/or an adipose tissue.

According to embodiments of the invention, a cell-containing sample is incubated, under conditions so as to allow specific antigen-antibody binding, with at least one cytometric panel of the invention, wherein each cytometric panel is incubated with a separate aliquot of the sample (and the antibodies and viability dye of each panel are concurrently or sequentially incubated with the same sample aliquot).

In another embodiment, the method further comprises, prior to incubation with at least one cytometric panel of the invention, a step of enzymatically (and/or physically) dissociating the tissue so as to produce a dissociated cell sample. In a particularly advantageous embodiment, the dissociation is performed by treating the sample with Ch NP so as to produce a cell sample comprising dissociated single cells. A "dissociated cell sample" and "cell sample comprising dissociated single cells" used in the methods of the invention is characterized as comprising at least 80% intact single cells. In a particular embodiment, the cell sample comprises dissociated single cells of high viability and high quality cell mix conditions. For example, the resulting cell sample comprising dissociated single cells is typically characterized by at least 80% or in some embodiments 85% or 90% average cell viability, as comprising at least 90% and advantageously at least 95% single cells (i.e. 10% and preferably 5% or less of the cells are present in the form of cell clumps), and as having debris content (pieces of cells—considerably smaller than any cells (smaller than 5 µm) of up to 1 for every 5, 50, 100 or 200 cells (e.g. measured microscopically).

Ch NP is a metalloprotease of about 34 kDa that hydrolyzes peptide bonds of non-polar amino acid residues, which may be obtained from Ch cell cultures. While this enzyme may be used as part of enzyme mixes comprising other enzymes such as collagenases, advantageous embodiments of the invention are directed to the use of Ch NP as a sole protease, providing high grade dissociated cell samples having superior viability and quality. Thus the methods of the invention advantageously comprise incubating the tissue with purified Ch NP, devoid of other proteases.

Following the incubation with at least one cytometric panel of the invention (and binding of antigens of cells of the sample to antibodies of the panel), each aliquot may be subjected to reading and analysis by flow cytometry, thereby measuring the fluorescent emission of each fluorophore in each aliquot (i.e. in each cell within each aliquot). The fluorescent measurements of each aliquot (corresponding to cells which have specifically bound the labeled antibodies) may then be further analyzed, to identify the respective leukocyte cell populations. In various embodiments, analysis of the fluorescent measurements comprises a series of successive gating steps, in which identification of homogenous subpopulations of cells is performed based on the measured fluorescence intensities or light scatter properties, without having to physically separate the sets or subsets of cells (as could be done using cell sorting techniques). In another embodiment the methods comprises defining gating parameters for cell separation according to the properties of blood derived immune cells including PBMC, which parameters and gates may subsequently be used to identify the respective leukocyte populations in the first sample.

Gating may employ the use of the software capabilities of the flow cytometer, e.g. by manually drawing two-dimensional gates with a mouse on a computer screen, based on the density contour lines that are provided by software tools such as FlowJo or Diva. The cells falling in this gate may be selected (gated in) or excluded (gated out) and the process may be repeated for different two-dimensional (or higher) projections of the gated cells (e.g., two dimensional dot plots), thus resulting in a sequence of gates that describe subpopulations of the multivariate flow cytometry data. Alternatively, automated gating methods have been suggested, for example based on Density-Based Merging, Probability Binning Comparison or other algorithms.

Specific gating strategies are described in further detail in the Examples section herein. For example, the first gate may eliminate cell doublets, aggregates and debris so that the user can focus on single events or cells (singlets). The following gate can differentiate between dead cells and live cells, and optionally additional cells of unwanted lineages. Subsequent gating of live cells may classify the remaining cells into discrete cell populations according to the fluorescent measurements of each fluorophore. Several gates may be applied to a single cell projection and may divide the cells to one or more subsets, which may be further divided by subsequent gating steps.

In other embodiments, the cell populations may be physically sorted and isolated for further analysis. For example, the methods may comprise sorting and isolating a plurality of and preferably all of the following cell populations: cytotoxic T lymphocytes (CTLs), helper T cells (Th), $CD56^+$ natural killer (NK) cells, Type1—iNKT cells, Type 2-NKT cells, neutrophils, eosinophils, activated-M1 macrophages, alternatively activated-M2 macrophages, activated and non-activated microglia, $CD16^+$ NK cells, plasmacytoid DC and myeloid DC (mDC) of subtypes mDC-1, mDC2 and mDC-CD16 gamma/delta T cells. In another embodiment the methods may further comprise sorting and isolating non-immune cells e.g. tumor cells, endothelial cells and fibroblasts. According to advantageous embodiments, the methods facilitate sorting and isolating said cell populations with at least 80%, at least 85%, at least 90% or at least 95% purity. Advantageously, the methods of the invention provide for identification, characterization and/or isolation of said cell populations using as few as 1-3 cytometric panels (incubation/measurement cycles or steps as disclosed herein).

Unlike other assays used mainly in the characterization of blood leukocytes, the assays of the invention provide for accurate and sensitive analysis, facilitating the detection of cell populations even when present in small amounts (such as immune cells in solid tumors or tissues). In some embodiments, as demonstrated herein, the assays of the invention are particularly advantageous for the characterization of cell populations within cerebral tumors or other cerebral lesions. The assays allow identification, quantification and optionally isolation of the cell populations in an accurate manner, maintaining the proportions and phenotypes of the cell populations within the environment of interest (such as a solid tumor). This may have clinical importance and may also be advantageous in further analytical assays performed on the isolated cells.

In another embodiment there is provided a method for identifying immune cell populations in a human tissue sample, comprising:

a) enzymatically dissociating the tissue so as to produce a dissociated cell sample, b) incubating the sample, under conditions so as to allow specific antigen-antibody binding, with at least one cytometric panel comprising a fluorescent viability dye and distinct fluorophore-labeled antibodies directed to human CD45 and at least five additional distinct human cellular targets selected from the group consisting of CD45, CD3, CD4, CD8, CD14, CD16, CD141, CD1c, CD56, at least one of CD123, CD303 and CD304, TcR-Vα24Jα18, CD19 CD20, CD11b, HLA-DR, CD33, CD66b and TcRγ/δ, wherein each cytometric panel is incubated with a separate aliquot of said sample, c) subjecting the sample resulting from step b) to flow cytometry, thereby measuring the fluorescent emission of each fluorophore in said sample, so as to detect specific antigen-antibody binding to at least the following cellular targets: CD45, CD3, CD4, CD8, CD14, CD16, CD141, CD1c, CD56, at least one of CD123, CD303 and CD304, at least one of TcR-Vα24Jα18, CD19 and CD20, and optionally at least one of CD11b, HLA-DR, CD33, CD66b and TcRγ/δ; and d) analyzing the fluorescent measurements, thereby identifying the cell populations in said sample.

In other embodiments, the invention relates to methods for characterizing cell populations (e.g. immune cell populations) within a biological sample. In another embodiment, the methods comprise providing a first cell sample and a second cell sample, wherein the first sample is a human tissue sample comprising leukocyte populations of a subject (e.g. a tumor sample) and the second sample comprises peripheral blood mononuclear cells (PBMC). In various embodiments, the PBMC (second sample) may be obtained from the subject, or from a healthy donor. In certain advantageous embodiments, the first sample and the second sample are collected from the same subject at a first time point. In some embodiments, the second sample may be, for example, a whole blood sample, a red blood cell-depleted whole blood sample, or a purified PBMC sample. Each possibility represents a separate embodiment of the invention.

In some embodiments, the methods further comprise dissociating the tissue and isolating cells of the tissue sample, e.g. by mechanical separation of the tissue and/or enzymatic dissociation. Advantageously, this step is performed by enzymatic dissociation with NP. In another embodiment, the methods further comprise enzymatically dissociating the tissue by incubation with Ch NP so as to produce a cell sample comprising dissociated single cells. For example, without limitation, the tissue may be incubated with Ch NP for 1-2 hours at 37° C., or for 4-12 or 4-18 hours at room temperature. According to certain advantageous embodiments, longer incubation periods at room temperature may be employed, for example, the tissue may be supplemented with culture medium and incubated for e.g. 18-24 hours and up to 48 hours with Ch NP. In another embodiment, the methods comprise enzymatically dissociating the tissue by incubation with Ch NP so as to produce a cell sample comprising dissociated single cells with at least 80% average cell viability. As disclosed herein, samples can be incubated in ambient or room temperature with Ch NP for extended durations of up to up to 48 hours (e.g. while being transited to a central laboratory facility) with minimal or no loss of cell viability.

In another embodiment the methods comprise labeling the cells of the sample with at least one cytometric panel of the invention. In another embodiment the methods comprise labeling the cells of the sample with at least one cytometric panel comprising labeled antibodies directed to at least 5-8 distinct cellular targets selected from the group consisting of human CD3, CD4, CD8, CD56, TcR-Vα24Jα18, CD45, CD11b, CD14, CD19, CD20, CD14, HLA-DR, CD33, CD16, 6-Sulfo LacNAc, CD66b, CD15, CD1c, CD141, CD123, CD303 and CD304. It is to be understood, that panels comprising additional labeled antibodies directed to the cellular targets indicated above, e.g. up to 12 or 18 antibodies, may be used. Each possibility represents a separate embodiment of the invention.

According to advantageous embodiments, the methods of the invention provide for identification of microglial cells in the sample, and differentiation of microglial cells from other mononuclear cells such as macrophages. Thus, in some embodiments, the at least one cytometric panel comprises labeled antibodies directed to CD14 and CD16. In another embodiment the at least one cytometric panel comprises labeled antibodies directed to CD14, CD16 and CD33. In another embodiment the at least one cytometric panel comprises labeled antibodies directed to CD14, CD16, CD33 and CD11b. In another embodiment the at least one cytometric panel comprises labeled antibodies directed to CD14, CD16, CD33, CD11b and CD45. In another embodiment the at least one cytometric panel comprises labeled antibodies directed to CD14, CD16, CD33, CD11b, CD45, HLA-DR and CD66b. Each possibility represents a separate embodiment of the invention.

According to some embodiments, the panels used in the methods of the invention advantageously comprise specific marker-fluorophore combinations, which provide for fast, accurate and informative separation. In another embodiment the methods comprise incubating each sample, under conditions so as to allow specific antigen-antibody binding, with at least one cytometric panel, each panel comprising a fluorescent viability dye, an antibody directed to CD45 conjugated to conjugated to a potent fluorophore having high quantum yield or high staining index (such as PE, APC or substantially equivalent fluorophores), and fluorophore-conjugated antibodies directed to at least five distinct cellular targets selected from the group consisting of: human CD3, CD4, CD8, CD56, TcR-Vα24Jα18, CD45, CD11b, CD14, CD19, CD20, CD14, HLA-DR, CD33, CD16, 6-Sulfo LacNAc, CD66b, CD15, CD1c, CD141, CD123, CD303 and CD304 wherein each cytometric panel is incubated with a separate aliquot of each sample. In another embodiment the methods comprise incubating each sample, under conditions so as to allow specific antigen-antibody binding, with at least two cytometric panels, wherein each panel comprises a fluorescent viability dye, an antibody directed to CD45 conjugated to APC or a substantially equivalent fluorophore, and a combination of fluorophore-conjugated antibodies selected from the group consisting of:

i) distinct fluorophore-labeled antibodies directed to human CD45, CD11b, CD3, CD4, CD8 and CD56 and to one of TcR-Vα24Jα18, CD19 and CD20, and a plurality of lineage-specific antibodies, comprising: at least one antibody directed to a human monocyte/macrophage cellular target and at least one antibody directed to a human granulocyte cellular target, wherein if said panel comprises an antibody directed to TcR-Vα24Jα18, said lineage-specific antibodies further comprise at least one antibody directed to a human B cell cellular target;

ii) distinct fluorophore-labeled antibodies directed to human CD45, CD1 b, CD14, HLA-DR, CD16, CD33 and CD66b, iii) human CD45, CD14, HLA-DR, CD1c, CD141 and CD16, and to one of CD123, CD303 and CD304, and a plurality of lineage-specific antibodies comprising: at least one antibody directed to a human T cell cellular target, at least one antibody directed to a human B cell cellular target and at least one antibody directed to a human granulocyte cellular target.

In another embodiment, the methods comprise labeling the cells of the sample with a cytometric panel comprising:
i) an antibody directed to human CD45, conjugated to APC or a substantially equivalent fluorophore;
ii) an antibody directed to human CD11b, conjugated to Alexa Fluor® 488 or a substantially equivalent fluorophore;
iii) an antibody directed to human CD3, conjugated to APC-H7 or a substantially equivalent fluorophore;

iv) an antibody directed to human CD4, conjugated to PE-Cy5.5 or PerCP-Cy5.5 or a substantially equivalent fluorophore;
v) an antibody directed to human CD8, conjugated to QD655 or a substantially equivalent fluorophore;
vi) an antibody directed to human CD56 or CD16, conjugated to PE-Cy7 or a substantially equivalent fluorophore;
vii) an antibody directed to one of TcR-Vα24Jα18, CD19 and CD20, conjugated to PE or a substantially equivalent fluorophore;
viii) ViViD violet or a substantially equivalent viability dye; and
ix) a plurality of fluorophore-conjugated lineage-specific antibodies, comprising: at least one antibody directed to a human monocyte/macrophage cellular target a and an antibody directed to a human granulocyte cellular target;
wherein the lineage specific antibodies are preferably conjugated to the same fluorophore, e.g. Pacific Blue (Pac-bl).

In another embodiment, the methods comprise labeling the cells of the sample with a cytometric panel comprising:
i) an antibody directed to human CD45, conjugated to APC or a substantially equivalent fluorophore;
ii) an antibody directed to human CD11b, conjugated to Alexa Fluor® 488 or a substantially equivalent fluorophore;
iii) an antibody directed to human CD14, conjugated to QD655 or a substantially equivalent fluorophore;
iv) an antibody directed to human HLA-DR, conjugated to APC eflour 780 or a substantially equivalent fluorophore;
v) an antibody directed to human CD16, conjugated to PE or a substantially equivalent fluorophore;
vi) an antibody directed to human CD33, conjugated to PerCp-Cy5.5 or a substantially equivalent fluorophore;
vii) an antibody directed to human CD66b conjugated to V450 or a substantially equivalent fluorophore; and
viii) ViViD violet or a substantially equivalent viability dye.

In another embodiment, the methods comprise labeling the cells of the sample with a cytometric panel comprising:
i) an antibody directed to human CD45, conjugated to APC or a substantially equivalent fluorophore;
ii) an antibody directed to human CD14, conjugated to Pac-bl or a substantially equivalent fluorophore;
iii) an antibody directed to human HLA-DR, conjugated to APC eflour 780 or a substantially equivalent fluorophore;
iv) an antibody directed to human CD1c, conjugated to Pe-cy7 or a substantially equivalent fluorophore;
v) an antibody directed to human CD141, conjugated to PE or a substantially equivalent fluorophore;
vi) an antibody directed to human CD16 or 6-Sulfo LacNaC, conjugated to PerCp-Cy5.5 or a substantially equivalent fluorophore;
vii) an antibody directed to human CD123, CD303 or CD304 conjugated to FITC or a substantially equivalent fluorophore;
viii) ViViD violet or a substantially equivalent viability dye; and
xi) a plurality of fluorophore-conjugated lineage-specific antibodies comprising at least one antibody directed to a human T cell cellular target, at least one antibody directed to a human B cell cellular target and at least one antibody directed to a granulocyte cellular target;
wherein the lineage specific antibodies are preferably conjugated to the same fluorophore, e.g. Pac-bl.

In another embodiment, the method further comprises labeling the sample with negative control reagents, such as fluorophore-labeled non-specific antibodies (isotype control antibodies). In another embodiment, the methods comprise subjecting each separate aliquot of each sample resulting from the incubation step to flow cytometry, thereby measuring the fluorescent emission of each fluorophore in each aliquot of each sample. In another embodiment, the methods comprise analyzing the results (the fluorescent measurements of each aliquot of each sample, e.g. using multiparametric analysis) to determine the presence/absence and the intensity of fluorescence, in each cell, of each of the different fluorophores.

In various embodiments, analyzing comprises a series of successive gating steps, in which identification of homogenous subpopulations of cells is performed based on the measured fluorescence intensities or light scatter (forward and/or side scatter) properties. In another embodiment the methods comprise defining gating parameters for cell separation according to the properties of PBMC in the second sample, which parameters and gates may subsequently be used to identify the respective leukocyte populations in the first sample.

Thus, according to advantageous embodiments, the methods comprise analyzing the fluorescent measurements of each aliquot of the second sample, and comparing fluorescent measurements of each aliquot of the first sample to the measurements of each respective aliquot of the second sample, thereby identifying leukocyte cell populations in the first sample. In a particular embodiment, determining the expression of human cellular targets selected from the group consisting of: CD45, CD16, CD66b, CD141, CD123, CD303, CD304, CD3, CD4, CD8, CD56, CD19, CD20 and TcR-Vα24Jα18 comprises comparing the fluorescent measurements of the tissue sample to the respective measurements of the second sample.

Thus, in another embodiment, there is provided a method for characterizing cell populations in a human tissue sample, comprising:
a. enzymatically dissociating the tissue by incubation with Ch NP so as to produce a cell sample comprising dissociated single cells,
b. incubating each sample, under conditions so as to allow specific antigen-antibody binding, with at a cytometric panel comprising a fluorescent viability dye and distinct fluorophore-labeled antibodies directed to human CD45, CD11b, CD14, CD16 and CD33,
c. subjecting the sample resulting from step b. to flow cytometry, thereby measuring the fluorescent emission of each fluorophore in said sample, and
d. analyzing the fluorescent measurements, thereby identifying cell populations in said sample.

In another embodiment, there is provided a method for characterizing immune cell populations in a human tissue sample, comprising:
a. providing a first human tissue sample comprising leukocyte populations of a subject and the second sample comprises peripheral blood mononuclear cells (PBMC),
b. incubating each sample, under conditions so as to allow specific antigen-antibody binding, with at least one cytometric panel, each panel comprising a fluorescent viability dye, an antibody directed to CD45 conjugated to APC or a substantially equivalent fluorophore, and fluorophore-conjugated antibodies directed to at least five distinct human cellular targets selected from the group consisting of: CD3, CD4, CD8, CD56, TcR-Vα24Jα18, CD11b, CD14, CD19, CD20, CD14, HLA-DR, CD33, CD16, 6-Sulfo LacNaC, CD66b, CD15, CD1c, CD141, CD123, CD303 and CD304, wherein each cytometric panel is incubated with a separate aliquot of each sample;

c. subjecting each separate aliquot of each sample resulting from step b. to flow cytometry, thereby measuring the fluorescent emission of each fluorophore in each aliquot of each sample, d. analyzing the fluorescent measurements of each aliquot of each sample, wherein determining the expression of human cellular targets selected from the group consisting of: CD45, CD16, CD66b, CD141, CD123, CD303, CD304, CD3, CD4, CD8, CD56, CD19, CD20 and TcR-Vα24Jα18 comprises comparing the fluorescent measurements of the tissue sample to the respective measurements of the second sample.

In another embodiment analyzing comprises excluding (gating out) cell aggregates and debris according to the forward scatter and/or side scatter properties of the labeled cells (representing their size and their membrane complexity/granularity, respectively) For instance, gating on forward scatter (FSC) height on FSC width can reveal cell doublets and clumps. In another embodiment, analyzing comprises identifying and electing for further analysis (gating in) leukocytes by identifying cells expressing CD45. According to advantageous embodiments, this step facilitates gating out the tumor cells that form a large cell cloud, are frequently highly autofluorescent, sometimes expressing immune-related markers, these together may significantly reduce the ability to correctly identify and quantify cells. In another embodiment analyzing advantageously comprises gating in leukocytes by identifying cells expressing CD45 and CD11b. According to some embodiments, the inclusion of two markers (CD45 and CD11b) in both the lymphocytic panel and the innate panel enables easier comparison of the cellular data between these two panels In another embodiment analyzing comprises gating out dead cells identified by the viability dye. For example, in embodiments of the invention, dead cells in a sample labeled by a viability dye such as a dye of the fixable amine viability dye series, distinction between higher and lower fluorescing cell, allows for exclusion (gating out) of the higher fluorescing dead cells. In another embodiment, analyzing comprises gating out cell populations of unwanted lineages, by determining the expression of lineage-specific markers. For example, when identifying lymphocyte cell populations using a lymphocyte panel, other cell lineages such as granulocytes and monocytes are typically excluded. Conveniently, exclusion of several and preferably all unwanted cell lineages is performed in a single step, when the antibodies directed to the various lineage-specific markers are linked to a fluorophore fluorescing on the same detector as the other unwarranted markers.

Advantageously, the antibodies directed to the various lineage-specific markers (also referred to herein as lineage markers) are linked to the same or substantially equivalent fluorophore or collected on the same detector/channel as the viability dye, thus allowing exclusion of dead cells and unwanted cells in a single step. As disclosed herein, the use of such a "dump channel" for excluding both dead cells and unwarranted cells eliminates significant flow cytometry artifacts, and advantageously enables the identification, with high purity (typically >90%) of additional cell lineages such as γδ-T cells (CD3$^+$ CD4$^-$ CD8$^-$ CD56$^-$ CD14$^-$ CD19$^-$ and CD20$^-$), without requiring additional labeling steps and reagents. In another embodiment, lineage-specific cellular targets for a lymphocyte panel may include at least one monocyte/macrophage cellular target, at least one B cell cellular target and at least one granulocyte cellular target. In a particular embodiment, the macrophage cellular target is CD14, the B cell cellular target is CD19 or CD20 and the neutrophil cellular target is CD66b or CD15. The invention discloses in some embodiments that cell separation and identification having improved and clinically informative diagnostic and prognostic value may be obtained without specifically detecting B cells and even when excluding B cell populations from analysis.

In another embodiment, lineage-specific cellular targets for an innate cell panel may include at least one T cell cellular target, at least one B cell cellular target and at least one granulocyte cellular target. In a particular embodiment the T cell cellular target is CD3, the B cell cellular target is CD19 or CD20 and the granulocyte cellular target is CD66b.

In another embodiment, the methods comprise identifying leukocyte cell populations according to the fluorescent measurements of each fluorophore (e.g. the level of fluorescence measured). For example, CD14-high cells are excluded in the DC panel while both the CD14-negative and CD14-medium are gated in and further monitored.

Thus, in another embodiment of the methods of the invention, analyzing the fluorescent measurements of each aliquot comprises the steps of:

i. excluding from further analysis cell aggregates and debris according to the forward scatter and/or side scatter properties of the cells;

ii. identifying and electing for further analysis CD45-expressing leukocytes;

iii. excluding from further analysis dead cells identified by the viability dye; and iv. identifying leukocyte cell populations according to the fluorescent measurements of each fluorophore.

For example, in some embodiments, step iv. may comprise the steps of:

iv-a. analyzing the cells for CD45 and CD11b expression, thereby excluding from further analysis lymphocytes according to (expressing high levels of CD45 and medium to low levels of CD11b relative to other cell populations, see Table 8);

iv-b. analyzing the cells for CD33 and CD11b expression, thereby identifying and then excluding from further analysis neutrophils (and other granulocytes expressing high levels of both markers, see Table 8); and iv-c. analyzing the remaining cells for CD14 and CD16 expression, thereby identifying macrophage and microglia cell populations.

According to some embodiments, step iv-c may further comprise identifying eosinophils according to their diagonal auto-fluorescence pattern.

In another embodiment, the method further comprises analyzing the granulocytes identified in step iv-b) for CD45 and CD16 expression, thereby identifying eosinophils (expressing CD45 high and CD16 low) and neutrophils (expressing CD45 medium and CD16 high, see Table 8). In another embodiment, step iv-c) may alternatively comprise analyzing the CD45 high CD11b low to medium cells excluded in step iv-a for CD16, thereby identifying CD16 NK cells.

In another embodiment, the methods further comprise incubating an aliquot of the sample with a cytometric panel of the invention, in which at least one of the antibodies is replaced by its respective isotype control antibody linked to the same fluorophore, and comparing the results obtained with the two panels. This step may facilitate a more accurate placement of the gates and provide for improved identification and isolation of the leukocyte populations.

In another embodiment, the methods further comprise quantifying the leukocyte cell populations in the samples (e.g. in the first sample). In contradistinction from hitherto disclosed assays, offering non-quantitative or semi-quantitative evaluation of cell populations (such as the Griesinger publications), the invention advantageously provides fully quantitative assays. The ability to provide quantitative and reliable estimation of cell counts of the various lineages entails enhanced diagnostic and prognostic value. For example, the presence of large frequencies of $CD16^+$ NK cell populations in brain tumors such as glioblastomas is demonstrated herein to be correlated with increased patient survival.

In another embodiment, the methods further comprise sorting and isolating the cell populations identified.

According to particularly advantageous embodiments, the combination of steps disclosed herein, including the non-aggressive high-viability-generating tissue dissociation by Ch NP, the use of antibody-fluorophore combinations as defined in the panels and the successive gating steps described herein provides for characterization and isolation (sorting) of prominent cell populations with purity of at least 90% or 95%, while maintaining their relative proportions in the source tissue as well as their phenotypic characteristics.

For example, the purity of the sorted cells may be verified by examining the expression of lineage-specific markers in each population isolated (e.g. by real-time-PCR, TaqMan® PCR or other methods used in the art for determining gene expression). As demonstrated herein, by examining the expression of markers (cellular targets) such as CD3ε, NKp46, HLA-DR, CD14, CD66b, CD123 and CD11c, it was verified that the methods of the invention produced isolated cell populations including Th cells, CTL, B cells, mDC1, mDC2, pDC, $CD16^+$mDC, macrophages, neutrophils, microglia, and $CD16^+$ NK cells with no detectable contamination from other cell types (over 90%, 95% or 98% purity).

In another embodiment, the methods allow for monitoring the tumor infiltrating leukocyte network of a subject, e.g. as a function of time or to evaluate the subject's response to a given treatment. Thus, in other embodiments the methods may further comprise:

f. providing a third cell sample and optionally a fourth cell sample, wherein the third sample is a human tissue sample comprising leukocyte populations of the subject collected at a different time point than the first sample, and the fourth sample comprises PBMC, g. incubating each sample, under conditions so as to allow specific antigen-antibody binding, with the at least one cytometric panel incubated with the first sample, wherein each cytometric panel is incubated with a separate aliquot of each sample;

h. subjecting each separate aliquot of each sample resulting from step f. to flow cytometry, thereby measuring the fluorescent emission of each fluorophore in each aliquot of each sample, wherein determining the expression of human cellular targets selected from the group consisting of: CD45, CD16, CD66b, CD15, CD141, CD123, CD303, CD304, CD3, CD4, CD8, CD56, CD19, CD20 and TcR-Vα24Jα18 comprises comparing the fluorescent measurements of the third sample to the respective measurements of the fourth sample, i. quantifying the leukocyte cell populations in the third sample, and j. monitoring the changes in quantities of the leukocyte populations between the third sample and the first sample.

In another aspect, there is provided a method for characterizing cell populations within a dissociated cerebral tissue sample, comprising:

a. providing a dissociated cerebral tissue sample of a subject (e.g. a tumor sample);

b. incubating the sample, under conditions so as to allow specific antigen-antibody binding, with a cytometric panel comprising antibodies directed to Ki67, GFAP, and at least two cellular targets selected from the group consisting of: IL13 receptor α2 (IL13Rα2), CD133, EGFR, CD24, CD44, transferrin-R and IL-4R and A2B5, wherein the antibodies are directly or indirectly labeled with distinct fluorophores, and a viability dye;

c. subjecting the sample resulting from step b. to flow cytometry, thereby measuring the fluorescent emission of each fluorophore, and d. analyzing the results.

In another embodiment, the cytometric panel comprises antibodies directed to human Ki67, GFAP, IL13Rα2, and A2B5, wherein the antibodies are directly or indirectly labeled with distinct fluorophores, and a viability dye.

In another embodiment, analyzing the results comprises:

i. excluding from further analysis cell aggregates according to the forward scatter and/or side scatter properties of the cells;

ii. excluding from further analysis dead cells identified by the viability dye; and iii. identifying cell populations according to the fluorescent measurements of each fluorophore.

In another embodiment, the method further comprises, prior to incubation step b., a step of enzymatically dissociating the tissue so as to produce a dissociated cell sample. In a particularly advantageous embodiment, the dissociation is performed by treating the sample with Ch NP so as to produce a cell sample comprising dissociated single cells. In a particular embodiment, the cell sample comprises dissociated single cells of high viability and high quality cell mix conditions (having low amounts or substantially devoid of sub-cellular debris, DNA debris and non-dissociated cell clumps).

III) EXPRESSION PATTERN ANALYSES AND APPLICATIONS IN TREATMENT AND DIAGNOSIS

As disclosed herein, the methods of the invention facilitate the isolation of intact, viable cells, enabling further analysis of gene expression patterns and cellular functions. Thus, in another embodiment, the methods of the invention comprise obtaining high quality RNA samples (with RNA integrity number (RIN)>7.5) from at least 8, at least 10 at least 12 or all the following cell populations: CTLs, Th, $CD56^+$ NK cells, Type1—iNKT cells, Type 2-NKT cells, neutrophils, eosinophils, activated-M1 macrophages, alternatively activated-M2 macrophages, activated and non-activated microglia, $CD16^+$ NK cells, plasmacytoid DC and myeloid DC (mDC) of subtypes mDC-1, mDC2 and mDC-CD16, and gamma/delta T cells. In another embodiment, the methods of the invention comprise obtaining high quality RNA samples from at least the following cell populations: helper Th cells, CTLs, B cells, mDC1, mDC2, pDC, $CD16^+$ DC, macrophages, neutrophils, $CD16^+$ NK cells, optionally microglia (in brain tumors or samples), and at least one of $CD56^+$ NK cells and γ/δ T cells.

For example, the isolated cells may be assayed for their RNA expression (e.g. by gene array, nanostrings, RNA-Seq etc) revealing their entire expression pattern. Comparing the full transcriptome of all types of immune cells derived from treated versus untreated samples, of effectively-treated versus ineffectively treated samples would reveal which cells and factors should be followed more closely on the functional, i.e. protein level (e.g. via flow cytometry, Western blot etc). In addition, the full transcriptomic data (genes which are expressed or not expressed) and other genetic information (e.g. characterization of germline or somatic mutations) on each one of the identified cells (tumor and immune) may reveal how these cells may be manipulated in order to drive an optimal anti-tumoral response.

In addition, the expression of selected cellular targets, for example lineage markers (for verifying subset purity, e.g. CD3ε, NKp46, HLA-DR, CD14, CD66b, CD123 and CD11c) or immune-modulating cellular targets, may be assayed. For example, the methods of the invention may further comprise determining the RNA or protein expression level of at least one immune-modulating cellular target on each of the cell populations isolated and correlating the results to the therapeutic outcome of a cancer treatment directed to said (or related) target of at least one immune-modulating cellular target. There are currently more than 20 known single-molecule (homotypic) or different-molecule (heterotypic) interactions that mediate either suppression or activation of immune responses to tumors. For example molecules such as CEACAM1 that homotypically bind other CEACAM molecules can suppress all cells expressing these molecules. CEACAM can also heterotypically convey an inhibitory signal to TIM3 expressing cells. The TIM3 receptor also conveys an inhibitory signal following binding Galectin 9. A molecule such as PDL1 can function both as an inhibitory receptor when it binds CD80. Alternatively, PDL1 can act as a ligand when it binds another inhibitory receptor—PD1. According to exemplary embodiments, expression of at least one target within a suppressive layer (a pair or groups of immune suppressive molecules and their ligands e.g. PD1 and PD-L1, or TIM3 and CAECAM1 and Galectin 9, or LAG3 and Galectin 3 and HLA-DR) in at least one and preferably a plurality of the immune or tumor cell populations isolated from a patient's tumor, indicates that a cancer treatment directed to said suppressive molecule(s) is likely to be beneficial in said patient. In other embodiments, expression of cellular targets representing the cellular state of the sorted cell subset (e.g. activation or exhaustion) may further be assayed, e.g. cytokines such as IFN-γ, TNF-α, and IL2, to further evaluate the likelihood of treatment success.

According to advantageous embodiments, the methods of the invention involve determining not only the types and quantities of the cell populations isolated, but also the specific genetic and/or proteomic information (e.g. RNA and/or protein expression patterns) of each of the isolated populations, and advantageously also their interrelations. These factors and interrelations, herein referred to as immune patterns or network models, may be used to determine the immune state of a subject, their response to treatment and other external or internal stimuli, and may be correlated with disease status or severity. According to certain embodiments the collected patterns and data obtained by multiparametric analyses may be used to create a model in silico of the patient's intratumoral immune network, e.g. using statistical and systems biology algorithms or other suitable tools. The models may then be used to identify network controllers, e.g. network hub and bottlenecks, represented by specific cells, receptors, cytokines, or other molecules having a significant effect on the immune network, thus allowing prediction of the outcome of a proposed treatment or identification of new therapeutic targets that may be particularly effective in treating the tumor.

For example, modeling of immune networks may be performed using a "black-box" approach, namely modeling cells by their functional responses/outputs to specific stimuli/inputs, without modeling the underlying intracellular mechanisms governing them. Conveniently, in the models employed in methods of the invention, the basic structural building block is a cell, and the basic functional building block is a Stimulus to Response (S>R) module. An exemplary S>R module may include e.g. a specific stimulus (such as a cytokine) that affects a cell (e.g. via a receptor), to generate a response, e.g. secretion of soluble factors. The transformer function of the S>R module may employ e.g. algorithms such as Artificial Neural Network (ANN) or Neuro-Fuzzy Modeling (NFM). The sum of all inferred S>R functional modules for a specific cell (e.g. NK) may be combined into a "cell model". The inherent modular connectivity of the S>R modules enables the response generated by one cell's S>R module to become the stimulus of another cell's (or the same cell's) S>R module. Network integration may thus be readily performed by module self-assembly. Such model may recapitulate the complex response of the complex network of immune and tumor cells within a tumor. Without wishing to be bound by a particular theory or mechanism of action, the ability to identify and sort all prominent immune and tumor cells within a tumor, and transform different components of their immune responses into a network as disclosed herein is advantageous and may be of high importance in recapitulating the full immune-tumor connections e.g. for diagnostic or prognostic applications, or for predicting optimal treatment for a patient.

Thus, the invention offers a novel, systematic, high-resolution, high throughput cellular-level data collection, together with a novel modeling approach—an immune cytomic approach. Various clinical parameters, e.g. progression free survival (PFS), Overall survival (OS), MRI features and others, may be correlated both with the simple parameters of the collected data (e.g. cell number and gene expression patterns of intratumoral cells) and advantageously also with complex parameters derived from the modeling (e.g. with active S>R modules within a tumor-immune network, with various network patterns or states, and with various high-level immune network parameters). Integration of clinical and cellular parameters may yield both disease prognostic factors, and therapy predictive factors.

According to some embodiments, the methods of the invention may be used for determining and characterizing lymphocyte populations and/or innate cell populations in a sample. In other embodiments, the methods of the invention may be used for screening for drug candidates (e.g. for the treatment of a tumor in the subject). In other embodiments, the methods of the invention may be used for monitoring treatment efficacy (e.g. by immune therapies or other anti-tumor drugs) in the subject. In other embodiments, the methods of the invention may be used for correlating the immune phenotype of a subject and their prognosis, e.g. survival of a cancer patient. In other embodiments, the methods of the invention may be used for discovery of new targets that may be blocked, agonized or antagonized to induce a more potent anti-tumoral response.

In another embodiment the methods further comprise correlating the results (e.g. quantities of leukocyte cell populations and/or expression patterns) to disease severity or to other clinical parameters such as overall survival or progression free survival. In another embodiment the methods further comprise correlating the results (e.g. quantities of leukocyte cell populations and/or expression patterns) to the therapeutic outcome of an immune modulating cancer treatment. In another embodiment correlating the results further includes determining or predicting treatment efficacy. In another embodiment correlating the results further includes determining the patient's prognosis. In another embodiment correlating the results further includes determining or predicting a therapeutic outcome of an immune modulating cancer treatment. In another embodiment, the methods of the invention further comprise administering to the patient a treatment (e.g. immune modulating cancer treatment) determined to be likely to be beneficial in said patient. According to certain non-limitative examples, the treatment may be an inhibitor or antagonist of an immune modulating target selected from the group consisting of: PD1, PD-L1, PD-L2, TIM3, CAECAM1, Galectin 9, LAG3, Galectin 3, B7.1, 2B4, BTLA, CD160, LIGHT, VISTA, B7.2, BTNL2, B7-H3, B7-H4, Butyrophilin, CD48, HVEM, Siglec family, CTLA4, CD28, ICOS, ICOS-L, 4-1BB, 4-1BB-L, OX-40, OX-40L CD27, CD40, CD40L, A2aR, CD70, CD80, CD86 and HLA-DR. Each possibility represents a separate embodiment of the invention.

According to other embodiments, the invention is directed to diagnostic or prognostic methods for gliomas (e.g. glioblastomas), enabling the evaluation of overall survival or other clinical parameters associated with the subject's prognosis, diagnosis, or responses to therapy. According to these embodiments, the relative frequencies of $CD16^+$ NK cells, and optionally additional cells such as $CD16^+$ mDC, $CD8^+$ T cells, pDCs and $CD141^+$ mDC2, compared to the frequencies of these cell populations in a control population of glioma samples, is determined. For example, without limitation, the distribution of cell frequencies in a population of glioma samples may be calculated by dividing the measured amounts by the total number of nucleated cells in the sample or by the total amount of leukocytes ($CD45^+$ cells), which may be further subjected to log transformation. The relative frequencies may then be correlated with the desired prognostic parameter (e.g. overall survival, see Example 5).

Accordingly, in another aspect there is provided a method for evaluating the prognosis of a subject afflicted with glioma, comprising characterizing and quantifying leukocyte cell populations in a glioma sample of the subject, wherein significantly enhanced levels of $CD16^+$ NK cells in the sample compared to glioma controls (e.g. other glioma patients evaluated) is indicative of a favorable prognosis. In another embodiment, significantly enhanced levels of $CD16^+$ NK cells, $CD8^+$ T cells and pDCs in the sample compared to glioma controls is indicative of a favorable prognosis. In another embodiment significantly enhanced levels of $CD16^+$ NK cells, $CD16^+$ mDC, $CD8^+$ T cells and pDCs and significantly reduced levels of $CD141^+$ mDC2 in the sample compared to glioma controls is indicative of a favorable prognosis. In another embodiment characterizing and quantifying leukocyte cell populations in said sample is performed by a method comprising the steps as defined herein.

The following examples are presented in order to more fully illustrate some embodiments of the invention. They should, in no way be construed, however, as limiting the broad scope of the invention.

IV) EXAMPLES

Example 1. Improved Tissue Dissociation to Viable Single Cells

Freshly isolated brain tissue and brain tumor (BT) tissue, was transferred to the lab in saline or in Ringer lactate (Biological Industries, Beit HaEmek, Israel). The specimens were weighed following the removal of blood clots and necrotic areas. The cleansed tissue was cut into 1-2 mm pieces and resuspended in $HBSS^{(+Ca\ +Mg)}$ without phenol red (Biological Industries) at 100 mg tissue per ml. The tumor slurry was divided, 4 ml per 50 ml tube, to allow for complete trituration using a 5 ml Pasteur pipette.

The following enzymes or their combination were tested on the tumor slurry:
1. DNase-I (Sigma St. Louis, Mo., USA): DNase is an endonuclease used to reduce viscosity ('gooeyness') resulting from DNA released from dead cells. 2. Collagenase type IV from *Clostridium histolyticum* (Ch; Sigma): a metalloprotease that cleaves native triple-helical collagen. 3. Papain from *papaya* latex (Sigma): a relatively nonspecific protease. 4. Hyaluronidase type V from sheep testis (Sigma): an enzyme hydrolyzing glycosidic linkages in hyaluronic acid found in ECM. It is typically used as a supplement to dissociation with other proteases. 5. Dispase-II from *Bacillus Polymyxa* (Sigma): a non-specific metalloprotease that cleaves fibronectin, and collagen IV+I, but not collagen V or laminin. It hydrolyzes peptide bonds of non-polar amino acid residues. 6. Neutral protease (NP)—from Ch (AMSBio-Abingdon, UK): a metalloprotease that hydrolyzes peptide bonds of non-polar amino acid residues. The enzyme is free from collagenolytic activity.

Cell slurry containing tubes, with unlocked caps, were either left in room temperature (RT) overnight (ON), or incubated for 30', 60', or 120' at 37° C. Following incubation, the tumor tissue was triturated five times using a 5 ml plastic Pasteur pipette (Biologix, Zouqu, China). Triturated tumor cells were briefly mixed and after approximately 30 seconds, large undigested debris was collected using a Pasteur pipette from the bottom of the tube and discarded. The cell mixtures were then washed twice with $PBS^{-Ca\ -Mg}$ (Biological Industries), and a sample from the cell mixture was stained with trypan blue (Sigma) and counted.

Comparison of Tumor Dissociation Quality by Dispase, Papain, or a Combination of DNase, Collagenase and/or Hyaluronidase The first set of six side-by-side experiments was conducted solely on glial tumors. Enzymes evaluated were DNase, collagenase, with or without hyaluronidase, papain and dispase. Trypsin was not tested as it was reported to generate significant loss of cells, high cell death, membranal antigen cleaving, and RNA-degradation. Mechanical dissociation was used in this set of experiments as a control for enzymatic digestion. Enzyme concentration ranges tested used were obtained from the product data sheets or from published literature using the selected enzymes. The following concentration ranges were evaluated: papain (2-20 units/ml (u/ml)), Dispase (0.6-2.4 u/ml), DNase (1-20 u/ml), collagenase (0.02-0.2% W/V), and hyaluronidase (200-4000 u/ml). High, medium and low concentrations of each enzyme were evaluated for their dissociative ability for during 30, 60, or 120 minutes incubation or during ON incubation. All combinations of the three evaluated concentrations of DNase, collagenase, and hyaluronidase were also tested. DNase+collagenase without hyaluronidase was also evaluated.

FIG. 1A+B depict only the optimal enzyme concentrations for each enzyme/combination that were determined for a dissociation time of 1, 2 hours and ON (30 minutes gave inferior results). Optimal enzyme concentrations determined were: DNase—5 u/ml, collagenase—0.05% and hyaluronidase—1000 units/ml. The dissociation with DNase and collagenase, without hyaluronidase is not shown, as dissociation with DCH (DNase+collagenase+hyaluronidase) produced superior cell-mixture qualities and viabilities at similar concentrations. FIG. 1A depicts the percentage of viable cells following tissue dissociation. Cellular viability was the highest following dissociation with Dispase. DCH tested in three experiments produced comparable high viability. Enzyme unassisted mechanical dissociation by trituration produced significantly lower viabilities (P<0.0005), and was discontinued after the six experiments. Papain was discontinued after one experiment since it yielded inferior results even in comparison to mechanical dissociation yielding low fraction of viable cells, and very low cell yields. FIG. 1B shows the quality of dissociation for the different enzymes. Unlike the comparable cellular viabilities produced by dispase versus DCH, Dispase-dissociated tumors produced cell mixtures of significantly higher quality-higher cumulative grade (CG) than those dissociated with DCH or using mechanical dissociation. Tumors dissociated with papain attained CG that is lower than those that were mechanically dissociated.

The CG Grading system for cell-mixture quality was devised by evaluating three main parameters of mixture quality: cell-clumps (Conglomerates of cells that did not dissociate into single cells), sub-cellular debris (Fragments which are irregular in shape and smaller than any of the dissociated cells) and DNA debris (DNA spilt from dead cells. DNA debris is much larger than any cell, and appears as long semi-translucent strands in which many cells are entwined and lost). To reduce evaluation subjectivity, each parameter was evaluated on a 1-3 scale where 1 represents much debris, 2—little debris and 3—no debris. A cumulative grade (CG) for the quality of dissociation is the sum of the three dissociation parameter grades. CG ranges from 3-9, where a CG of 9 indicates a clean cell-mixture containing only single cells (live or dead) without any debris.

Taken together, in this initial set of experiments although DCH and dispase yielded mixtures with comparable viabilities, the cell mixtures qualities produced by dispase were of significantly higher than those with DCH (P<0.0001). Therefore the following experiments were continued with dispase only.

Comparison of Dispase Versus NP for Tumor Dissociation for Short Durations

Figure 2A:
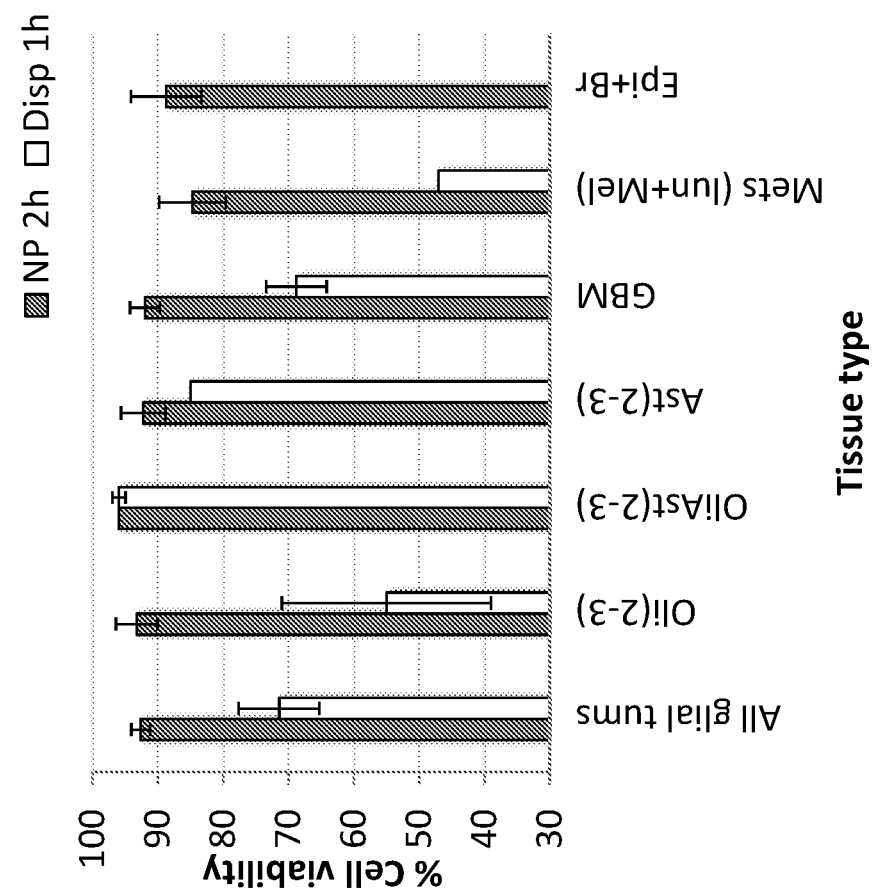
Figure 3B:
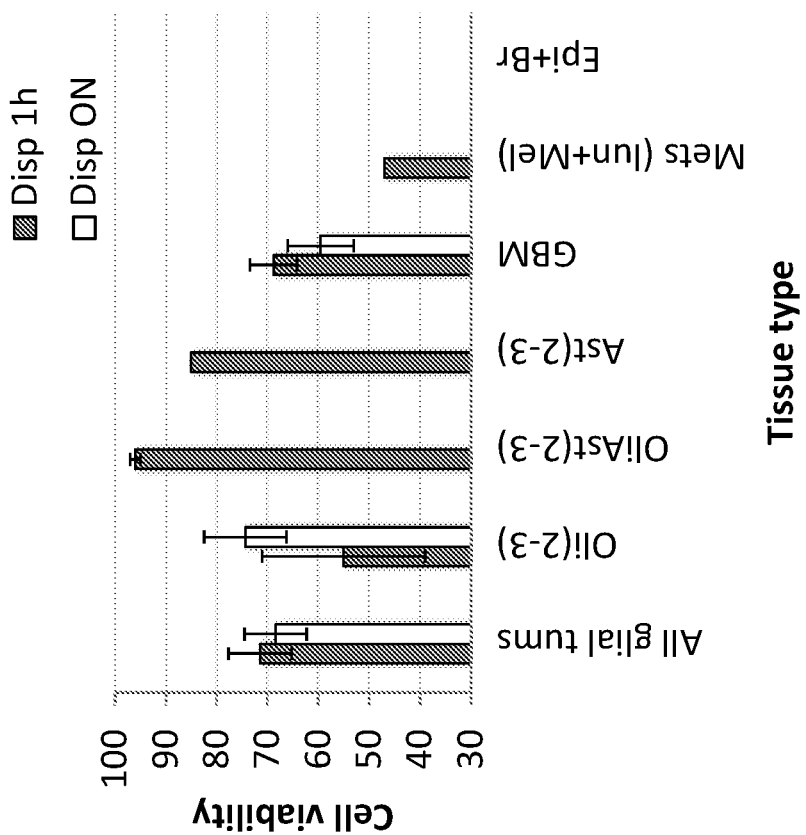
FIG. 3A-D. BT dissociation 2 hours (2h) versus overnight (ON) to single cells using Disp or NP (FIG. 3A—viability NP, FIG. 3B—viability dispase, FIG. 3C—NP CG NP, FIG. 3D—CG Dispase). Showing that NP produces cell mixes of high quality and viability, higher than those of Dispase following short and extended times of dissociation.
Figure 3A:
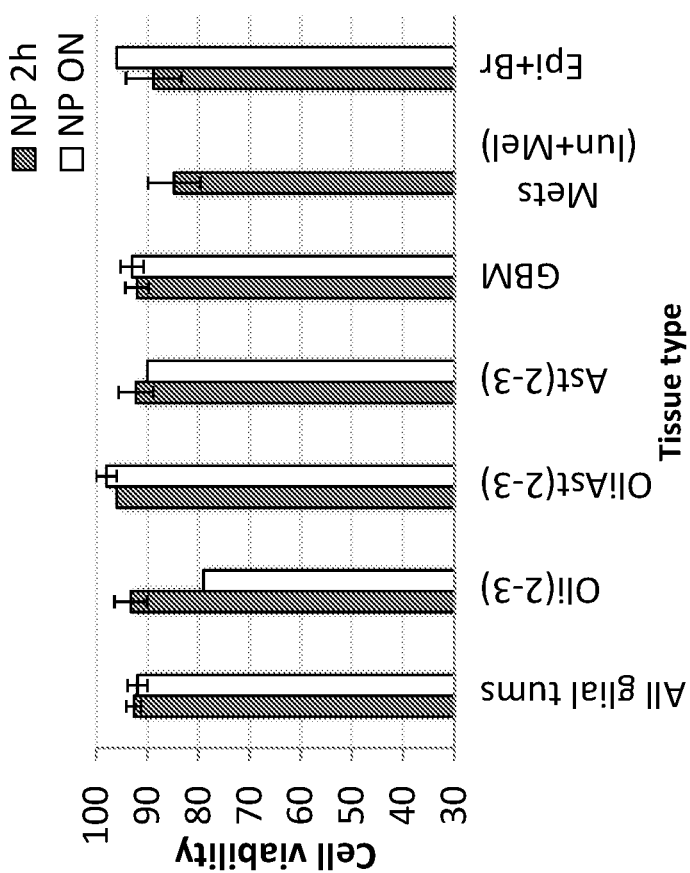
Figure 3D:
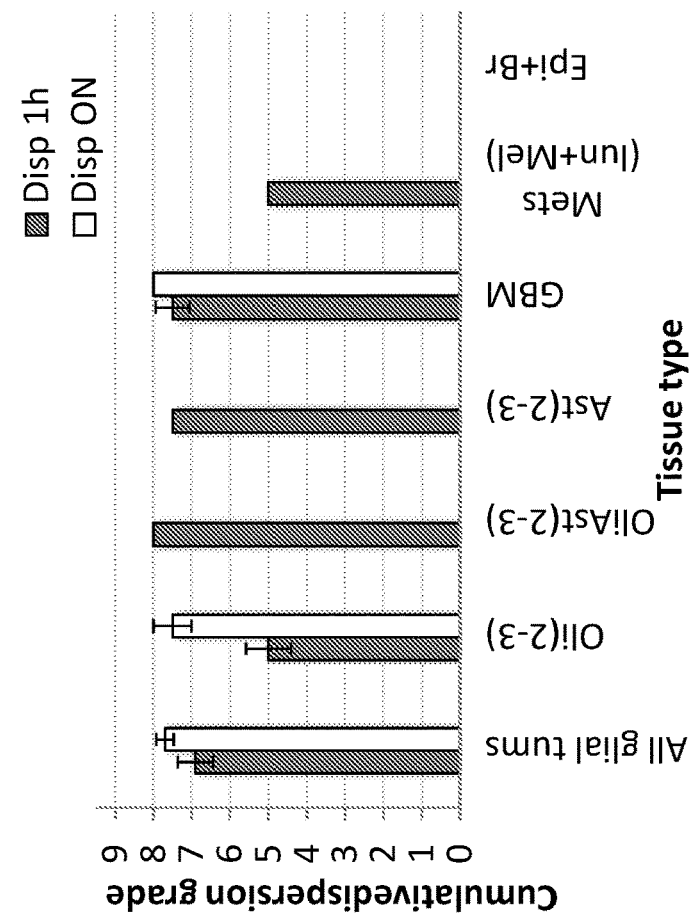
Figure 3C:
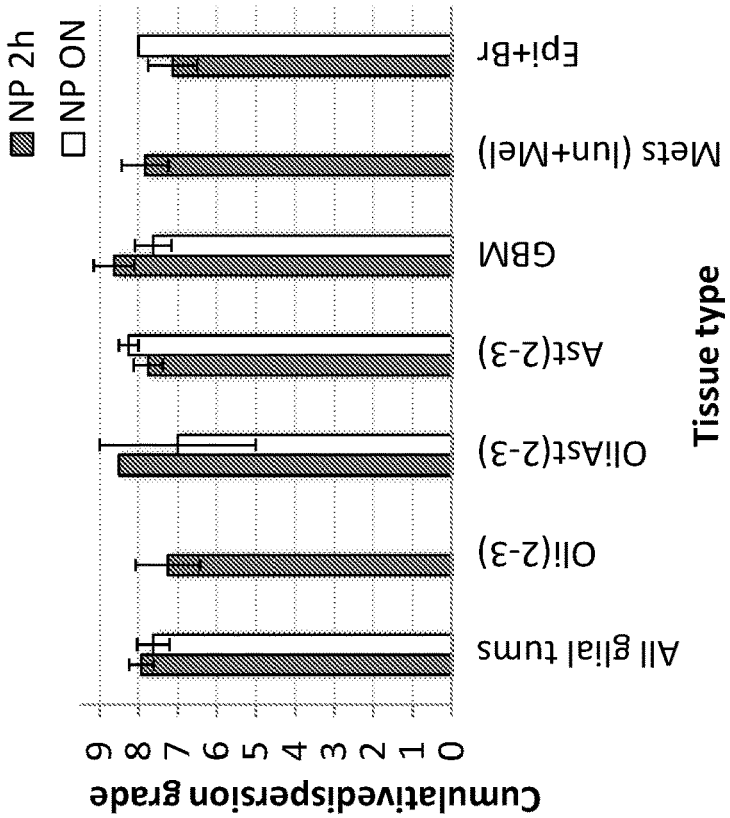

As no clinical grade dispase was found it was decided to test another type of neutral protease from a different microorganism—NP from Ch, an enzyme offered by several companies both in clinical-grade and in non-clinical grade. FIG. 2A+B compare tissue dissociation with dispase and NP. For brevity, only the determined optimal duration of dissociation for the two enzymes was compared (1 hour for dispase, and 2 hours for NP). Interestingly, although dispase and NP are both neutral proteases (hydrolyzing peptide bonds of non-polar amino acid), they displayed considerable differences in quality of dissociation. Similarly, Breite et al that compared these two enzymes in acellular in-vitro assays and showed that they differ in their proteolytic activities. FIG. 2A shows that NP produced consistently higher viabilities in the produced cell mixtures compared to Dispase for all types of tissues tested. Combining the results of all dissociated glial tumors (11 for Dispase versus 15 for NP), NP yielded significantly higher viability mixtures than Dispase (P<0.01), with a mean of >90% cellular viability of dissociated glial tumors. Dissociation with NP also showed consistently higher quality cell mixtures (FIG. 2B). Although no significant differences were found between the CG of NP and dispase, breakdown of the CG into its component parameters (clumps, remnants and gooeyness) revealed that short-term dissociation with NP produced less cell clumps, and significantly less subcellular-debris (remnants) than dispase (P<0.03). Both enzymes produce cell mixtures that were usually devoid of DNA debris.

Comparison of Tumor Dissociation Quality Between Dispase and NP Overnight

Labs may receive tissues from the operating room at late hours requiring tissue processing to be done after usual working hours. The development of a protocol to dissociate cells for longer durations may allow for short hands-on time while receiving the tissue, and subsequent work done after several hours. Ambient temperature dissociation of tumors for protracted duration may also allow shipping of tumors, while being gently dissociated. FIG. 3A-D show the viability and the quality of BTs and brain tissues dissociated overnight (ON) either in dispase or NP. The graphs compare dissociation results for each enzyme to itself, comparing short to long (ON) dissociation. The figures show that both enzymes give unchanged similar quality mixtures at shorter and longer durations. Again here, NP provided better results than dispase following ON dissociation, both in regards to cellular viability and to cell mixture quality. Alternative methods for ON dissociation, e.g. ON dissociation at 37° C., or maintaining minced-undissociated tumor ON at 4° C. and subsequently dissociating the tumor at 37° C., both yielded inferior quality and viability cell mixtures compared to ON dissociation at ambient temperature.

Viable Cell Outputs Following Tissue Dissociation Using Dispase Compared to NP

Table 2 summarizes the viable cell yields from all dissociations of glial tumors, brain metastases and brain tissues using dispase and NP, a total of 47 dissociations. The table displays data combined from the Dispase- and the NP-dissociated tissues to attain large sample sizes and more accurate cell-yield estimates.

TABLE 2

| cell viability following dissociation | | | | | |
|---|---|---|---|---|---|
| Tissue type (grouped) | Tissue subtype | N = NP/Disp | Mean $\times 10^6$ Cell/gr | STD $\times 10^6$ | Range $\times 10^6$ Cell/gr |
| All glial tumors | All primary glial BT subtypes | 22/16 | 103 | 70 | 19-376 |
| Oli (2-3) | Oli-2 | 5/6 | 107 | 106 | 19-376 |
|  | Oli-3 |  | 81 | 44 | 30-112 |
| OliAst (2-3) | OliAst-2 | 1/2 | 96 | 24 | 66-100 |
|  | OliAst-3 |  | 87 | — | 87 |
| Ast (2-3) | Ast-2 | 6/1 | 111 | 18 | 100-132 |
|  | AA |  | 135 | 72 | 37-189 |

TABLE 2-continued cell viability following dissociation

| Tissue type (grouped) | Tissue subtype | N = NP/Disp | Mean × $10^6$ Cell/gr | STD × $10^6$ | Range × $10^6$ Cell/gr |
|---|---|---|---|---|---|
| GBM | GBM | 10/7 | 73 | 42 | 21-136 |
| Mets | Melanoma + Lung | 4/1 | 64 | 35 | 34-117 |
| Epil + Brain | Epileptic focus | 5/0 | 115 | 7 | 110-120 |
|  | Brain |  | 289 | 330 | 99-670 |

The high natural variability in cell yields of BTs can be appreciated by the large ranges of cells attained per gram tissue even within groups of pathologically identical tumors. The average viable cell output per gram of anaplastic astrocytomas (AA) (grade III) was $1.35 \times 10^8$ while grade IV astrocytomas—GBMs yielded about half that number ($7.3 \times 10^7$ cells/g). Melanomas and lung metastases (Mets) to the brain yielded $6.4 \times 10^7$ cells/g, and non-tumoral brain tissues yielded $1.15 \times 10^8$ (epilepsy foci-Epil) to $2.89 \times 10^8$ (peritumoral brain) cells/g. The differences between the two types of non-tumoral brain tissue may be due to the different brain areas from which samples were obtained, or due to small sample size of these rare tissue specimens.

Freezing and Thawing of Dissociated Brain/Tumor Cells

Figure 4A:
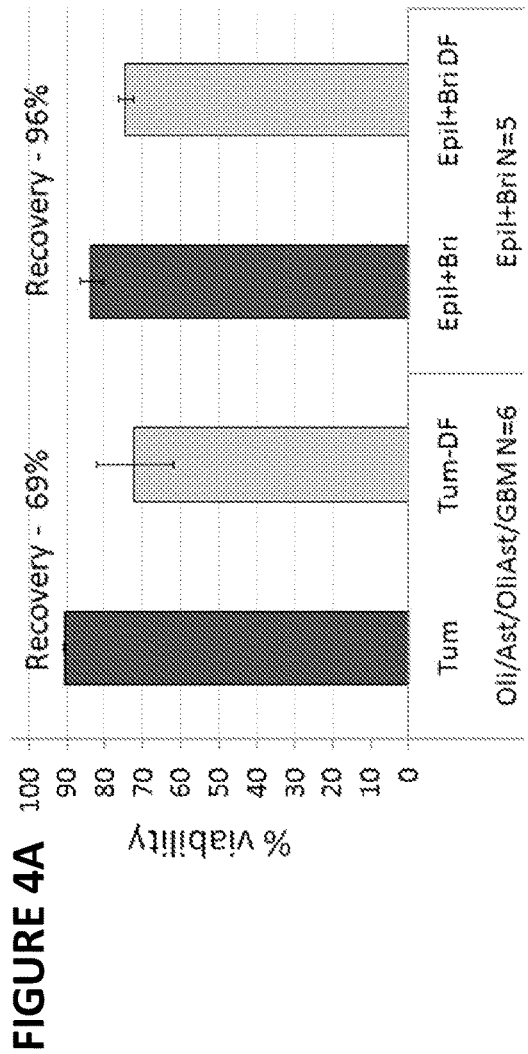
FIG. 4A. Cellular viability and viable cell recovery rates of freshly dissociated cells in comparison to their numbers following thawing.
Figure 4B:
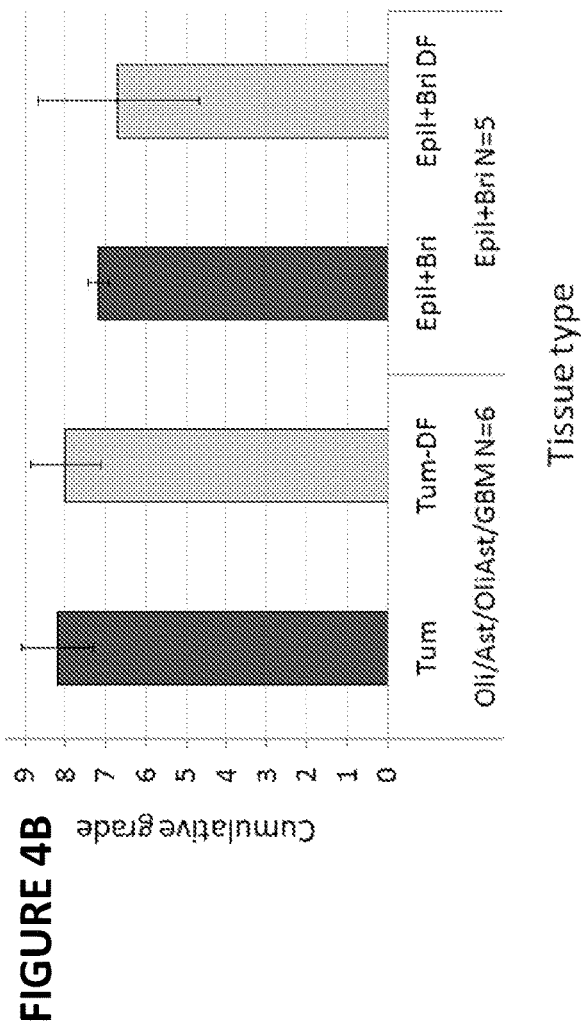
FIG. 4B. Respective cumulative dissociation grade (CG 3-9 scale). Tum—fresh tumor, Tum-DF thawed tumor. Epil+Bri epileptic brain lesion cells and non tumorous brain, Epil+Bri DF—thawed Epil+Bri.

Significant decline in the number of cells recovered following thawing is a known phenomenon for brain cells. FIG. 4A+B follows the fate of brain and BT cells dissociated by NP, frozen, and thawed using standard freezing and thawing procedures. FIG. 4A shows that after thawing, the fraction of viable BT cells decreased from 91% to 72%; the mean cell recovery rate (i.e. the number of live cells recovered divided by the number of live cells frozen) was 69%. The fraction of viable brain cells following thawing, decreased from 84% to 75%, with viable cell-recovery at 96%. The cell recovery rates are higher than those previously reported for human (55%-60%) or for rodent (56%) brain cells, probably due to the healthier condition of the cells before freezing. FIG. 4B follows the quality of the BT or brain tissue cell mixtures before freezing and after thawing, showing no significant changes. Cell mixtures that have lower quality before freezing are usually associated with lower yields of recovered cells after being thawed. DNA debris significantly reduces cell yields after thawing by entrapping cells. In mixtures of lower quality, the addition of DNA-hydrolyzing enzymes (e.g. DNase or Benzonase) to the defrosting medium is beneficial.

Example 2. Antibodies for Panel Construction

The following tables depict exemplary antibodies useful in construction of panels.

TABLE 3 antibody characteristics

| Antibody target and Fluorophore | Clone name | Isotype | Company |
|---|---|---|---|
| Alexa Fluor 488-CD11b | ICRF44 | Mouse IgG1 k | Biolegend |
| PE-CY5.5-CD33 | WM53 | Mouse IgG1 | Abcam |
| APC eFlour780- HLA-DR | LN3 | Mouse IgG2b k | eBioscience |
| Pac-Bl-CD14 | M5E2 | Mouse IgG2a k | Biolegend |
| QD655-CD14 | TuK4 | Mouse IgG2a k | Invitrogen |
| PE-CD86 | IT2.2 | Mouse IgG2b k | Biolegend |
| PerCP-Cy5.5-CD16 | 3G8 | Mouse IgG1 k | Biolegend |
| PE-Cy7-CD1c | L161 | Mouse IgG1 k | Biolegend |
| FITC-CD303 | AC144 | Mouse IgG1 k | Milteni Biotec |
| PE-CD141 | AD5-14H12 | Mouse IgG1 k | Milteni Biotec |
| eFluor 780-CD3 | SK7 | Mouse IgG1 k | eBioscience |
| APC-CD45 | 2D1 | Mouse IgG1 k | Biolegend |
| PE-Cy5.5-CD4 | S3.5 | Mouse IgG2a k | Invitrogen |
| NC650-CD8 | RPA-T8 | Mouse IgG1 k | eBioscience |
| PE-V-alpha24J | 6B11 | Mouse IgG1 k | eBioscience |
| Pac-Bl-CD3 | OKT3 | Mouse IgG2a k | Biolegend |
| Pac-Bl-CD56 | MEM-188 | Mouse IgG2a k | Biolegend |
| Pac-bl CD19 | HIB19 | Mouse IgG1 k | Biolegend |
| Alexa Fluor 647-GFAP | 1B4 | Mouse IgG2b k | BD |
| PE-A2B5 | 105-HB29 | Mouse IgM | Miltenyi biotec |
| IL-13Ra2 (Primary) | N/A | Goat IgG | R&D |
| FITC anti goat (2nd) | N/A | Donkey IgG | Jackson |
| Biotin-Fab Goat Anti Mouse IgG | N/A | Goat IgG | Jackson |

TABLE 4

Antibodies for lymphocyte panels

| Antigen | Fluorophore | Volume per 0.1 ml sample (ul) | Ab conc. (ug/ul) | Ab quantity (ug) per 0.1 ml sample | Manufacturer | Clone |
|---|---|---|---|---|---|---|
| CD66b | HRZN V450 | 3.5 | 0.1 | 0.35 | BD | G10F5 |
| CD56 | PE-Cy7 | 3 | 0.025 | 0.075 | eBioscience | CMSSB |
| CD11b | AF 488 | 2.1 | 0.4 | 0.84 | Biolegend | ICRF44 |
| TcR Vα24Jα18 | PE ($1^{st}$ panel - see Example 3) | 2.1 | 0.1 | 0.21 | eBioscience | 6B11 |

TABLE 4-continued

Antibodies for lymphocyte panels

| Antigen | Fluorophore | Volume per 0.1 ml sample (ul) | Ab conc. (ug/ul) | Ab quantity (ug) per 0.1 ml sample | Manufacturer | Clone |
|---|---|---|---|---|---|---|
| CD45 | APC | 1.5 | 0.05 | 0.075 | eBioscience | 2D1 |
| CD3 | APC-eFluor 780 | 1.4 | 0.05 | 0.07 | eBioscience | SK7 |
| CD19 | eFluor 450 ($1^{st}$ panel - see Example 3) | 0.9 | 0.1 | 0.09 | eBioscience | HIB19 |
| CD14 | PacB1 | 0.4 | 0.4 | 0.16 | Biolegend | M5E2 |
| CD4 | PE-Cy5.5 | 0.4 | 0.1 | 0.04 | Invitrogen | S3.5 |
| CD8 | QD655 | 0.12 | 0.05 | 0.006 | Invitrogen | 3B5 |
| CD19 | PE ($2^{nd}$ panel - see Example 3) | 10 | NA | 20 ul/test | BD | HIB19 |

TABLE 5

Antibodies for DC panels

| Antigen | Fluorophore | Manufacturer | Function (m = marker) | Volume per 0.1 ml sample | Antibody Concentration |
|---|---|---|---|---|---|
| CD45 | APC | Biolegend | Eeukocyte m | 1.5 ul | 0.06 ug/0.05 ml |
| HLA-DR | APC eflour 780 | eBioscience- | Maturation m | 2.5 ul | 0.03 ug/0.5 ml |
| CD86 | BrilliantViolet650 | Biolegend | Maturation m | 0.5 ul | 100 ug/ml |
| CD16 | PerCp-Cy5.5 | Biolegend | mDC m | 0.25 ul | 200 ug/ml |
| CD141 | PE | MilteniBiotec | mDC m | 7 ul | 11 μg/mL |
| CD1c | Pe-Cy7 | Biolegend | mDC m | 5.6 ul | 25 ul/ml |
| CD303 | FITC | MilteniBiotec | pDC m | 7 ul | 110 ug/mL |
| CD123 | FITC | Biolegened | pDC m | 5 ul | 200 ug/ml |
| ViViD | Vivid | molecular probes | Amine Viability m | 1.7 ul | Manufactures protocol |
| CD3 | Pac-bl | Biolegend | Lineage minus m | 0.21 ul | 0.5 mg/ml |
| CD14 | Pac-bl | Biolegend | Lineage minus m | 0.4 ul | 400 ug/ml |
| CD14 | QD655 | Invitrogen | | 0.1 ul | 1 uM |
| CD19 | eFlour 450 | eBioscience | Lineage minus m | 0.9 ul | 0.5 ug/0.5 ml |
| CD20 | eFlour 450 | eBioscience | Lineage minus m | 1.75 ul | 0.5 ug/0.5 ml |
| CD66b | V450 | BD | Lineage minus m | 3.5 ul | 5 ul/0.25 ml |
| IgG1 | FITC | Biolegend | Isotype control | 7 ul | 0.5 ug/ml |
| IgG1 | PE | Biolegend | Isotype control | 3.5 ul | 0.2 mg/ml |
| IgG1 | PE-Cy7 | MilteniBiotec | Isotype control | 0.14 ul | 0.25 mg/ml |
| IgG1 | PE-CY5.5 | Biolegend | Isotype control | 0.8 ul | 200 ug/ml |

TABLE 6

Antibodies for innate cell panels (lineage negative antibodies were optional).

| Antigen | Fluorophore | Manufacturer | Function (m = marker) | Volume | Concentration |
|---|---|---|---|---|---|
| CD45 | APC | Biolegend | Leukocyte m | 1.5 ul | 0.06 ug/0.05 ml |
| HLA-DR | APC eflour 780 | eBioscience | Maturation m | 2.5 ul | 0.03 ug/0.5 ml |
| CD16 | PE | Biolegend | Monocyte and neutrophil m | 0.15 ul | 100 ug/ml |
| CD11b | Alexa fluor 488 | Biolegend | Monocyte and neutrophil m | 2.1 ul | 400 ug/ml |
| CD14 | QD655 | Invitrogen | Monocyte m | 0.1 ul | 1 uM |
| CD33 | PerCp-Cy5.5 | Biolegend | Monocyte and neutrophil m | 1.75 ul | 200 ug/ml |
| CD66b | V450 | BD | Granulocyte m | 3.5 ul | 5 ul/0.25 ml |
| ViViD | Vivid | molecular probes | Amine Viability m | 1.7 ul | Manufactures protocol |
| CD3 | Pacific Blue (Pac-bl) | Biolegend | Lineage minus Lin- m | 0.21 ul | 0.5 mg/ml |

TABLE 6-continued

Antibodies for innate cell panels (lineage negative antibodies were optional).

| Antigen | Fluorophore | Manufacturer | Function (m = marker) | Volume | Concentration |
|---|---|---|---|---|---|
| CD56 | Pac-bl | Biolegend | Lin- m | 2.8 ul | 400 ug/ml |
| CD19 | eflour 450 | eBioscience | Lin- m | 0.9 ul | 0.5 ug/0.5 ml |
| CD20 | eflour 450 | eBioscience | Lin- m | 1.75 ul | 0.5 ug/0.5 ml |

TABLE 7

Antibodies for Tumor Panel.

| Antigens | Fluorophore | Volume per 0.1 ml sample (ul) | Ab conc. (ug/ul) | Ab quantity (ug) |
|---|---|---|---|---|
| GFAP | Alexa fluor 647 | 0.8 | 0.05 | 0.04 |
| A2B5 | PE | 5 | 0.1 | 0.5 |
| Ki67 | PE-Cy7 | 0.3 | 0.2 | 0.06 |
| IL13Rα2 (Primary Ab) | — | 2.5 | 0.2 | 0.5 |
| Secondary Ab | Alexa fluor 488 | 0.2 | 1.25 | 0.25 |

Example 3. Developing Cytometric Assays for Tumor Infiltrating Leukocytes (TIL)

Three multicolor (7-8 color) staining panels were developed, identifying all prominent immune subsets within human brain tumors. The constructed lymphocytic, innate and DC staining panels target only cell surface markers, thus enabling live sorting of the identified cells.

Lymphocytic Panel

Figure 5A:
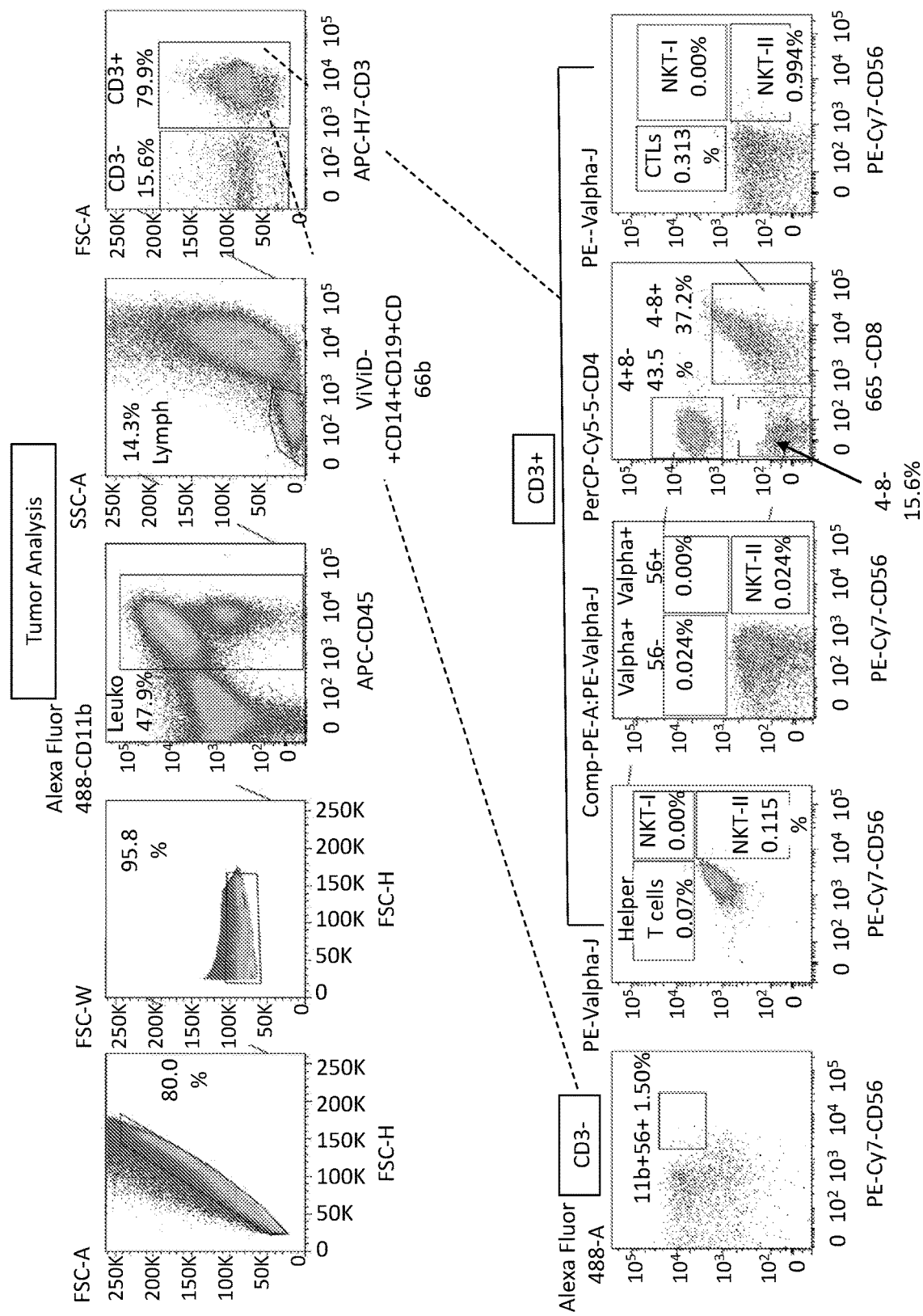
FIG. 5A-B. Analysis of the lymphocyte panels on a dissociated glioblastoma sample.

The first lymphocytic panel monitored the following markers: CD3, CD4, CD8, CD56, TcR-Vα24Jα18, CD45, CD11b, and a dump channel removing on the same fluorescent channel, dead cells-using a viability dye (ViViD) and unwarranted cells—$CD14^+$ monocytes/macrophages, $CD19^+/20^+$ B cells, and $CD66b^+$ granulocytes (see Table 4). As can be seen in FIG. 5A, the panel identified cytotoxic T lymphocytes—CTLs ($3^+8^+4^-56^-DUMP^-$), Helper T cells—Th ($3^+4^+8^-56^-DUMP^-$), $CD56^+$ NK cells ($3^-4^-8^{+/-}56^+$ $DUMP^-$) and NK-T cells ($3^+4^{+/-}8^{+/-}56^+Vα24^{+/-}$ $DUMP^-$) of 3 subtypes (Type1—iNKT:Vα24Jα18$^+$CD4$^+$ or CD4$^-$CD8-, and Type 2-NKT lacking the Vα24 Jα18 TcR).

In FIG. 5A, single cells dissociated from a glioblastoma (GBM) sample were stained with the Lymphocytic panel and serially gated. Top panels show (from left to right) two gates removing cell clumps and doublets; gating-in of intratumoral leukocytes ($CD45^+$); gating-out of macrophages ($CD14^+$) B cells ($CD19^+$), granulocytes ($CD66b^+$) and dead cells ($ViViD^+$); and gating for $CD3^+$ T cells/NK-T cells and for $CD3^-$ NK cells. Bottom panels show as follows. The $2^{nd}$ panel from right shows $CD4^+$ and $CD8^+$ gating. The three other connected $CD3^+$ dot plots further identify Th, CTL, iNKT-I and NKT-II. Left panel shows $CD3^-$ cells gated for intratumoral $CD56^+$ NK cells. Gate placement was aided by using the patient's blood cells (PBMC) stained with the identical staining panel.

Figure 5B:
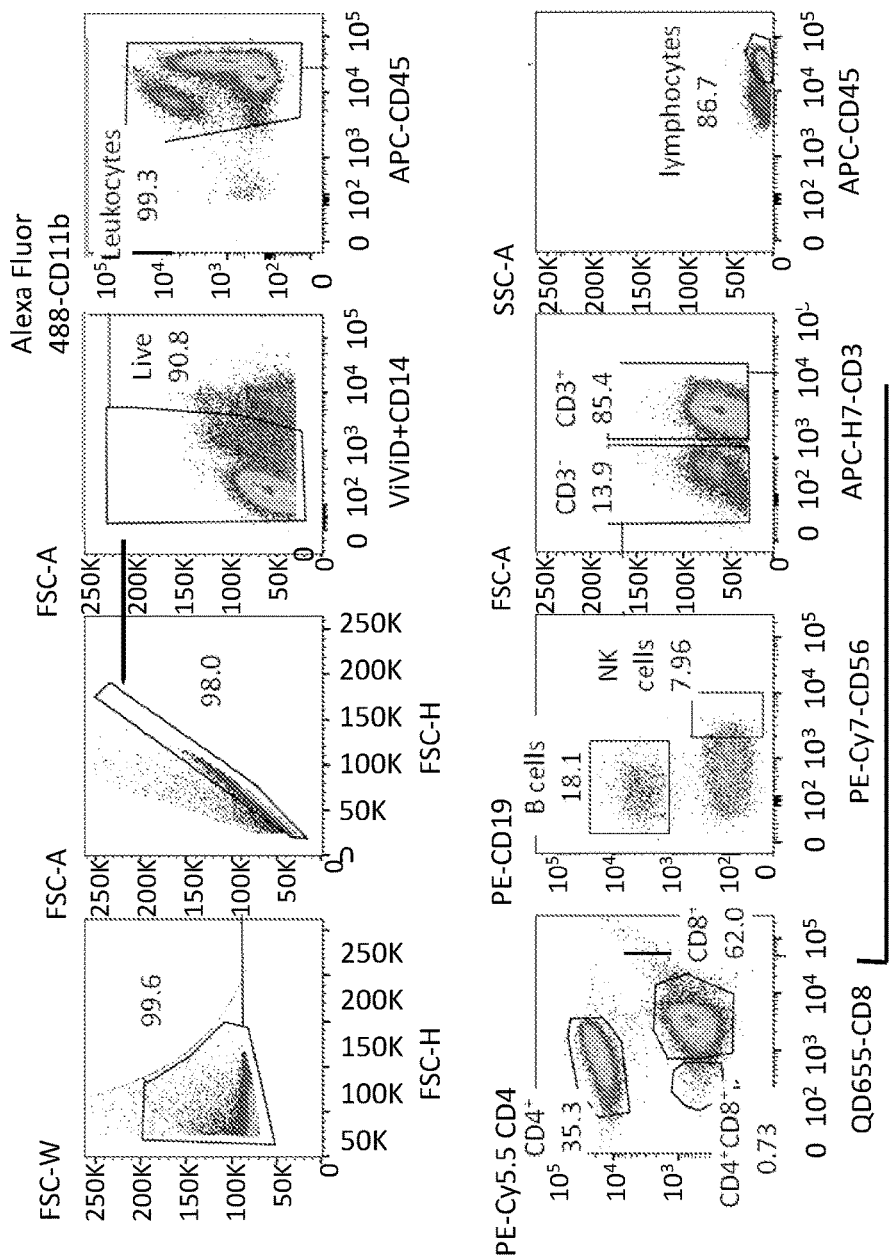
Figure 5B:
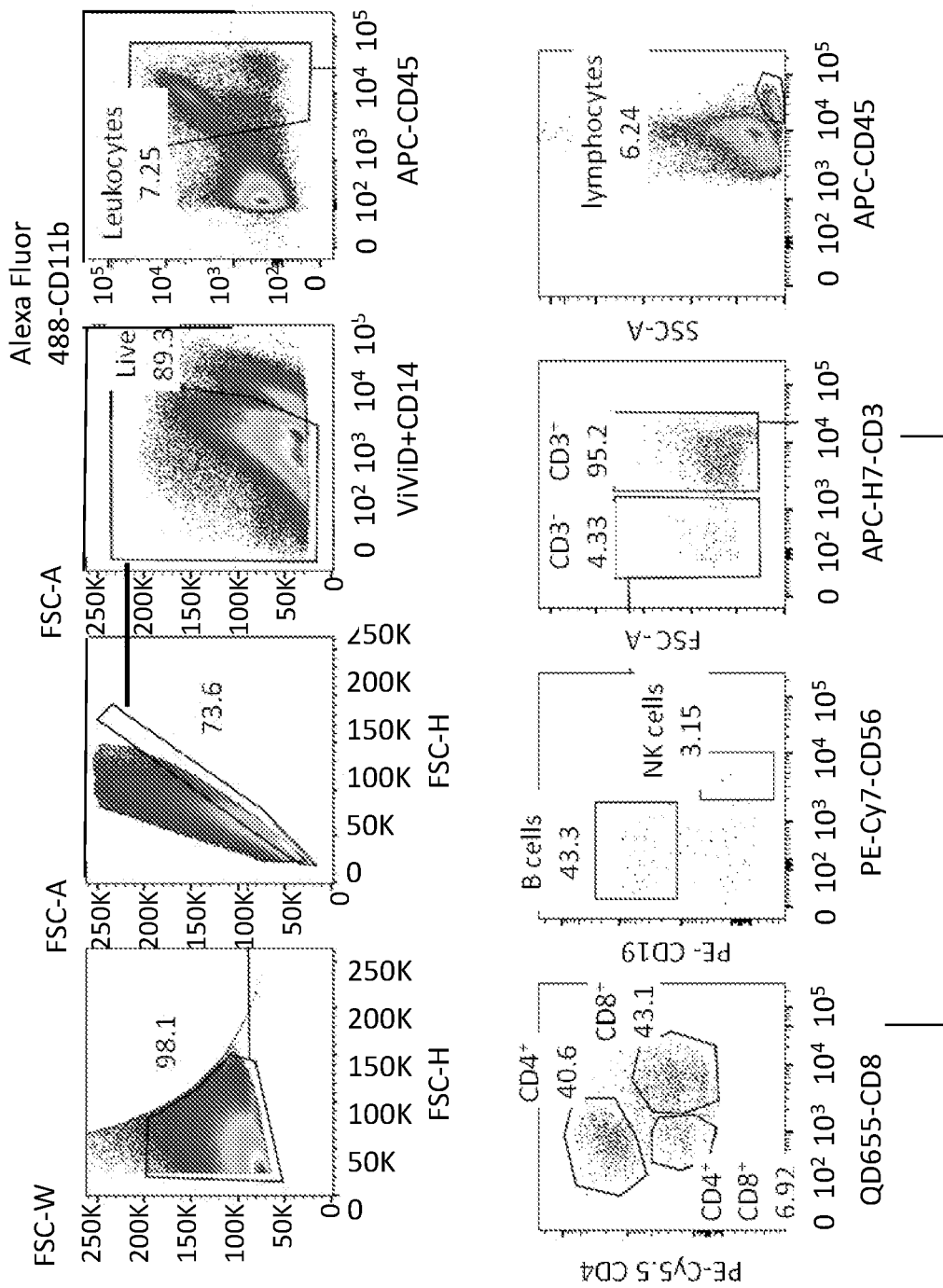

In other experiments, a second lymphocytic panel monitoring the following markers was employed: CD3, CD4, CD8, CD56, CD45, CD11b, CD19 and a dump channel removing on the same fluorescent channel, dead cells-using a viability dye (ViViD) and unwarranted cells—$CD14^+$ monocytes/macrophages, and $CD66b^+$ granulocytes (see FIG. 5B). This panel contained a PE-conjugated antibody directed to CD19, replacing the PE-conjugated antibody directed to TcR-Vα24Jα18, depicted in FIG. 5A. The second lymphocyte panel also lacked the eFluor 450-conjugated antibody directed to CD19, used in the first lymphocytic panel for the dump channel (lineage negative staining, see Table 4). In the experiments described in FIGS. 5A and 5B, the CD45 marker was used to "pull out" all immune stromal cells from the wide cloud of brain tumor (BT) cells which do not express the CD45 leukocyte marker. The inclusion of two markers (CD45 and CD11b) both in the lymphocytic panel and in the innate panel enabled easier comparison of the cellular data between the lymphocyte and the innate panels.

The inclusion of a dump channel removing both dead cell and unwarranted cells eliminated significant FCM artifacts and enabled the identification of γδ-T cells ($3^+4^-8^-56^-14^-19^-20^-$) within the tumors (see FIG. 5A). The panel's identification of γδ-T cells was confirmed as >90% of the cells expressed the γδ TcR when stained with a γδ TcR antibody in a separate panel.

Innate Panel

Figure 6:
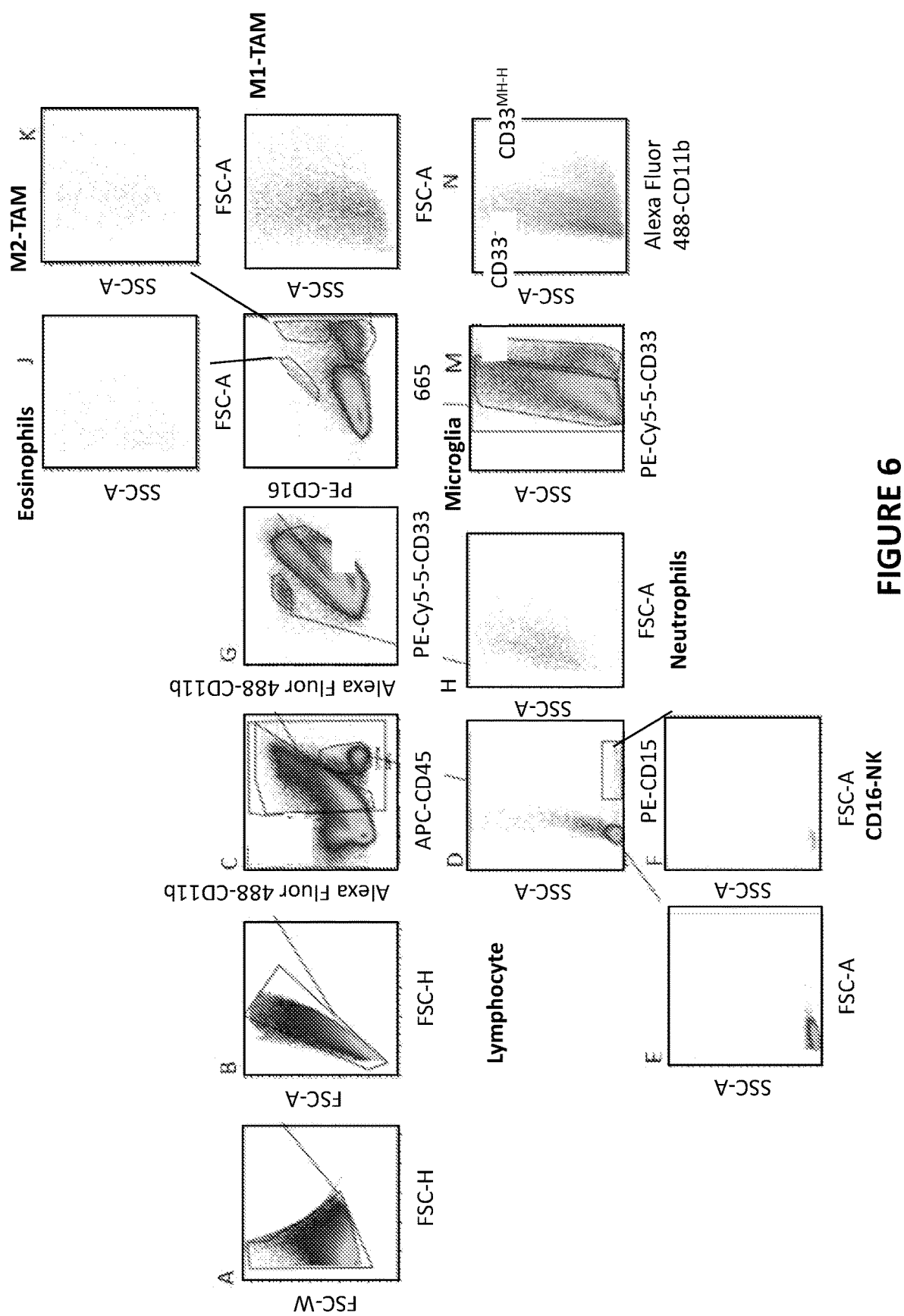
FIG. 6. Analysis of the innate panel on a dissociated glioblastoma sample.

Many of the immune suppressive elements reported for tumors are found within the innate immune compartment, however the identification of all intratumoral innate cells within a single tumor has not been adequately established. The innate panel was constructed to identify the following cellular targets: CD45, CD11b, CD14, HLA-DR, CD33, CD16, and CD66b/viability (see Table 6). The panel characterized all prominent innate intratumoral subsets apart dendritic cells (DC), which were specifically identified by DC panel. The innate panel identified tumor associated neutrophils (TANs), eosinophils, tumor associated macrophages (TAMs) of two activation states (activated-M1-like, deactivated and alternatively activated-M2-like), microglia (activated and non-activated), $CD16^+$ NK cells, and undefined lymphocytes (identified in the lymphocytic panel). FIG. 6 exhibits a multi-panel display of all innate subsets found within a single patient's GBM sample.

In FIG. 6, the innate panel was used to stain a patient's GBM sample, and the cells were gated in the following manner: panels A-B gated out the non-doublet/clumped single cells. C, lymphocytes and leukocytes which are not lymphocytes ("non lymph") were gated on CD45/CD11b. The gated lymphocytes were then divided (D) on CD16/SSC to NK cells (CD16MH-H/SSCL (F)) and the rest of the lymphocytes (CD16L (E)). NK and all other final-step gated cells are displayed on FSC to SSC. Non-lymph cells were gated on CD16/CD33 (G) for Neutrophils (CD33M CD11bH-(H)) and for other non-neutrophil myeloid cells (I). Non-neutrophil myeloid cells were gated on CD14/CD16, identifying Eosinophils (CD14MCD16MH-(J)), Microglia (CD14ML-MCD16LM (M)), M1-TAMs (CD14MH-HCD16L-ML(L)) and M2-TAMs (CD14HCD16ML-MH (K)). Both Neutrophils and Eosinophils display the highest CD66b levels (see FIG. 6). In graph (N) activated versus non-activated Microglia were separated as of their CD33 expression (activated CD33MH–H– right, non-activated CD33M– left). Activated microglia display lower FSC and SSC due to their ameboid shape with shortened processes, and upregulated HLA-DR (see FIG. 6).

This panel is unique as it is the first panel to identify human microglia. Due to the low resolution FCM used by other groups, microglia and macrophages are typically grouped together. As can be seen in FIG. 6, distinction between macrophages and microglia employing only the CD45 and CD11b markers, as reported in previous publications, result in, e.g. in a TAMs gate (CD45H and CD11bH) highly contaminated with neutrophils, eosinophils, activated microglia, and NKs. In contradistinction, the panels of the invention provide for isolation of highly pure cell populations.

Figure 7:
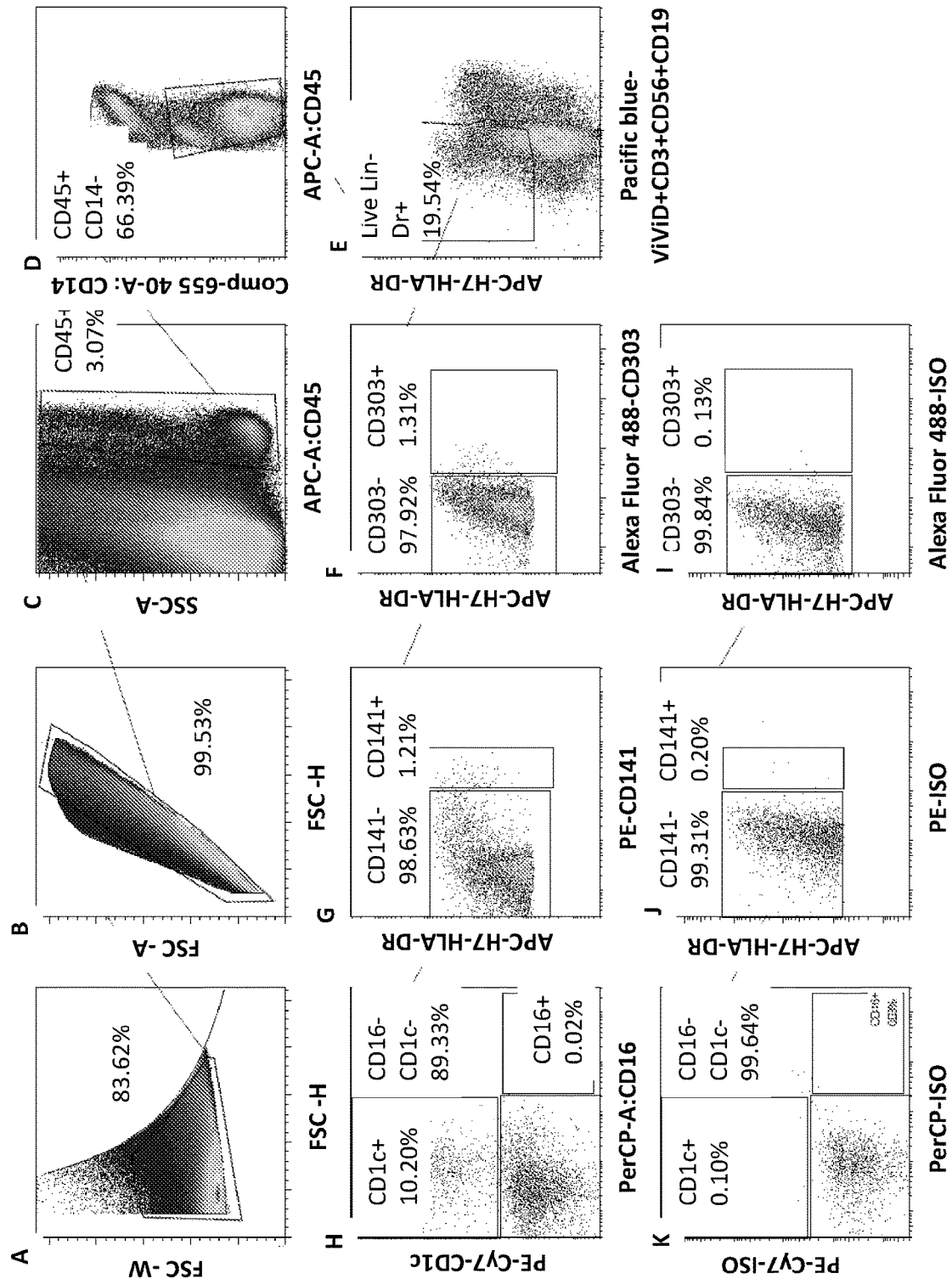
FIG. 7. Analysis of the DC panel on a dissociated glioblastoma sample.

In FIG. 7, cells were hierarchically gated: (panels A-B) singlet cells. (C) CD45+ cells (leukocytes). (D) CD14Med-Low. (E) Live Linage—DR+. Panels F to H identify the different DC subsets: CD303+ pDC, CD141+ mDC2, CD16+ mDC-CD16, and CD1c+ mDC1. Plots I to K show the FMO-Isotype controls for the staining. The frequencies of DC subsets out of total CD45+ cells were: CD303+—0.1%, CD141+—0.11%, CD1c+—1.27%, CD16+—0. As can be determined from FIG. 7, while all brain tumors contain microglia and TAMs, not all immune cells or DC subsets were found inside all brain tumors. The PBMC sample stained for DC panel served as a positive control—as in most or all cases, even in cancer patients, all DC subsets could be found in the blood, thus confirming the ability of the panel to identify the cells.

TABLE 8

The different marker levels displayed on the different innate cells recognized by the innate panel.

| Cell type | CD14 | CD45 | CD11b | HLA-DR | CD16 | CD33 | CD66b | FSC | SSC |
|---|---|---|---|---|---|---|---|---|---|
| Total Lymphocytes | L-ML | MH-H | L | L-MH | L | L | L | L | L |
| Neutrophils | L-M | M-MH | H | L | H | M | H | L-ML | M-H |
| Eosinophils | M | M-MH | M-H | MH | MH | M | H | L-ML | ML-H |
| M1-TAMs | MH-H | H (br-M) | MH-H (br-M) | MH-H | L-ML | MH-H | M-MH | ML | ML-H |
| M2-TAMs | H | MH-H | H | MH-H | ML-MH | H | MH | ML-H | M-H |
| Activated Microglia | ML-M | ML-M | ML-M | M-MH | L-M | MH-H | ML-MH | L-ML | L-MH |
| Non-Activated Microglia | ML-M | ML-M | ML-M | M-MH | L-ML | M | ML-M | L-M | L-H |
| NK | L-ML | H | L-ML | L | M-MH | L | L | L | L |

In Table 8, H indicates high, M indicates Medium, and L indicates low levels of the marker compared to the levels in the entire leukocyte population (and to other distinct subpopulations identified). Wherever more than three expression levels exist—medium high (MH) and medium low (ML) levels were further used.

DC Panel

The distinction between myeloid DC-1 (mDC1), mDC2, mDC-CD16 and plasmacytoid DC (pDC)) within human tumors has yet not yet been established. An 8-color/12-marker DC panel was constructed, which identified all four DC subsets within brain tumors. The panel monitored the following markers: CD45, CD14, HLA-DR, Viability+Lineage markers (CD3/19/20/66b), and specific DC-subset markers: CD1c for mDC1, CD141 for mDC2, CD16 for mDC-CD16, and CD123 (or CD303 or CD304) for pDC (see Table 5). FIG. 7 depicts serial gating of intratumoral DC. As the numbers of DC are limited (frequently 10$^{-3}$ to 10$^{-5}$ per specific DC subset) gating of these infrequent cell populations within brain tumors is challenging. Two measures were employed to ensure correct intratumoral DC gating. The first was to run the DC panel on PBMC from the same patient, resulting in more reliable placing of the gates, which can then be used to identify intratumoral DC populations. The other measure to ensure correct gate placement was using a 'Fluorescent-minus-one' (FMO)-Isotype control. The cells were stained with an entire DC panel but the four mutually-exclusive DC-subset markers, which were exchanged with equivalent concentrations of their respective isotype controls (FIG. 7).

Example 4. Sorting and Further Characterization of Intratumoral Immune Cells

Figure 8:
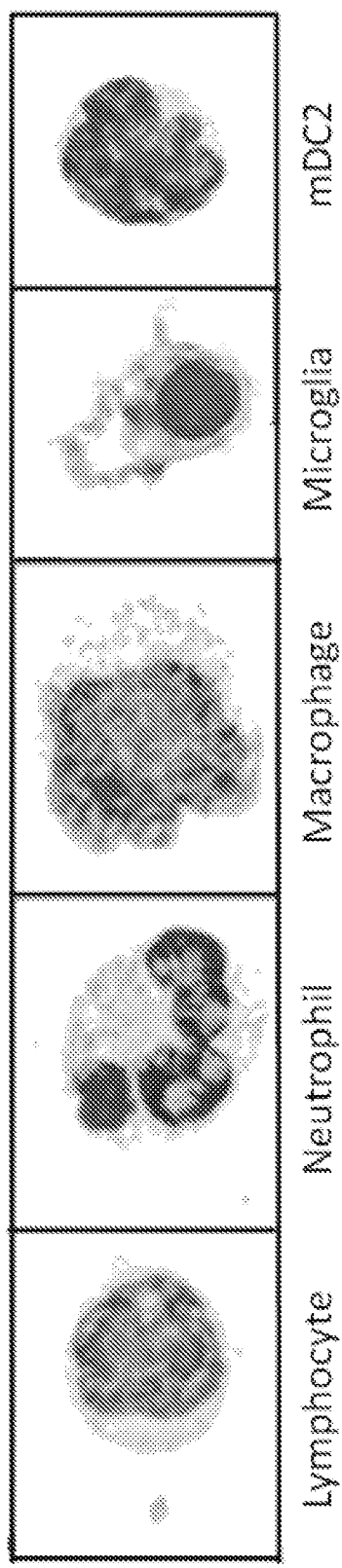
FIG. 8. Cells sorted from a human GBM sample. Live cells were applied to slides and stained using Giemsa and May Grunwald.

Cells from tumors were sorted using the FACS-Aria flow cytometer. Cells were four-way sorted into HBSS containing 20% FCS when the cells were used for microscopy or in functional assays. FIG. 8 depicts cells sorted from a human GBM sample, centrifuged to slide and stained with May Grunwald and Giemsa staining. In FIG. 8, intratumoral immune cells from human GBM were sorted by flow cytometry using the panels described above, stained and photographed microscopically using ×100 amplification. The identity of the sorted cells was confirmed by a hospital hematologist. (A) Lymphocyte, (B) tumor associated Neutrophil (TAN), (C) tumor-associated macrophage (TAM) and (D) Microglia and mDC-2. Cells used for gene expression assay were sorted directly into Trizol. RNA purification from minute number of cells (≥100) was achieved with the aid of glycoblue RNA co-precipitant (Invitrogen). Real-time PCR was performed for the normalizing gene Rplpo normalizing gene expression following RNA extraction from 100-10,000 cells. RNA extracted from 10,000 to 100 cells was reverse transcribed to cDNA and amplified with primers for the normalizing gene Rplpo. The resulting amplification plot exhibited amplification of cDNA from the cells and from non-template control (NTC). Melting curves exhibited single identical products for all non-NTC groups.

Example 5. Immune Patterns Correlated with Tumor Severity

Tumors from GBM patients were stained using the innate, DC and lymphocytic staining panels. Samples were read using Canto II flow cytometer. The number of cells in each subpopulation was divided by the total number of nucleated cells in the sample or by the total amount of leukocytes (CD45$^+$ cells). Resulting data, spanning several logs of magnitude, underwent log transformation and were given a score on a 1-10 scale where 10 represents the highest relative frequency observed for the specific cell.

Figure 9:
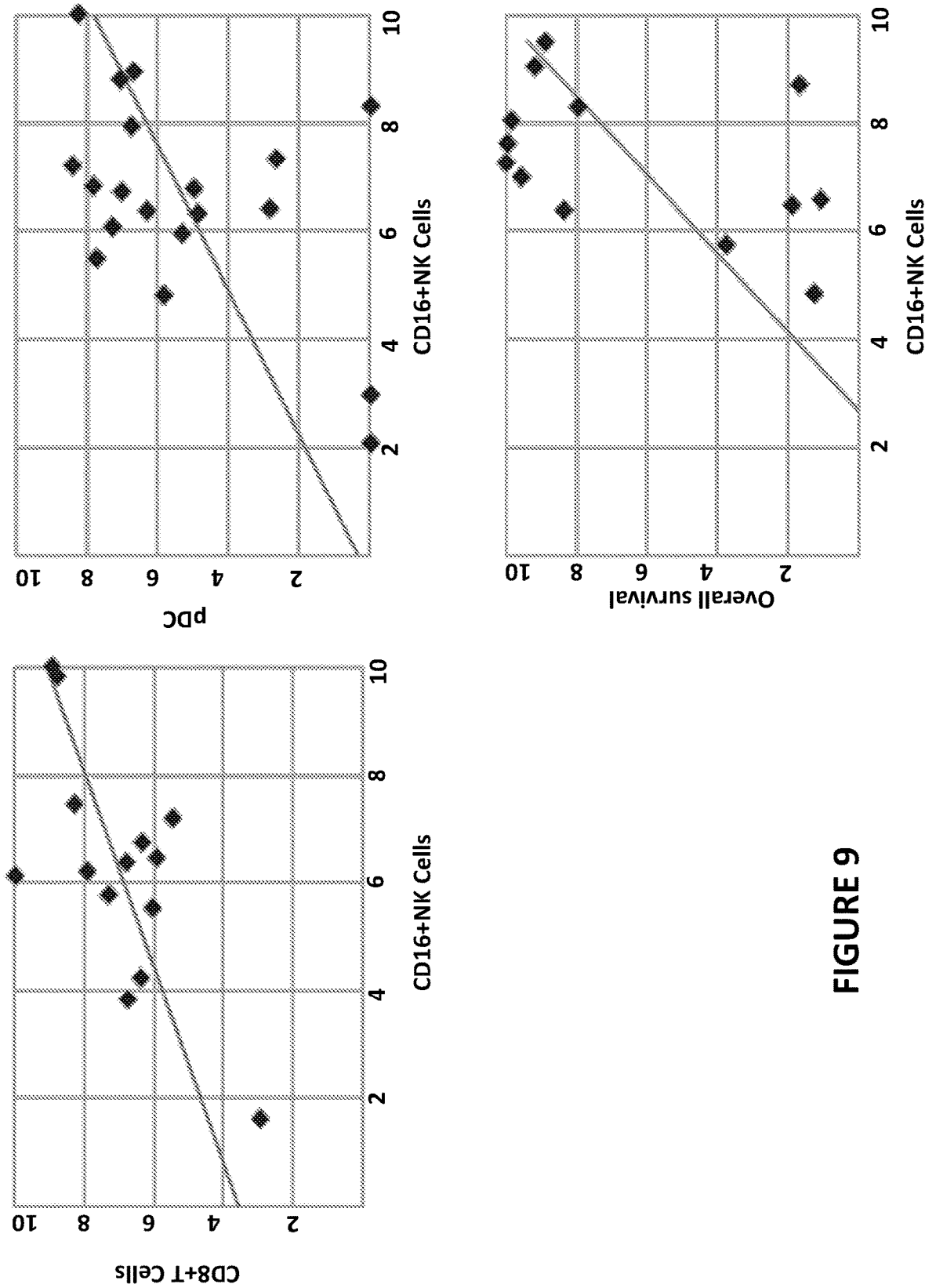
FIG. 9. Correlation between intratumoral CD16$^+$ NK cells and CD8$^+$ T cells, pDC and overall survival (OS).

Overall survival (OS) of patients was scored on a 1-10 scale, based on OS presented by publications of patients treated with standard chemoradiotherapy. For example, a score of 9 meant that 90% of patients had survived less than the scored patient. The correlation between every two populations of immune cells and between each immune cell population and OS were examined. As can be seen in FIG. 9, among the correlations found, the log-transformed intra-tumoral infiltration score of CD16$^+$ NK cells (identified by the innate panel) correlated positively with that of CD8$^+$ T cells (identified by the lymphocytic panel), with that of pDCs (DC panel) and with overall survival of patients. In addition, the following findings were observed: PDCs (CD303) were found significantly higher in high grade glioma (HGG) patients as compared to epileptic patients with an 18 fold increase (P=0.04). Similarly, a trend toward a significant increase in pDCs was found in metastasis samples in comparison to epileptic brain samples showing an overall increase of pDCs in all tumorous lesions inside the brain, either primary or metastasis. CD141-mDC2 were found in lower proportions in low grade glioma (LGG) patients versus all other tumorous and non-tumorous samples, with a 24 fold decrease (P=0.02) in comparison to metastatic samples. CD16-mDC appeared in higher proportions in LGG brain tumor (BT) samples. CD16-mDC of LGG were ×1.8 higher than in epileptic brain samples, ×33 higher than metastasis samples and ×7.6 higher than HGG. In some cases, due to the relatively low sample size and the high inter-sample variability, significance was not yet reached. Note that the results are not due to entrapment of blood inside the brain sample received, as proportions that were found different in brain tissues (e.g. in LGG versus HGG) were dissimilar to their PBMC counterparts, and in some cases some populations found in blood were not present in brain tumors. Thus, low mDC2 and high CD16-mDC was identified in LGG versus high mDC2 and low CD16-mDC in HGG.

Example 6. Cytometric Assay for Brain Tumors

I. Materials and Methods
Human Subjects.

Patients' brain tumors, peripheral tumors metastasizing to the brain, and epileptic foci were removed at craniotomy at the Tel-Aviv Medical Center. The excised brain tissues were pathologically classified by neuropathologists. The study was conducted following institutional review board approval, and tissues were obtained from patients who signed an informed consent. Brain tissue dissociation to single cells. Freshly isolated brain or tumor tissues were transferred to the lab in saline or in Ringer lactate (Biological Industries, Beit HaEmek, Israel). Blood clots and necrotic pieces were discarded, and the cleaned tissue was weighed and cut into ≤2 mm pieces using surgical scissors. The tumor pieces were re-suspended in HBSS$^{(+Ca\ +Mg)}$ without phenol red (Biological Industries) at 100 mg dry tumor per ml. The tissue was subjected to enzyme dissociation for 2 hours to overnight (ON) using neutral protease (NP)—from Ch (AMSBio-Abingdon, UK) at 0.6 mg/ml. Following incubation, the tumor tissue was triturated using a Pasteur pipette (Biologix, Zouqu, China). The collected cells were briefly mixed and the undigested debris was collected from the bottom of the tube and discarded. The cells were then washed twice with PBS$^{-Ca\ -Mg}$ (PBS) (Biological Industries), and a sample of the cells was stained with trypan blue (Sigma, St. Louis, Mo., USA) and counted.

Cell Surface, Intracellular and Intranuclear Staining of Cells.

Dissociated cells were adjusted to 0.5-2×10$^6$ cells per 100 µl in PBS and stained in room temperature (RT) in the dark in the following manner: 1. Cells were stained for 10' with ViViD (violet viability dye), an amine-reactive fixable viability dye (Molecular Probes, Invitrogen, Eugene, Oreg., USA) according to manufacturer's protocol. 2: Cells were washed (in PBS) and blocked with 5% FCS in PBS for 15'. 3. Cells were washed and extracellularly stained for 20' with IL13Rα2 primary goat antibody (R&D, MN, USA) and with A2B5-PE antibody (Clone 105-HB29, Miltenyi, Bergisch Gladbach, Germany). 4. Cells were washed and stained for 20' with secondary bovine anti-goat Ax488 antibody (Jackson, West Grove, Pa., USA). 5. Cells were washed and then fixed and permeabilized using Fix/Perm+Perm/Wash kit (BD Biosciences, Franklin Lakes, N.J., USA) according to the manufacturer's protocol. 6. Cells were washed twice with the Perm/Wash buffer, then blocked for 15' with 2% normal mouse serum (eBioscience, San Diego, Calif., USA). 7: Cells were washed with the Perm/Wash buffer and stained for 30'-40' intracellularly with GFAP-Alexa647 (Clone IB4, BD) and intranuclearly with Ki67-PE/Cy7 (Clone SolA15, eBioscience). 8. Cells were washed with Perm/Wash, then fixed using 250 µl of 1% formaldehyde (Electron Microscopy Sciences, Hatfield, Pa., USA) diluted in PBS. 9: Cells were kept in 4° C. in the dark for up to 72 hours, and read on a Canto-II flow cytometer (BD biosciences). 10: An Isotype panel was used to evaluate the background staining of the cells. The Isotype panel was stained identically to the Tumor panel, but all the fluorochrome-coupled antibodies were exchanged with identical concentrations of their respective isotype control fluorochrome-coupled antibodies. The background for IL13Rα2 staining was attained by staining with the secondary bovine anti-goat Ax488 antibody only.

Flow Cytometry (FCM) Compensation Controls.

A singly-stained compensation (COMP) bead control (BD biosciences) was prepared for each fluorochrome. ArC, amine-coated compensation beads, (molecular probes) were stained with ViViD and served as controls for the viability dye. The compensation controls were used to calculate a multicolor compensation matrix using the DIVA software or post-hoc using the Flow-Jo flow cytometric analysis package (Tree Star, Ashland, Oreg., USA). All FCM analysis was done using Flow-Jo. Percoll-gradient purification. A 50% iso-Percoll mix was prepared by mixing PBS and iso-Percoll ((9-parts Percoll (GE Healthcare, Uppsala, Sweden) mixed with 1-part PBS×10 (Biological industries)) mixed at 1:1 ratio. Eleven ml of 50% iso-Percoll were dispensed to 15 ml tubes that were run on a super-speed centrifuge with a fixed angle rotor at 20,000 g for 60' at 20° C., break-off to generate a continuous gradient. The prepared gradients were then gently overlaid with 3 ml of up to 0.5 grams of dissociated tumor cells. One gradient was overlaid with 2.9 ml of medium, to which 100 µl density beads (GE Healthcare) were added in order to identify layer densities. Gradient tubes loaded with cells were centrifuged at 3000 rpm in a swing-rotor centrifuge for 20' at 20° C., break-off. The location of the different density beads was recorded and the cells found at different density layers were collected into serum-coated tubes to avoid sticking. The cells were then washed twice using medium (e.g., RPMI) at 1600 rpm. Last wash before FCM staining was done using PBS at 1200 rpm.

II. Tissue Dissociation Using NP Produces Viable Cells and Clean Cell Mixtures.

Inefficient or overly aggressive tumor dissociation may generate minor to almost complete loss of cell viability. Efficient dissociation is crucial when running FCM analysis or FCM-sorting procedures that are dependent on the quality of cell mixtures. As described herein, a panel of over 40 resected BTs and brain tissues were dissociated to single cells by mechanical dissociation, or by mechanical and enzymatic dissociation. All frequently used dissociation enzymes were evaluated, i.e. collagenase, DNase, hyaluronidase, papain, and dispase. Neutral Protease (NP) from Ch, yet not evaluated on brain tissues, was also evaluated. The single-cell-dissociated cell mixtures were evaluated both for cell viability and for the cell-mixture quality. Viability was evaluated by trypan-blue and using a flow-cytometric viability dye. Cell mixture quality was graded for the amount of generated subcellular debris, non-dissociated cell clumps, and spilt DNA.

From all enzymes or enzyme combinations, NP produced dissociated cell mixtures with highest cellular viability: gliomas—93%, brain metastases—85%, brain tissues—89%. NP also produced mixtures of the highest quality with significantly less debris than the second best enzyme, dispase. Dissociation using NP was gentle over time and no changes to cell viability or mixture quality were found comparing 2-hour dissociation at 37° C., to overnight (ON) dissociation at ambient temperature. Thus, NP, an enzyme that is available also in clinical grade allows for gentle yet effective dissociation of viable single cells from brain tissues and tumors. Its non-aggressive dissociation may also allow for ambient-temperature shipping of tumor pieces in multi-center clinical trials, meanwhile being dissociated. Single cells of higher quality and viability may enable better science by avoiding experimental artifacts associated with dead cells or cellular debris. Larger yields of high quality cells may also contribute to the success of cell-therapy clinical trials in neuro-oncology.

III. Selection of Antigens to be Monitored by FCM to Identify Glioma Cells

As no single antigen can distinguish glioma cells from other brain cells, neuropathologists classify astrocytic tumors as such if they exhibits both astrocytic markers and they aberrantly proliferate. Astrocytic tumors, and some oligodendrial and ependymal tumors, express glial fibrillary acidic protein (GFAP), an intra-cytoplasmic glia-specific marker. Proliferating cells all express Ki67/MIB-1; an intra-nuclear protein expressed during the active phases of cell cycle (i.e., $G_1$, S, $G_2$ mitosis), but not in $G_0$ resting cells. Mitotically-quiescent cells constitute the vast majority of the postmitotic cells in the adult brain. Although Ki67 alone cannot identify "a glioma cell", in the panel it serves as an 'anchor' antigen defining a "tumor cell". Ki67 is a prognostic parameter that negatively correlates with the survival of BT patients. Two other glioma markers that were incorporated into the tumor panel are IL13Rα2 and A2B5. IL13Rα2 is a glioma associated antigen (GAA), reportedly expressed by 60-80% of gliomas. Other cells in the brain express it weakly or not at all. IL13Rα2 was used in several clinical trials to target cytotoxins to glioma cells.

A2B5 is a protein expressed by bipotent glial progenitor cells and in 60%-100% of human gliomas. A2B5 expression is associated with glioma chemoresistance and may define a 'tumor-initiating cell' (i.e. "cancer stem cell") better than the more frequently used marker—CD133. Other GAAs, such as CD133, EGFR, CD24, CD44, transferrin-R and IL4-R, may also be used as GAAs. IL13Rα2 and A2B5 were selected over these other markers for their higher prevalence and as herein identified to have stronger or clearer expression than the other markers tested, specifically, transferrin-R, EGFR, and CD24.

IV. Monitoring the Antigen Expression—the Necessity of a Viability Marker.

Figure 10:
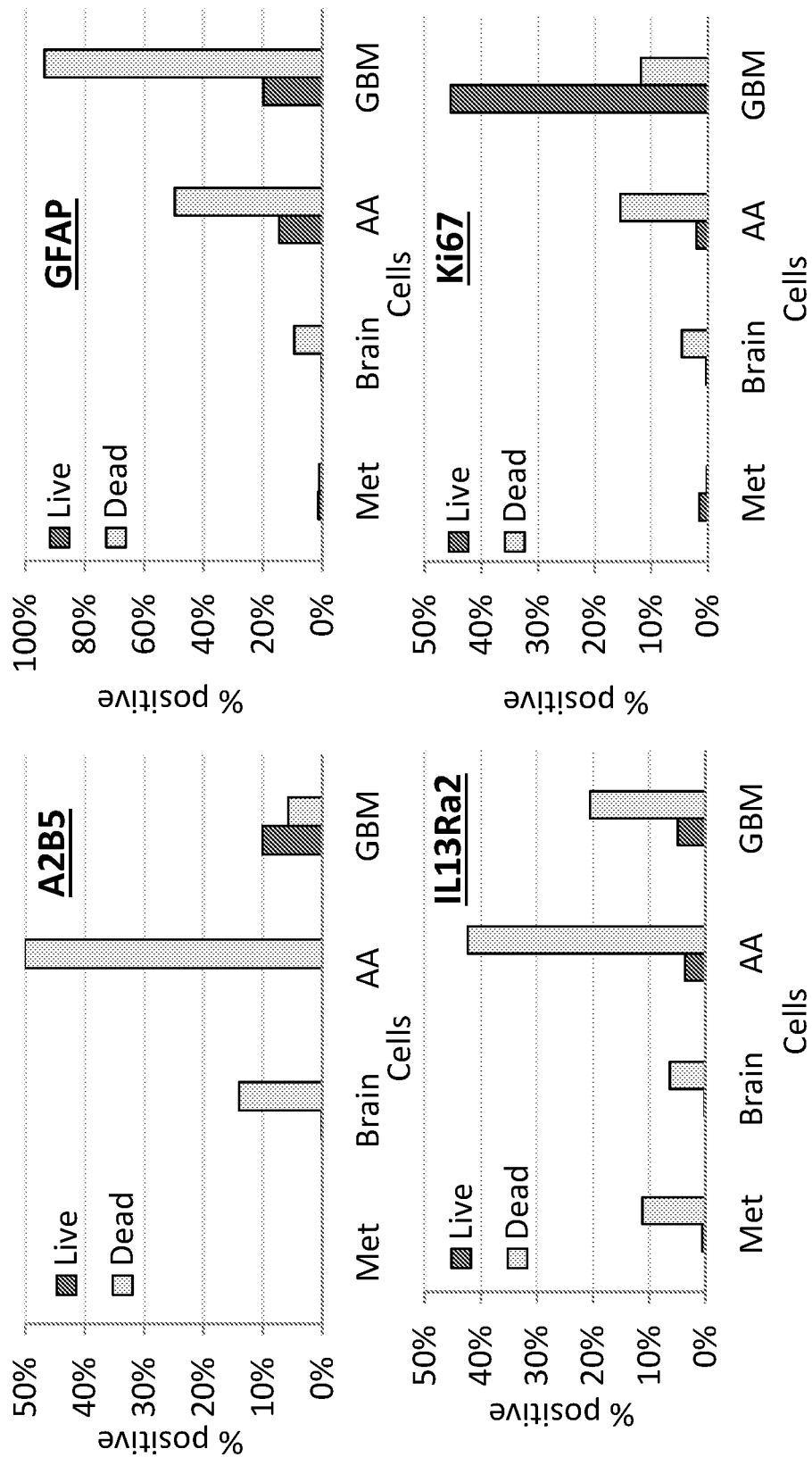
FIG. 10. glial marker expression patterns of live (ViViD low) versus dead (ViViD-high) cells, showing major staining artifacts can be found when cellular viability is not evaluated.
Figure 11:
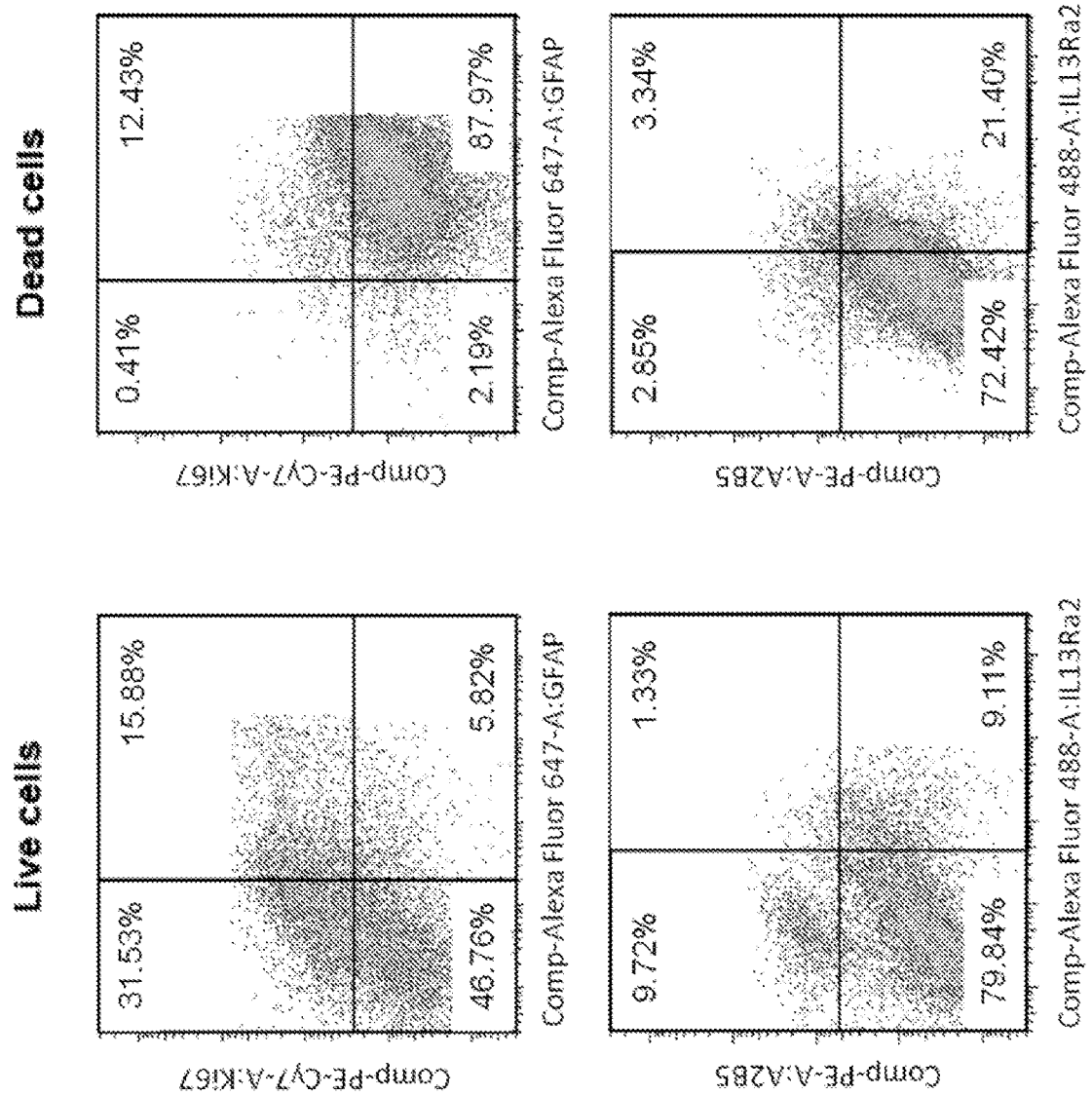
FIG. 11. Dot plots of live (ViViD low) and dead cells (ViViD high) antigen expression patterns from the same dissociated tumor sample showing that dead cells are non-specifically and potently stained.

ViViD, a dye staining amine groups within the cytoplasm of damaged cells was used as a viability marker. Differently from older viability dyes, (e.g. PI and EMA) amine dyes can be fixed without loss of signal, and can be used to prepare compensation controls using amine-coated beads. FIG. 10 depicts the percent positive cells for the evaluated antigens in brain and BT samples: a GBM (grade IV astrocytoma), an anaplastic astrocytoma (AA) (grade III astrocytoma), an epileptic brain focus, and lung metastasis to the brain. Samples stained with the Tumor panel were gated as depicted in FIG. 11. The gate defining positive staining was plotted by comparing the staining between the Tumor panel and the Isotype controls panel for the tumor panel. FIG. 10 demonstrates that live cells exhibit antigen expression patterns that are almost unrelated to their dead cell counterparts. For example, while 50% or 94% of dead cells in two astrocytic tumors (glioblastoma-GBM and anaplastic astrocytoma-AA, respectively) expressed GFAP, only 15% or 20% of their respective live-cell counterparts expressed GFAP. In the case of Ki67, the dead AA cells stained stronger (16%) than their live-cell counterparts (3%); in contrast, the dead GBM cells stained weaker (12%) for Ki67 than their live-cell counterparts (46%). The A2B5 exhibited strong expression on dead brain cells (14%) and dead AA cells (50%), but was hardly expressed A2B5 (~0%) on their respective live-cell counterparts.

FIG. 11 follows marker expression of live versus dead cells. The serial gating of GBM cells was done as follows: The two top left panels gate cells on forward scatter (FSC) height (H) to FSC-width (W) and then on FSC-H to FSC-area (A), gating-in single cells (singlets, sin) and gating-out cell-doublets and cell clumps that cause significant FCM artifacts. The next four gates gate-out oversized, over-granulated (high side scatter-SSC) and over-stained cells, i.e., cells which lay on the top axis. The rightmost gate in the second row is the live/dead ViViD gate, thus preventing incorrect compensation of the "over-stained" cells (cells accumulated on the ends of axis). The bottom four panels depict the staining of live cells (ViViD$^{dim}$, A+C) and dead cells (ViViD$^{bright}$, B+D) for Ki67/GFAP (A+B) and for A2B5/IL13Rα2 (C+D). The dead cells and their live cell counterparts exhibited almost unrelated staining patterns. The staining discrepancy does not represent a biological phenomenon, but the tendency of monoclonal antibody conjugates to stick nonspecifically to dead cells. The antigen expression in dead cells is inconsistently higher or lower in comparison to their live cell counterparts, or may even "appear" where no expression was found in live cells. Taken together a viability marker is an advantageous and in some embodiments crucial component of the panels. The lack of use of a viability marker, together with the possible large numbers of dead cells that are produced by some dissociation protocols, may account for the large inconsistencies in different reports on tumor markers expressed by BTs.

V. Troubleshooting the Staining Procedure for the Tumor Panel During the construction of this panel, technical problems have risen. The section below lists problems identified under the experimental conditions tested. Ki67 staining: An initial attempt to intranuclearly stain for Ki67 using the 20Raj1 antibody clone coupled to a relatively weak fluorochrome (PerCP-eFluor710), in which no detectable staining was attained. In contrast, the SolA15 clone coupled to a stronger (PE-CY7) fluorochrome exhibited excellent staining indices enabling clear identification of Ki67$^+$ proliferating cells. Cellular and nuclear permeabilization: BD's Fix/Perm buffer and eBioscience's (FoxP3) transcription factor staining buffer were tested for their ability to allow concurrent staining of extra-membranal, intracellular and intranuclear antigens. Of these buffers, Fix/Perm provided the favorable concurrent staining for all tested antigens. IL13Rα2 staining: An antibody panel containing only fluorochrome-coupled monoclonal antibodies is preferable to using a panel combining primary and secondary antibodies. Initially, a PE-coupled mouse monoclonal antibody (clone B-D13) to IL13Rα2 was tested. Two batches of Abcam's antibodies of this clone did not exhibit specific binding to tumor cells. In contrast, R&D's primary goat polyclonal primary antibody to IL13Rα2 exhibited specific binding on dissociated BT cells. The secondary donkey anti-goat antibody used with the goat polyclonal antibody that was initially used to bind the primary goat antibody exhibited very high background staining (~10%). This was supposedly due to unspecific cross reactivity of the donkey antibodies to remnants of the bovine-fetal calf serum (FCS) used for cell freezing the cells. Changing the secondary antibody to bovine anti-goat antibody significantly reduced the staining backgrounds (0%-2.5%) (see FIG. 12). Blocking: Several commercial Fc-receptor blockers (antibodies or peptide blockers) were used to reduce the staining backgrounds as well as any irrelevant secondary antibody binding through Fc. None exhibited any beneficial effects on staining backgrounds. The use of mouse and bovine sera at the relevant stages before staining with mouse antibodies and before staining with bovine antibodies, respectively, (see materials and methods) significantly reduced the staining backgrounds. Antibody calibration: Antibodies were calibrated to produce the highest signal-to-noise ratio. The optimal antibody concentrations were found to be lower than those recommended by the company data sheets. Use of an isotype control panel: Correct definition of the staining background requires at least one of the following controls: a biological control, a fluorescence minus one (FMO) control, or a full isotype control panel. A Biological control is not applicable in these settings. According to some embodiments, an FMO control that omits one antibody from a full panel to determine the staining background is adequate for monitoring a single well-defined cell subset, but not for determining the background staining of mixture of cells found inside a tumor, where each population has a different background staining and unspecific binding. A full isotype control panel was used to determine the background staining for the dissociated cell mixture. By defining where the unstained cells are, the gate for the stained cells could be placed more correctly.

Autofluorescence:

Autofluorescence (AF) is exhibited by a diagonal "tail" of cells found in some of the dot plots. AF is a trait of the cells, and not due to cell staining, thus it cannot be corrected by means of compensation matrix. The use of an isotype control panel cannot solve the AF problem, but may enable identification and quantification of AF.

Figure 12A:
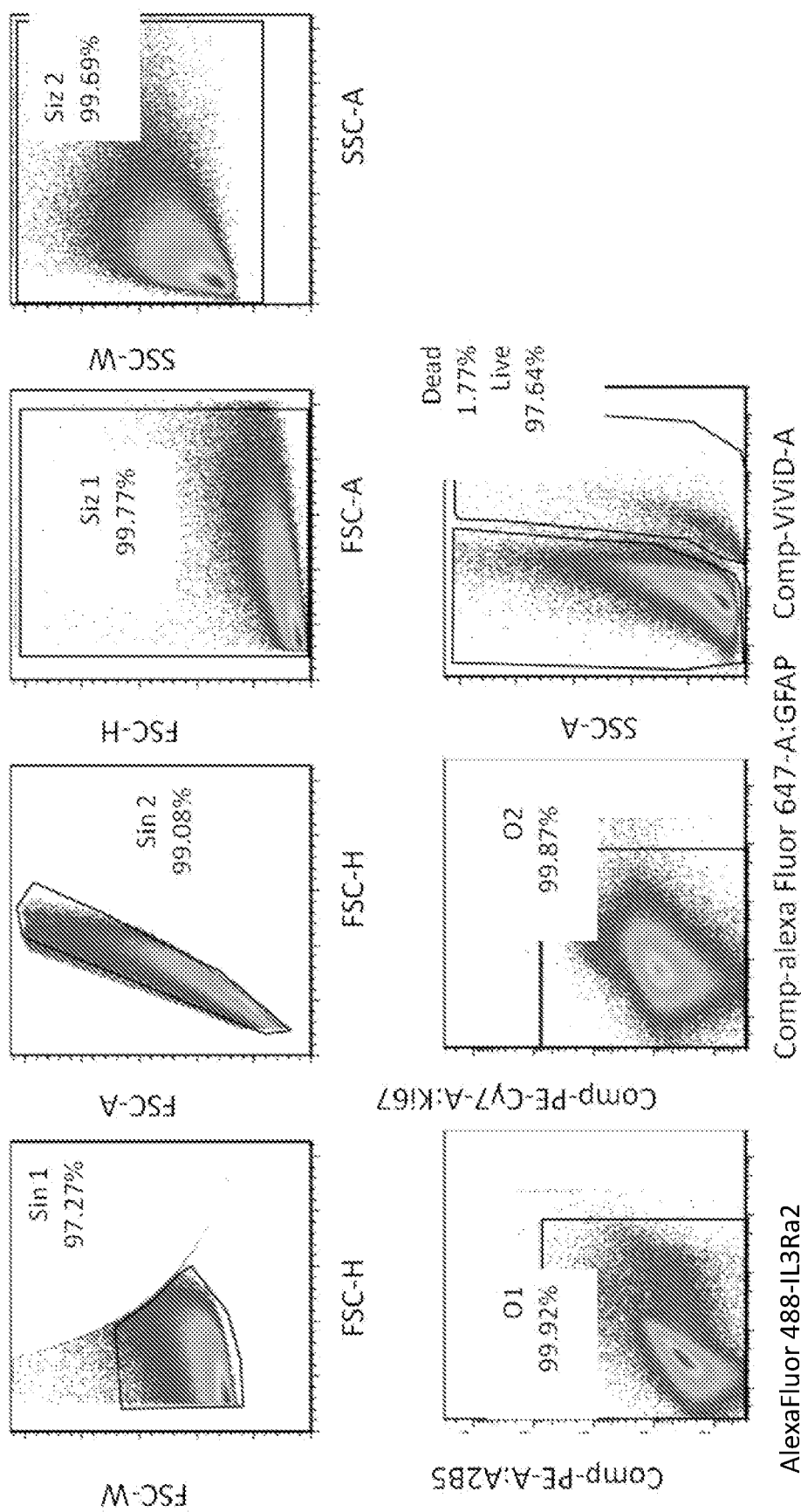
Figure 12B:
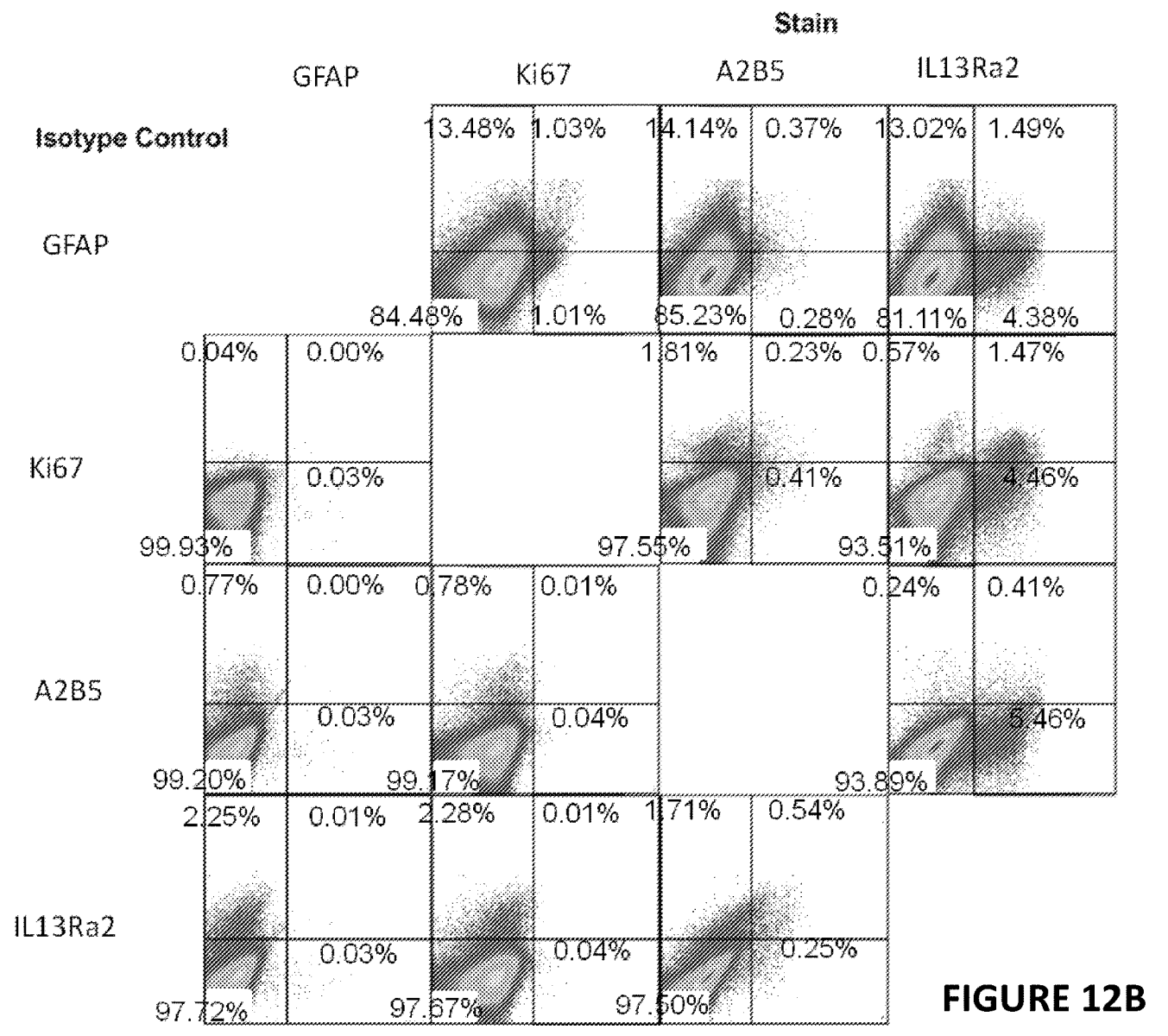

VI. Determining Antigen Co-Expression Pattern Using Flow Cytometry FIG. 12A-B depicts representative serial gating of AA cells stained using the Tumor panel. FIG. 12A shows the initial steps of analysis. Top panels from left to right: removing doublets and clumped cells, then cells stacked on the top axis for FSC, SSC and fluorescence, which may create, some staining or compensation artifacts (also shown in bottom left and bottom middle panels); bottom right panel shows gating for ViViD-positive dead cells and ViViD-dim live cells. FIG. 12B displays six dot plots of Tumor-panel stained cells (top right) and six dot-plots of Isotype panel-stained controls (bottom left). The Tumor and the matching Isotype panel are arranged as diagonal mirror images. Following all background reduction steps detailed above, the full isotype control panel showed close to zero background levels for Ki67 or GFAP, and 0.8% and 2.3%, staining background for A2B5 and IL13Rα2 respectively in the representative sample. This variability in staining background highlights the necessity of an Isotype panel. The staining background percent (that include the AF cells) were subtracted from the respective tumor panel-positive percents to attain the true positively staining cells. In the depicted AA sample in FIG. 12A-B, there were no A2B5$^+$ cells, 2% Ki67$^+$ cells, 3.6% IL13Rα2$^+$ cells and 14.5% GFAP$^+$ cells. The dot plots reveal important information on the markers co-expressed by various cell populations. For example, the Ki67/IL13Rα2 dot-plot shows two subpopulations of cells positive for IL13Rα2, one which was negative for Ki67 and the other one which was positive. Conversely, 72% of the Ki67$^+$ proliferating population was positive for IL13Rα2, but the rest of the Ki67$^+$ cells (0.54%/2.04%) did not express IL13Rα2. The proliferating cells of the AA also co-expressed GFAP (50%) and A2B5 (26%).

VII. Multi-Parametric Evaluation of Antigen Co-Expression

Figure 13A:
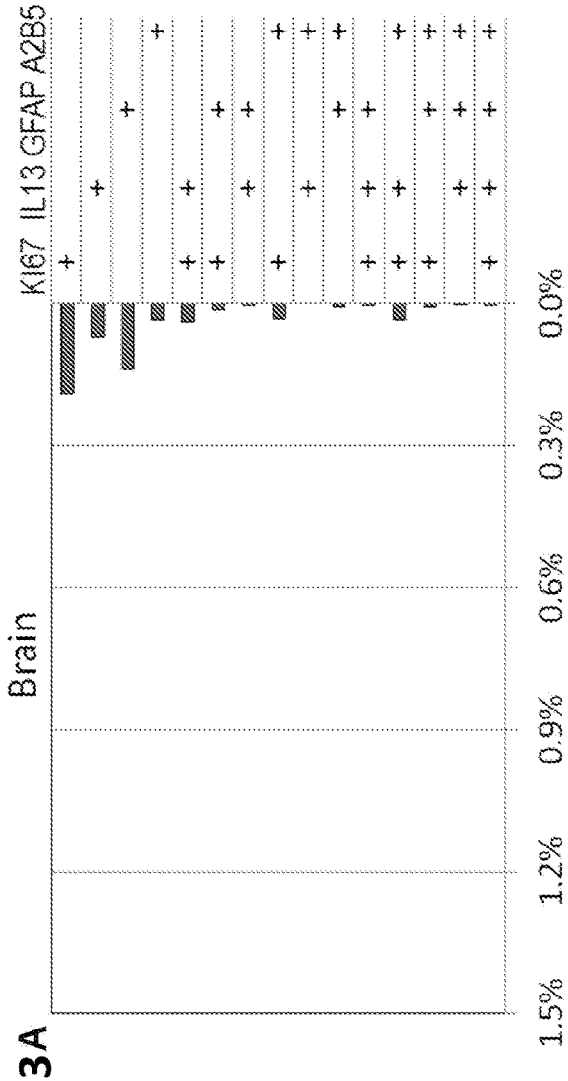
Figure 13B:
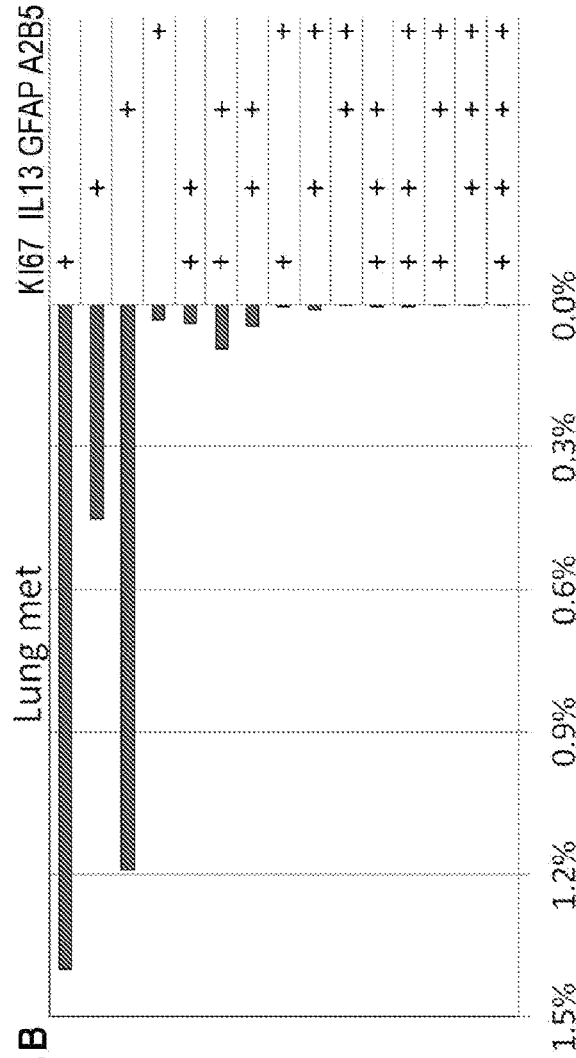

The advantage of concurrent staining for 4 markers and a viability dye (five fluorescence channels) is that each live cell (ViViD$^{low}$) can be traced for its co-expression of 0-4 of the antigens, forming up to 16 (2$^4$) dichotomic (stained/unstained) populations of cells per sample. FIG. 13 depicts these 4-marker combination-gates for Ki67/GFAP/IL13Rα2/A2B5 for live cells derived from four brain-derived tissues run in a single assay. Epileptic brain tissue cells exhibited the expected post-mitotic proliferative quiescence of non-tumorous normal brain tissue. Only 0.2% of cells were dividing (Ki67$^+$). The 0.14% of cells that expressed GFAP-only were not dividing. GFAP is expressed in the healthy brain but is significantly upregulated upon gliosis, or upon malignant transformation. Lung metastasis cells exhibited a non-glial tumor antigen co-expression pattern: 1.4% of the cells expressed only Ki67, 1.2% expressed only GFAP, and 0.45% expressed only IL13Rα2. None of the proliferating cells co-expressed glial-cell or glioma cell markers. AA (grade 3 astrocytoma) cells exhibited an antigen pattern characteristic of glial tumors. Very few cells expressed only Ki67 (<0.2%): the Ki67$^+$ cells co-expressed either IL13Rα2 (0.8%), or GFAP (0.3%) or both (0.5%). Some cells (0.7%) were Ki67$^-$ GFAP$^+$ IL13Rα2$^+$, and the vast majority of GFAP$^+$ stained cells (12.5%) were mitotically quiescent (Ki67$^-$), plausibly non-proliferating AA cells (only a fraction of tumor cells is proliferating in any given time). GBM (grade 4 astrocytoma) cells exhibited a more complex staining pattern than that of the lower grade astrocytoma –AA. Of the ≥1 antigen-stained cells (55%), almost half (26%) expressed Ki67 only. GBMs may harbor proliferating cells which do not stain for GFAP; these cells rapidly proliferate and correlate with tumor invasiveness. Different double positives for Ki67 and any other antigens were found in 1.9%, up to 7.4% of cells. Triple positives (mainly Ki67$^+$GFAP$^+$IL13Rα2$^+$, and Ki67$^+$ GFAP$^+$ A2B5$^+$) accounted for 6.8% of cells. Quadruple positives accounted for 0.7% of cells. More than 80% of the Ki67⁺ cells stained negative to the IL13Rα2 –GAA.

The results demonstrate that multi-parametric flow cytometry for brain-derived cells can distinguish between non-tumorous brain tissue (expressing very low levels of any of the four antigens tested), non-glial tumors (expressing Ki67, but no concurrent glial or GAA antigens expression), and glial tumors (expressing Ki67 and concurrently one or more glial/glioma markers). Differently from histopathology that provides a semi-quantitative estimate on the tumor's proliferative index (i.e. percent Ki67⁺ cells) by microscopic evaluation on several fields within a slide, the assays disclosed herein provide means to quantify this powerful prognostic factor from cells dissociated from one or several tumor piece/s.

VIII. Purification of Tumor Cells Using a Density Gradient

The Tumor panel was used to identify the purity and viability of BT cells before and after a tumor-cell purification step. Tumor cell purification can be done based on antigen expression using MACS or FCM-sorting, or via physical properties, such as adherence to plastic, or using a density gradient purification. A dissociated rat intracranial F98 glioma purified on a density gradient has been shown to demonstrate that the immune protection conferred by vaccination with unpurified dissociated tumor cells is inferior to the protection endowed by lower numbers (~10%) of density-gradient enriched tumor cells obtained from the same sample (Volovitz et al., 2011). Using a rat tumor cell line, it is technically simple to determine the density of the tumor-cell containing layer (TCCL). This is done by running the tumor cell-line (containing only one type of cell) on a parallel density gradient. Differently, in primary human tumors, the TCCL density is unknown. In such a case the Tumor panel can be used to identify which layer contains the BT cells. In addition the Tumor panel may also determine the efficacy of the purification step and the viability of the purified cells. Dissociated human BTs run on Percoll gradients usually produce the following density layers: (1) d<1.019 g/ml containing cell debris and myelin, (d—density) (2) $1.019 < d \leq 1.035$ g/ml usually containing the tumor-cells, (3) $1.035 < d \leq 1.049$ g/ml—a layer that may contain tumor-cells or cell debris or clumped cells, (4) d~1.09 g/ml—a red blood cell layer.

FIG. 14A follows the viability of the unpurified dissociated cells (mean viability=80%), and the viability of cells found in the TCCL (mean viability=88%). The figure shows that whenever the viability of the unpurified cells was high, the gradient kept this high viability. In cases where the unpurified cells' viability was lower, the cells in the TCCL contained a higher fraction of viable cells. FIGS. 14B and 14C depict the analysis of results from a specific tumor sample—a recurrent GBM. FIG. 14B presents the single-antigen expression of unpurified cells and of the cells collected from the TCCL. The results appear conflicting: the unpurified cells contain higher fractions of cells expressing either of the three glial/glioma markers (GFAP/A2B5/IL13Rα2), but lower fraction of Ki67⁺ cells than those found in the TCCL. Thus it is unknown, using the single parameter based analysis, whether the TCCL is enriched for glioma cells of it contains lower percentages of these cells. FIG. 14C presents the same sample's data, but multi-parametrically regroups the cells for those expressing Ki67 only, those expressing Ki67 and one or more glial/glioma markers-X (X represent either GFAP, A2B5, or IL13Rα2), or those cells expressing one or more glial/glioma marker/s but not Ki67. The conflicting uniparametric data is resolved by the multiparametric data: Although the non-proliferating (Ki67⁻) cells expressing glial or glioma markers (X⁺) appear in lower proportions within the TCCL, the TCCL contained higher proportions of proliferating cells that were either Ki67⁺X⁺, or Ki67⁺X⁻.

Example 7. RNA Analysis of Immune Cell Subsets Sorted from GBM Samples

GBM samples were obtained from two patients, dissociated into viable single cell suspensions using Ch NP, washed twice to remove residual protease and samples were stained and analyzed essentially as described in Examples 1-4, with changes and adjustments as described below. Blood samples were also obtained from the patients and PBMC samples were produced from them by the standard ficoll gradient method. PBMC were stained by same procedure as tumor samples. Cells were stained by the ViViD viability dye, washed, and stained using the panels described in Table 9 below:

TABLE 9 panels used for expression pattern analyses

| Panel | Antigens | Fluorochromes | Volume/sample |
|---|---|---|---|
| Lymphocyte | TCRγδ | FITC | 5 |
| | CD14 | PacBl | 0.4 |
| | CD19 | PE | 0.8 |
| | CD3 | APC-eFluor 780 | 1.8 |
| | CD4 | PE-Cy5.5 | 0.4 |
| | CD45 | APC | 3 |
| | CD56 | PE-Cy7 | 3 |
| | CD66b | HRZN V450 | 3.5 |
| | CD8 | BV650 | 1.2 |
| | Total volume | | 19.1 |
| Innate | CD11b | AF 488 | 2.1 |
| | CD14 | BV650 | 5 |
| | CD16 | PE | 0.1 |
| | CD33 | PerCP Cy5.5 | 1.75 |
| | CD45 | APC | 3 |
| | HLA-DR | APC-eFluor 780 | 2.1 |
| | Total volume | | 14.05 |
| DC | CD123 | FITC | 5 |
| | CD14 | BV650 | 2.5 |
| | CD141 | PE | 7 |
| | CD16 | PerCP-Cy5.5 | 0.25 |
| | CD19 | eFluor 450 | 1.35 |
| | CD1c | PE-Cy7 | 5.6 |
| | CD20 | eFluor 450 | 2.7 |
| | CD3 | PacBl | 0.3 |
| | CD45 | APC | 3 |
| | CD66b | V450 | 1.75 |
| | HLA-DR | APC-eFluor 780 | 3.8 |
| | Total volume | | 33.25 |
| DC isotype control | CD14 | BV650 | 2.5 |
| | CD19 | eFluor 450 | 1.35 |
| | CD20 | eFluor 450 | 2.7 |
| | CD3 | PacBl | 0.3 |
| | CD45 | APC | 3 |
| | CD66b | V450 | 1.75 |
| | HLA-DR | APC-eFluor 780 | 3.8 |
| | IgG1 | FITC | 2 |
| | IgG1 | PE | 3.5 |
| | IgG1 | PE-Cy7 | 0.14 |
| | IgG1 | PerCP-Cy5.5 | 0.8 |
| | Total volume | | 21.84 |

PBMC were run on FACS ARIA III flow cytometer and used to guide gating of specific immune cell subsets. GBM Samples were then run shortly to validate gating, and then sorted unto standard microscope carrier glass slide, to verify the quality of sorting procedure, as well as into an inverted cap removed from a nuclease free 1.5 ml eppendorf tube, containing 150 µl of the lysis buffer supplied with the RNAqueuos-Micro kit (Ambion). Collected cell populations included: Lymph panel—Th, Tc, and B cells; DC panel—mDC1, mDC2, pDC, CD16$^+$ mDC; Innate panel—macrophages, neutrophils, microglia, CD16$^+$ NK cells and γδ T cells. However, since negligible numbers of γδ T cells were found to be present in the tumors, these cells were not used for further analyses.

Lysates were immediately frozen in −80° C. and maintained until production. Lysates were thawed on ice and subjected to RNA purification and DNase treatment using the RNAqueuos-Micro kit according to manufacturer's instruction. An aliquot of each RNA sample was analyzed on the 2100 Bioanalyzer (Agilent) using the RNA 6000 Pico kit (Agilent) to validate RNA integrity. Samples with applicable signal detected were used to appraise production quality. RNA samples were reverse transcribed using the qScript cDNA Synthesis Kit (Quantabio) according to manufacturer's instructions and diluted at end of reaction to equal volumes.

cDNA samples were analyzed by quantitative RT-PCR using the fast PCR program on the StepOnePlus thermocycler (ABI) and the PerfeCTa SYBR Green FastMix (Quantabio) according to manufacturer's instruction. All reactions were performed in duplicates. Primer were used at a final concentration of 500 nM, and all sets used in the RT-PCR reaction are detailed in Table 10 below and were validated by calibration curve assays.

Figure 15A:
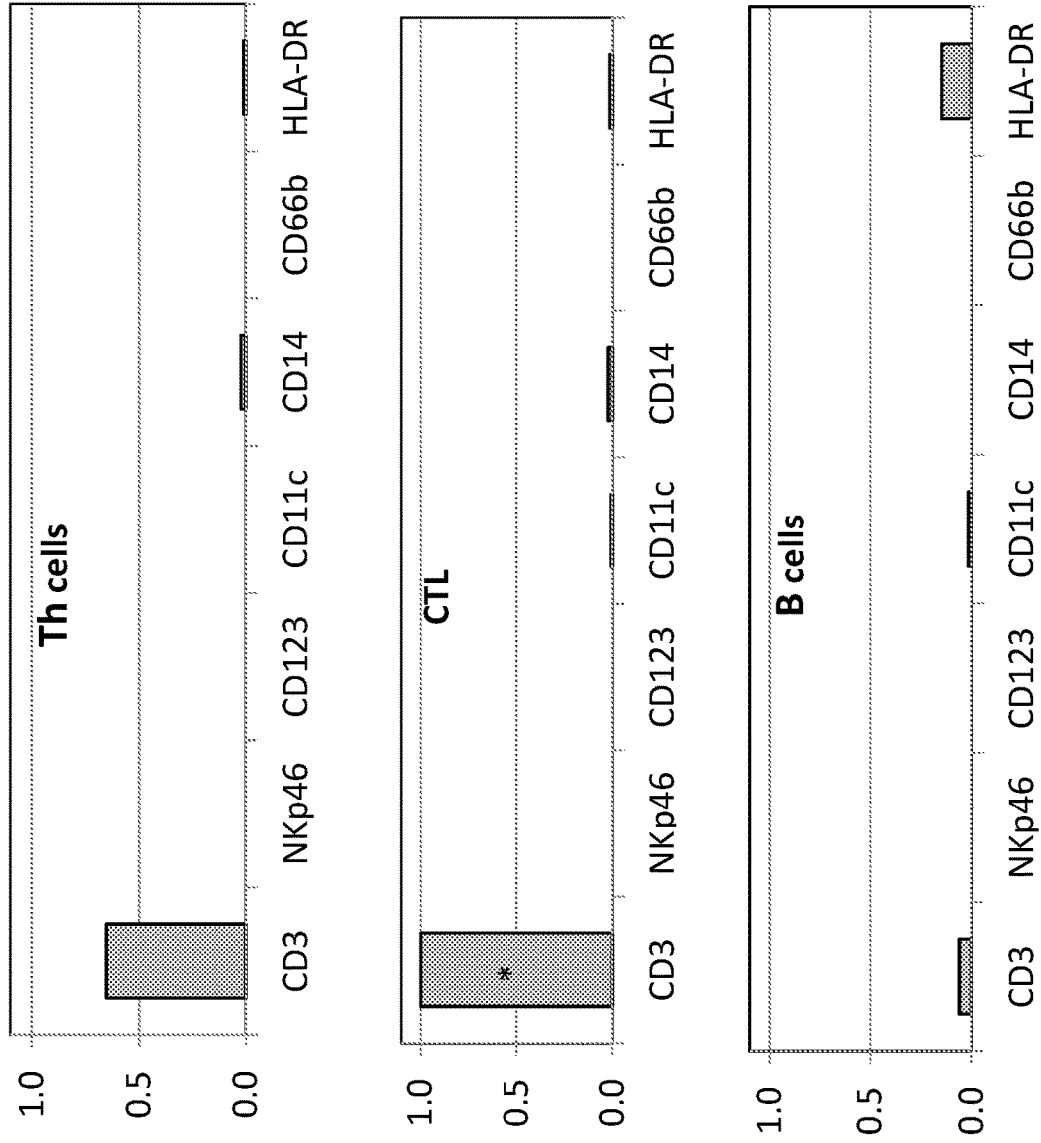
FIG. 15A-C. Real-time PCR analysis of relative expression of immune subset population markers (CD3ε, NKp46, HLA-DR, CD14, CD66b, CD123, CD11c) on immune populations sorted from brain tumors with the different panels (FIG. 15A—lymph panel sorted cells.
Figure 15B:
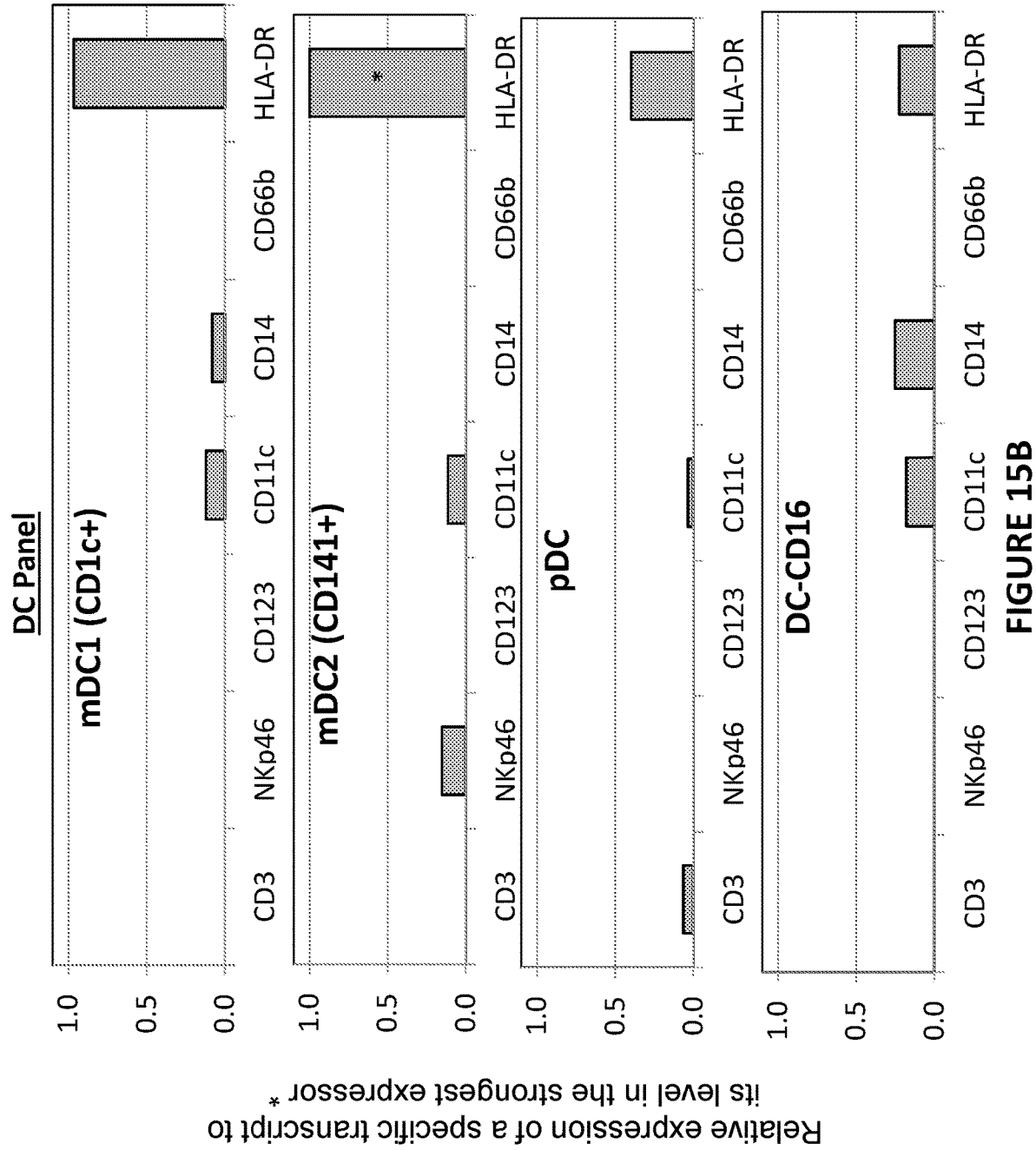
Figure 15C:
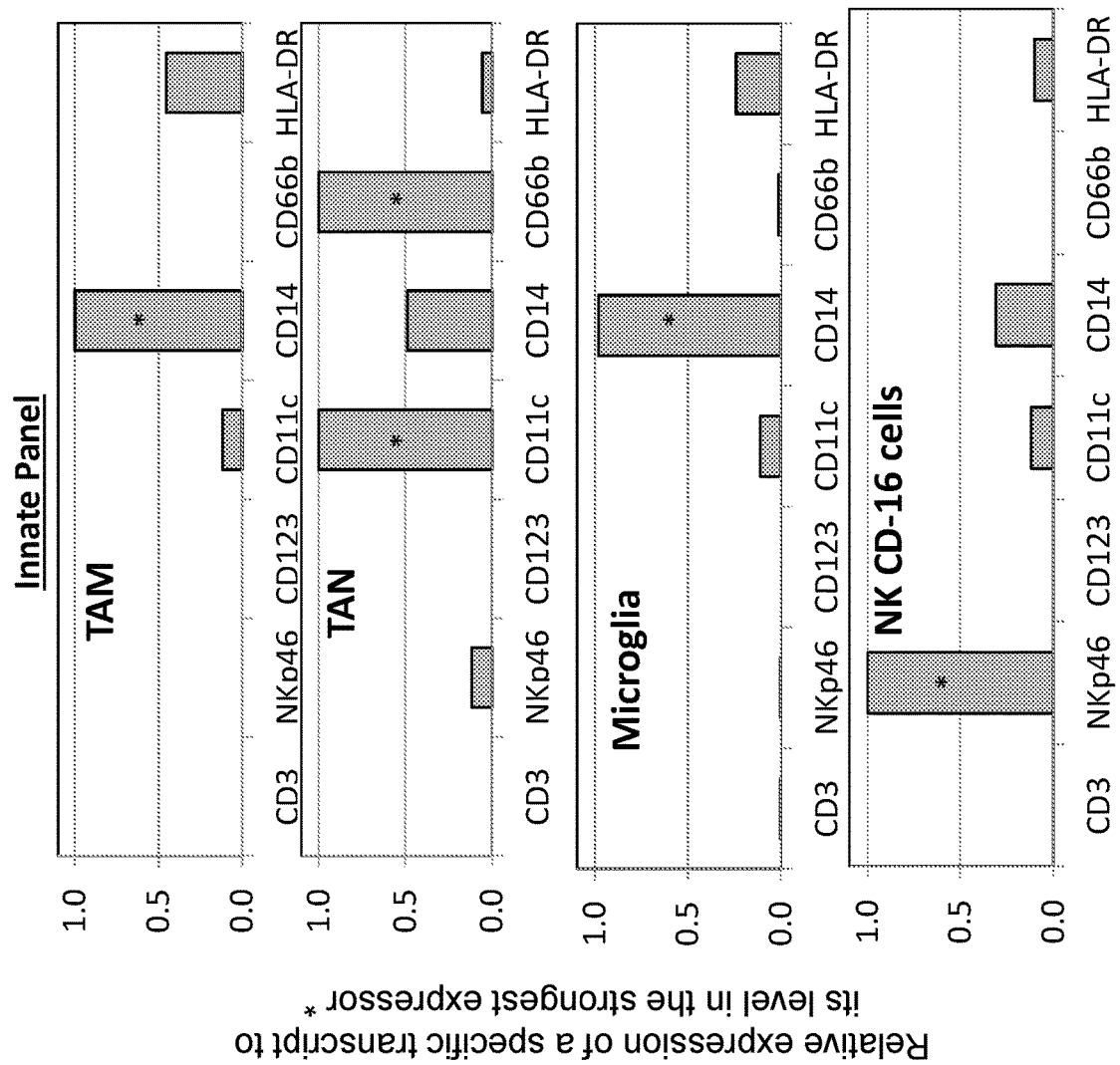

All results were obtained by setting the threshold of detection (Ct) to 0.15, and values are presented as ΔCt (not ΔΔCt), which enables comparison of relative expression between different patients. Geometric mean of the results from 2-3 housekeeping genes (GAPDH, RPLPO, HPRT) were used to normalize results for genes of interest. Analysis of relative expression of select immune subset population markers (CD3ε, NKp46, HLA-DR, CD14, CD66b, CD123, CD11c) was performed as a quality assurance step, to reconfirm the purity of the cell sorting process. As can be seen in FIG. 15, the sorted populations were confirmed to be highly pure, with no contaminations of other immune cell populations identified.

TABLE 10 primers used for expression pattern analyses

| Name | SEQUENCE | SEQ ID NO: |
|---|---|---|
| PD1 Forward | GGTGCTGCTAGTCTGGGTCC | 1 |
| PD1 Reverse | GGAAATCCAGCTCCCCATAGT | 2 |
| PD-L1 Forward | GGGCATTTGCTGAACGCA | 3 |
| PD-L1 Reverse | GCCAATTAGTGCAGCCAGGT | 4 |
| TIM3 Forward | TCCAAGGATGCTTACCACCAG | 5 |
| TIM3 Reverse | GCCAATGTGGATATTTGTGTTAGAT | 6 |
| Galectin 9 Forward | CCTTTCATCACCACCATTCTG | 7 |
| Galectin 9 Reverse | ATGTGGAACCTCTGAGCACTG | 8 |
| CEACAM1 Forward | GAGTAGTGGCCCTGGTTGCTC | 9 |

TABLE 10-continued primers used for expression pattern analyses

| Name | SEQUENCE | SEQ ID NO: |
|---|---|---|
| CEACAM1 long | CGCTGGTCGCTTGCCCT | 10 |
| LAG3 Forward | TCACTGTTCTGGGTCTGGAG | 11 |
| LAG3 Reverse | CACTTGGCAGTGAGGAAAGA | 12 |
| Galectin3 Forward | TTTTCGCTCCATGATGCGTTA | 13 |
| Galectin3 Reverse | GCCTGTCCAGGATAAGCCC | 14 |
| HLA-DR Forward | GGACAAAGCCAACCTGGAAA | 15 |
| HLA-DR Reverse | AGGACGTTGGGCTCTCTCAG | 16 |
| PRLP0 Forward | GGGCACCATTGAAATCCTGAGT | 17 |
| PRLP0 Reverse | ATGTTCAGCAGCGTGGCTTC | 18 |
| GAPDH Forward | CCTCCTGTTCGACAGTCAGC | 19 |
| GAPDH Reverse | GTTAAAAGCAGCCCTGGTGA | 20 |
| HPRT1 Forward | TGACACTGGCAAAACAATGC | 21 |
| HPRT1 Reverse | AACACTTCGTGGGGTCCTTT | 22 |
| CD3E Forward | CCAACCCAGACTATGAGCCC | 23 |
| CD3E Reverse | GCAGTGTTCTCCAGAGGGTC | 24 |
| NKp46 Forward | CAGCAGCAGACTCTCCCAAA | 25 |
| NKp46 Reverse | CCTGGCAACAGATGGTCACT | 26 |
| CD123 Forward | AGCGCACACGGGAAGATATC | 27 |
| CD123 Reverse | GGTGCCTGCTTAAATGGAGATC | 28 |
| CD11c Forward | ACAGCCAATGTGAGCAGTGA | 29 |
| CD11c Reverse | TTGTTCGTGGCTGCTAACCA | 30 |
| CD14 Forward | GAAGACTTATCGACCATGGAGC | 31 |
| CD14 Reverse | AGACGCAGCGGAAATCTTCA | 32 |
| CD66b Forward | TTCTCCTGGCCTCTCAGCTA | 33 |
| CD66b Reverse | CAACTGTCTGCCAGTCTTCTTG | 34 |

Analysis of expression of select immune checkpoint molecules and their ligands (PD1 and PD-L1, TIM3 and CAECAM1 and Galectin 9, LAG3 and Galectin 3 and HLA-DR) was performed in order to assess the immune suppression statuses of each subset. In other words, each subset was assayed for expression of molecules capable of suppressing other immune subsets, as well as molecules indicating that the subset is at a suppressed state. Populations were binned into strong expressers, weak expressers and non-expressers, and these classifications were used to construct a schematic of the different immune suppressive layers within each original GBM sample.

Expression of immune inhibitory/suppressive molecules was arranged on the level of suppressive or stimulatory layers, incorporating molecules that interact with each such as CEACAM1, TIM3 and Galectin9. Such layers also incorporate the number of cells from each subset and the level of expression of each transcript (molecule) in each cell subset. To define higher versus lower levels of expression, all results were normalized to the total RNA purified, by means of ΔCt in real-time PCR or Fragments per Kilobase of transcript per Million mapped reads (FPKM), in RNA-Seq.

Figure 16A:
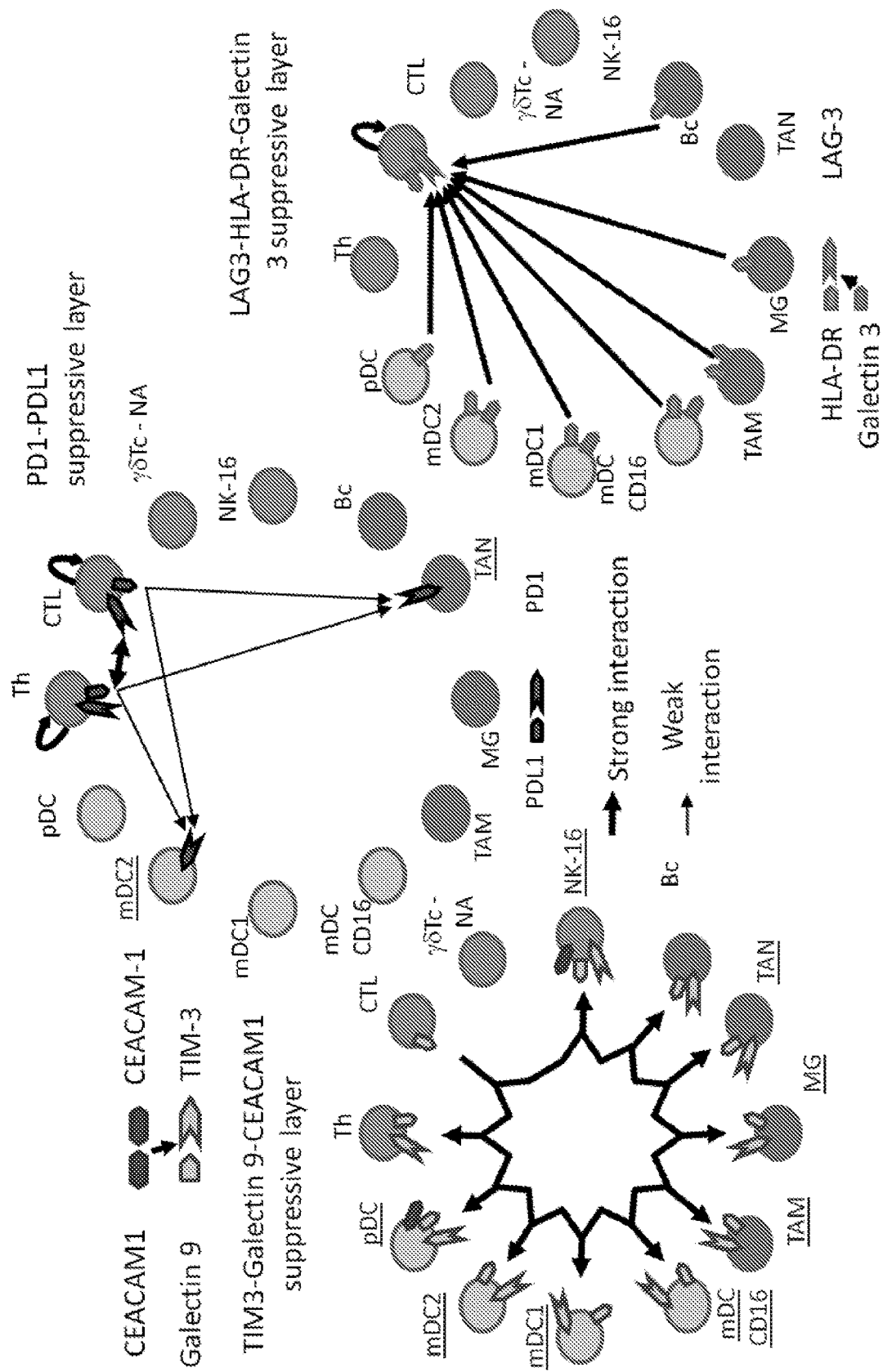
FIG. 16A-B. Real-time PCR analysis of expression of immune checkpoint molecules and their ligands (PD1, PD-L1, TIM3, CAECAM1, Galectin 9, LAG3, Galectin 3 and HLA-DR) on immune populations sorted from tumors of two GBM patients (FIG. 16A, patient 1, FIG. 16B, patient 2). Bold lines represent high expression levels (strong interaction), narrow lines represent low expression levels (weak interaction), and the direction of the arrows point from the suppressor cell population to the suppressed cell population (e.g. from PDL1 to PD1 expressing cells).
Figure 16B:
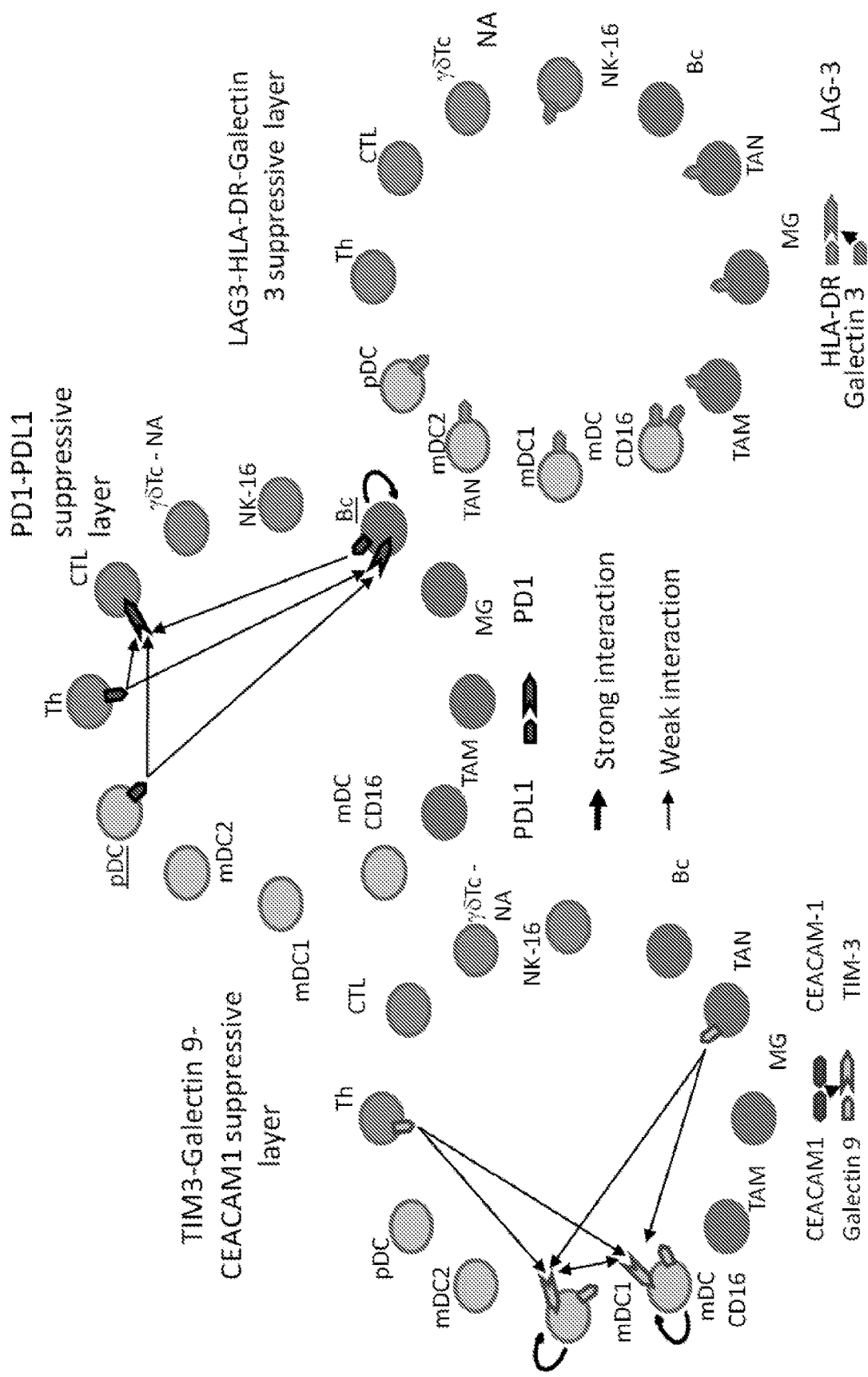

Cell subsets that expressed interacting molecules were connected, wherein the strength of interaction is defined depending of the interacting molecules' expression level. As can be seen in FIG. 16A-B, in patient 2 (FIG. 16B), TIM3 is expressed solely by two types of myeloid DC, Galectin 9 is expressed by these two DC, as well as by CTLs and tumor associated neutrophils (TANs) within the tumor. The expression of TIM3 in the DC was high while the expression of Galectin 9 was low by all other expressing cells, the interaction was therefore defined here as a weak interaction. In patient 1 (FIG. 16A), the expression of PD1 and PDL1 by CTL and Th was high, while PD1 expression in TANs and myeloid DC-2 (CD141+) was low. PDL1 was strongly expressed only by CTL and Th in patient 1. Thus the interactions between CTL-Th and their self-interactions (e.g. CTL-CTL) were defined as strong. The suppressive interaction of PDL1-PD1 to TANs or mDC2 was defined here as weak.

Data were used to define algorithmic rules for treatment. Such rules include information from all layers of data collected. An example of such rule is a PD1 blockade rule: IF [CTL numbers within the tumor are high (>0.8%)] AND [the expression of PD1 is high on the CTL] AND [[the expression of PDL1 is high on mDC-1 (CD1c+) OR mDC-2 (CD141+) which are found in high numbers (>0.1%) within the tumor] OR [the expression of PDL1 on the tumor cells is high]] AND [LAG3 is NOT expressed on CTLs] THEN PD1 blockade will have a significant positive clinical effect on the patient as a single agent. Accordingly, patient 2 would be more likely to benefit from PD1 blockade single-agent immunomodulating treatment than patient 1.

REFERENCES

1. Fridman W H et al., Nat Rev Cancer. 2012 Mar. 15; 12(4):298-306.
2. Galluzzi, L., et al., Nat Rev Drug Discov, 2012. 11(3): p. 215-33.
3. Lamoreaux L et al., Nat Protoc 2006; 1: 1507-16.
4. Perfetto, S. P. et al., Nat Rev Immunol 4, 648-655 (2004).
5. Volovitz, I. et al. J Immunol 187, 5452-5462 (2011).

The foregoing description of the specific embodiments will so fully reveal the general nature of the invention that others can, by applying current knowledge, readily modify and/or adapt for various applications such specific embodiments without undue experimentation and without departing from the generic concept, and, therefore, such adaptations and modifications should and are intended to be comprehended within the meaning and range of equivalents of the disclosed embodiments. It is to be understood that the phraseology or terminology employed herein is for the purpose of description and not of limitation. The means, materials, and steps for carrying out various disclosed functions may take a variety of alternative forms without departing from the invention.

The invention claimed is:

1. A kit for identifying dendritic cell populations in a human tissue sample, comprising a fluorescent viability dye and distinct fluorophore-labeled antibodies directed to human CD45, CD14, HLA-DR, CD1c, CD141, to at least one of CD123, CD303 and CD304, and to a plurality of lineage-specific markers comprising: at least one human T cell-specific cellular marker, at least one human B cell-specific cellular marker and at least one human granulocyte-specific cellular marker, wherein said fluorophore labeled antibodies to said plurality of lineage-specific markers and said viability dye are distinct from said fluorophore labeled antibodies directed to human CD45, CD14, HLA-DR, CD1c, CD141, and to at least one of CD123, CD303 and CD304; and optionally a distinct fluorophore-labeled antibody directed to CD16.

2. The kit of claim 1, wherein said kit comprises at least one of:

a) a cytometric panel for identifying innate immune cell populations comprising a viability dye and distinct fluorophore-labeled antibodies directed to human CD45, CD11b, CD14, HLA-DR, CD16, CD33 and optionally CD66b; and b) a cytometric panel for identifying lymphocyte populations comprising a viability dye and distinct fluorophore-labeled antibodies directed to human CD45, CD3, CD4, CD8, CD56 and optionally CD11b, and to at least one of TcR-Vα24Jα18, CD19 and CD20, and a plurality of lineage-specific antibodies, comprising: at least one antibody directed to a human monocyte/macrophage cellular target and at least one antibody directed to a human granulocyte cellular target, wherein if said panel comprises an antibody directed to TcR-Vα24Jα18, said lineage-specific antibodies further comprise at least one antibody directed to a human B cell cellular target.

3. The kit of claim 1, wherein said panel comprises:

(i) said antibody directed to human CD45, conjugated to allophycocyanin (APC) or a substantially equivalent fluorophore;

(ii) said antibody directed to human CD14, conjugated to Brillian Violet 650 (BV650) or a substantially equivalent fluorophore;

(iii) said antibody directed to human HLA-DR, conjugated to APC eflour 780 or a substantially equivalent fluorophore;

(iv) said antibody directed to human CD1c, conjugated to phycoerythrin-cyanine 7 (PE-Cy7) or a substantially equivalent fluorophore;

(v) said antibody directed to human CD141, conjugated to phycoerythrin (PE) or a substantially equivalent fluorophore;

(vi) said at least one antibody directed to human CD123, CD303 or CD304 conjugated to fluorescein (FITC) or a substantially equivalent fluorophore;

(vii) ViViD violet or a substantially equivalent viability dye;

(viii) said plurality of lineage-specific antibodies comprising an antibody directed to human CD3, at least one antibody directed to human CD19 or CD20 and an antibody directed to human CD66b; the lineage-specific antibodies conjugated to Pacific Blue or a substantially equivalent fluorophore; and optionally (ix) said antibody directed to human CD16, conjugated to peridinin-chlorophyll-protein-cyanine 5.5 (PerCp-Cy5.5) or a substantially equivalent fluorophore.

4. The kit of claim 1, further comprising a cytometric panel comprising: a fluorescent viability dye and distinct fluorophore-labeled antibodies directed to human KI67, glial fibrillary acidic protein (GFAP), IL13 receptor α2 (IL13Rα2), and A2B5.

5. The kit of claim 1, further comprising at least one reagent providing enzymatic dissociation of cells from a tissue sample, wherein the reagents comprise *Clostridium histolyticum* Neutral Protease (Ch NP), and/or instructions for use of said kit in characterizing cell populations in an enzymatically dissociated tissue sample, said sample being a solid tumor sample or a cerebral tissue sample, wherein the dissociation comprises incubation with Ch NP.

6. The kit of claim 1, wherein said plurality of lineage-specific markers are conjugated to the same fluorophore or substantially equivalent fluorophores.

7. The kit of claim 1, wherein distinct fluorophores are fluorophores that may be used with a flow cytometer to facilitate concurrent measurement and separation of said fluorophores.

8. The kit of claim 7, wherein fluorophores that may be used with a flow cytometer to facilitate concurrent measurement and separation of said fluorophores are fluorophores whose light is captured by distinct flow cytometer filters.

9. The kit of claim 1, wherein distinct fluorophores are fluorophores with different emission spectra.

10. The kit of claim 1, wherein distinct fluorophores are fluorophores with non-equivalent emission maxima, wherein equivalent emission maxima are maxima within ±50 nm of each other.

11. The kit of claim 1, wherein said fluorescent viability dye is distinct from said distinct fluorophore-labeled antibodies to the plurality of lineage-specific markers and distinct from said fluorophore labeled antibodies directed to human CD45, CD14, HLA-DR, CD1c, CD141, to at least one of CD123, CD303 and CD304.

12. The kit of claim 1, wherein said distinct fluorophore-labeled antibody directed to human CD45 comprises a fluorophore with a staining index of at least 200.

13. The kit of claim 1, wherein said distinct fluorophore-labeled antibody directed to human CD45 comprises APC or a substantially equivalent fluorophore in terms of fluorescence yield, staining index, or maximal emission wavelength.

14. A kit for identifying dendritic cell populations in a human tissue sample, comprising a fluorescent viability dye and distinct fluorophore-labeled antibodies directed to human CD45, CD14, HLA-DR, CD1c, CD141, to at least one of CD123, CD303 and CD304, and a plurality of lineage-specific markers comprising: at least one human T cell-specific cellular marker, at least one human B cell-specific cellular marker and at least one human granulocyte-specific cellular marker, wherein said distinct fluorophore-labeled antibody directed to human CD45 comprises a fluorophore with a staining index of at least 200 and optionally a distinct fluorophore-labeled antibody directed to CD16.

* * * * *